US010889800B2

(12) United States Patent
Noggle et al.

(10) Patent No.: US 10,889,800 B2
(45) Date of Patent: Jan. 12, 2021

(54) METHOD AND COMPOSITION FOR GENERATING BASAL FOREBRAIN CHOLINERGIC NEURONS (BFCNS)

(71) Applicants: New York Stem Cell Foundation, Inc., New York, NY (US); ICAHN SCHOOL OF MEDICINE AT MOUNT SINAI, New York, NY (US)

(72) Inventors: Scott Noggle, New York, NY (US); Maitane Ortiz-Virumbrales, New York, NY (US); Sam Gandy, New York, NY (US); Ilya Kruglikov, New York, NY (US); Michelle Ehrlich, New York, NY (US)

(73) Assignees: New York Stem Cell Foundation, Inc., New York, NY (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/990,208

(22) Filed: May 25, 2018

(65) Prior Publication Data

US 2019/0002826 A1  Jan. 3, 2019

Related U.S. Application Data

(60) Provisional application No. 62/511,271, filed on May 25, 2017, provisional application No. 62/571,741, filed on Oct. 12, 2017, provisional application No. 62/574,639, filed on Oct. 19, 2017, provisional application No. 62/586,571, filed on Nov. 15, 2017.

(51) Int. Cl.
| | |
|---|---|
| *A61K 35/30* | (2015.01) |
| *C12N 5/0793* | (2010.01) |
| *C12N 15/11* | (2006.01) |
| *C12N 9/22* | (2006.01) |
| *G01N 33/50* | (2006.01) |
| *C12N 5/074* | (2010.01) |

(52) U.S. Cl.
CPC ............ *C12N 5/0619* (2013.01); *A61K 35/30* (2013.01); *C12N 5/0696* (2013.01); *C12N 9/22* (2013.01); *C12N 15/11* (2013.01); *G01N 33/5058* (2013.01); *C12N 2310/20* (2017.05); *C12N 2501/15* (2013.01); *C12N 2501/41* (2013.01); *C12N 2501/999* (2013.01); *C12N 2506/02* (2013.01); *C12N 2506/45* (2013.01); *C12N 2510/00* (2013.01); *C12N 2800/80* (2013.01); *G01N 2800/2814* (2013.01)

(58) Field of Classification Search
CPC .... C12N 5/0619; C12N 5/0696; C12N 15/11; C12N 9/22; C12N 2506/02; C12N 2501/15; C12N 2501/41; C12N 2510/00; C12N 2506/45; C12N 2501/999; C12N 2800/80; C12N 2310/20; A61K 35/30; G01N 33/5058; G01N 2800/2814
See application file for complete search history.

(56) References Cited

U.S. PATENT DOCUMENTS

| | | |
|---|---|---|
| 7,022,893 B1 | 4/2006 | Takeda et al. |
| 2012/0207744 A1 | 8/2012 | Mendlein et al. |

FOREIGN PATENT DOCUMENTS

| | | |
|---|---|---|
| WO | WO 2006/029197 A1 | 3/2006 |
| WO | WO 2014/176606 A1 | 10/2014 |

OTHER PUBLICATIONS

Ochalek et al., Hindawi Publishing Corporation, Stem Cells International, vol. 2016, Article ID 5838934. (Year: 2016).*
Ortiz-Vimbrales et al., Acta Neuropathologica Communications, 5:77, 2017 (Year: 2017).*
Rajala et al., Human Reproduction vol. 22, No. 5 pp. 1231-1238, (Year: 2007).*
International Search Report dated Aug. 23, 2018, regarding PCT/US2018/034725.
Nakajima et al.: "Dissociated cell culture of cholinergic neurons from nucleus basalis of Meynert and other basal forebrain nuclei"; Proc Natl Acad Sci USA, Sep. 1985, vol. 82, pp. 6325-6329.
Ortiz-Virumbrales et al.: "CRISPR/Cas9-Correctable mutation-related molecular and physiological phenotypes in iPSC-derived Alzheimer's PSEN2 N141I neurons"; Acta Neuropathol Commun, Oct. 27, 2017, vol. 5, No. 1:77, pp. 1-20.
Pires et al.: "Generation of a gene-corrected isogenic control cell line from an Alzheimer's disease patient iPSC line carrying a A79V mutation in PSEN1"; Stem Cell Res, Aug. 7, 2016, vol. 17, No. 2, pp. 285-288.

* cited by examiner

*Primary Examiner* — Kimberly Ballard
*Assistant Examiner* — Stacey N MacFarlane
(74) *Attorney, Agent, or Firm* — DLA Piper LLP (US)

(57) ABSTRACT

The invention relates to methods and compositions for developing basal forebrain cholinergic neurons (BFCNs) from stem cells, and in particular, BFCNs having repaired electrophysiological defects relating to one or more mutations in PSEN2, and to the use of such BFCNs in cell-based therapies to treat Alzheimer's disease.

24 Claims, 11 Drawing Sheets

Specification includes a Sequence Listing.

```
                      SEQUENCE LISTING

<160> NUMBER OF SEQ ID NOS: 31

<210> SEQ ID NO 1
<211> LENGTH: 33258
<212> TYPE: DNA
<213> ORGANISM: Homo sapiens
<220> FEATURE:
<221> NAME/KEY: misc_feature
<223> OTHER INFORMATION: chromosome 1, GRCh38.p12 Primary Assembly

<400> SEQUENCE: 1
ggggcctggg ccggcgccgg gtccggccgg gcgctcagcc agctgcgtaa actccgctgg      60 agcgcggcg cagagcaggt gagcgggcgg tgccgggggg tgcccaggcc agggccctgt     120
cgcctgcggc gctgagggcc cggggtgggg ctgcgccctg agggccctgc cctgccctcc     180
gcacgcctct ggccacggtc ccttccccgg ctgtgggtct gcggcccctg cgtgcgcagc     240
gctcctggcc tctgcggcca gcgcggggc ggagagagga gagtgcccgg caggcggcgg      300
ctgggccggc ccggaactgg gtcgtggaag gatcgcgggg agcggccctc aggccttcgg     360
cctcactgcg tccccacttc cctgcgcccg cctgccgccg agcccggct gggggtgggc      420 gcggcgcgag cggttaaagg gccggtgcat ttaaaggagc ggtgcacgtg ggtctctgag     480
gcgtgtagca ggcgggggcg ttttgttctt cttctctctc gccggagacc tccgttgcgc     540
cgagtccatt cggcctctag caccgggtcc tgggcatgct ttccccggga aggaggcgcg     600
cgggggctct gcccgcacgt gaggggcagg gccgcaggct caagcctaga gccggtttct     660
gttagcagcg gtgtttggct gttttatcag gcatttccag cagtgaggag acagccagaa     720
gcaagctttt ggagctgaag gaacctgaga cagaagctag tccccctct gaattttact      780 gatgaagaaa ctgaggccac agagctaaag tgacttttcc caaggtcgcc caggtacgat     840
atagcagagc caggcttcga ccccagtgtc ctggcttcta gatctgctgt ccatccctcc     900
gagcagacct caccctgtt tattgcctta ataagtattc cctttgaaag gtatgaacgg      960
tgttgagtga agtaactgca tccctattta caaatggaga acctgagagc attccataga    1020
gacgattgta gactaactta actcagaagc gacagcctgg ggttgccaag gctgtctacg    1080
aagtaacttg attaggaccg accccagctt ccagtaagga agcctctgat gcctctgtag    1140
ccaattctgc agacacctga gcctccaagg ccttcagcca agacctttgg cggtaattgg    1200
agtctcggga taagctgctt caggtgtgtg agcctcaggt tcttctctcc tgaatgtggt    1260
tgtgggcagc cggtgactgg cgcaggtgca gaaggggcct ggttcttggc cccacctcag    1320
```

-continued

```
agctgcgtcc tcacgacgcc cacgttgagc cttgggttcc agggcagaga ctggagtgag    1380
ggcttggggg catgttgctt tgaagtggga tggatgtatc aggttttggg ggaaaactct    1440 gtacccttg  gtgttgaagt gcccatgtgc caagtcttga gtccagcatg ttcacatgtg    1500
gggagtgagt ggcttgttcc tgtctatttg aaagagcagc aaggaggagg aggagcaagg    1560
gctaggggct gctgctgggg tgcctggagc tgtggtgcat aatgtcacac ctgtctcccc    1620
tccgtagctg ctcaccgtcc ccccaagggg gtttgcctc  ttgcctactt tggccttct    1680 ctgttatcga tgttaataat gacatatatc tcgcttatga gttggtcata ataaaaagct    1740
atcttgtaca gaatattaga atttaagatc ttaagaattt caatgacact gaaatagttt    1800
attattacct ttttacagaa gaggaaacaa gttcagggag ttaagcagct agtccagtta    1860
tgtggcttca gtgctttaag caccaggatt tgaacatagc tggctacact gtctttatct    1920
cttgagtttt tgcgcaggag gttcctgtat tcaactccta cccgtgtctc tccactactg    1980
ctgggaaagt tttgtggagt ccccatgagc aacttcctga caaacaaaca aaatttttt     2040 aaagaaacca aagcagtgtg tgtaggtcac atgcagtgtg tctaatgaaa acatctctgg    2100
cgggttttca gctgttgctt tgactttcgg acactgttta gttggggact gataagacag    2160
caaatatttc tgcaagtatt cccacctgtt ctattcccag ctgccacagc tgcggaaagg    2220
cgggggtgag gctgagaggc cccgagagga acattttcca ctgggctcca atcctggaga    2280
tgggatgacc atcatgttaa tgtctggaga aaagaatgat ttcaggctgg gtgctgtggc    2340
tcatgtctgt aatcccagca ctttgggagg ccgaggtggg tggatcacct gaggtcggaa    2400
gtttgagacc agcctgacca acatggagaa accccatctt tactaaaaat acaaaattag    2460
ccgggcgtgg tggcacatgc ctgtaatccc agctactcag gaggctgagg caggagaatc    2520
gcttgaaccc aggaggcgga ggttgcagtg agccgagatc gggccatggc actccagcct    2580
gggcaacaag agcaaaactc catctcaaaa aaaaaaaaat ggtttcacat cagtcctcag    2640
gaaagatcag atgtcagtga gggagatcat ttcttgagag cctcttcact gagtgggaga    2700
atgggctgct tgttcatctt tgtgaaaatt ctagaacggg aagaacaatt caaagggtgt    2760
ccaccattct gctgtacctt aaccagaaac ttactgact  cttttaaaa  taaaagtaat    2820 tcatgtttat tctagaaaat tagggaaaaa aaattttttt tgagatggag tttcactctt    2880
gttgcccagg ctggagtgcg atggtatgat ctcagctaac tgcaacctct gcttgccggg    2940
ttctagcgac tctcctgcct cagcctcctg ggtagctggg attacaggtg cctgccacca    3000
ctcccagcta atttttgtat ttttattaga gtcggggttt caccatgttg gccaggctgg    3060
tctcaaactc ctgacctcag gtgatccgcc aaccttggcc tcccaaaatg ctggtattac    3120
aagcataagc cattgcgctg ggctgagata accactctta acatgcattt ccttccacac    3180
tgttcacata tgcatattta tctattaaaa caatagaggg agggaaccgt aggtgaagtt    3240
tgtgtatcct gttttttctg ttatgccttc agaattttcc tttattgag  tactcatgga    3300 aaagcagatt tgatggctgt gtagagcatt tgaattattt atcctaccag tcccacagca    3360
ggacactttc ccaccctccc ttttgcccca gagaagcagt gccctctgtc tccccatgc     3420 ccatatgtgg gcactcccca ccatggagcc aaacctacct gggcaagtag cagagggaga    3480
gcagagtgag ccctggggc  aggagagaga cttgagagtt tgaggtgac  agatgagctg    3540 gtgagtgagt gattagggag catttcttga cacatacctg cccgtggtga aggcatgtgt    3600
cttgtgagtg tgctcccaga aagcctgtgt agtgtgtggt gggcctgcct gtgtgaccaa    3660
```

```
accctggcca ctgggtacgt gaccctcaca agtgctgact gggctgagaa gagctccttg   3720
atgggcagtt tggagacttg agttgtaact gtggcttttg ccatgggac attaactgat    3780
tacttttgcc cctctaggct tcagttgtcc ttaattataa tacagggagc tgactaggtg   3840
gcgttgatgg cctttacggt ccttgccagc tctgacattg tcctatggat atgtcctttc   3900
atttgataat atgtttacgt ggccatagtg cctggggctg ggccgggaat ggaaacttga   3960
tctctgggc ctggcctttg aagccagttc atgtgtctgg tggttcagca gatccgtaac   4020
tttccaagag gcacatccat aggctaccgt gtcctttctc actgtgtccc tcctccattt   4080
catcttcttt ataactacga cttattgaac atctactgtg tgctgacac tttacaggtt    4140
atctctaggt tttacgataa tcttgcaagg tatgcctgtt ctgcttttta cagcagagga   4200
aatgagctgt gtcagattag actgtctgag gcctcttggc cagggagtat gtggttcaaa   4260
tcacataggc aggcgatctg aaccctgtca gtctccaaag cctctgcttt tgaccgctga   4320
cttgctgctg cttgtttaaa aataaatgtg tttctggagc ctactccaga ggggcgtgct   4380
aggggctccc tctcccactt ccccacaaac cacccttttc cctggctgct tcaggaaatg   4440
agagaactct gcctgggccc caggcacttg tgagtgggac agggctgtta gaggtaagtc    4500
tagagcctgg cccaaaattc aggaggcccc atcagagggc ccctggggcc tgtggtccgg   4560
gagggtggta gggcagtacc tcacttccct ttgagactca ggccccagct ctggcttagg   4620
ccagggagaa ccatccccaa gtggtatgtg ttactatatg agctgagatg gatggtcagc   4680
tggaccaaat acatagtcgg gtacccaggg ccaggggag gaaggtgagc agggaagctg    4740
tgggcaattg tctgggtatc acctgacctt agcaaactct tccttgtttt aagcgaggac   4800
gtgggacttc tcagacgtca ggagagtgat gtgagggagc tgtgtgacca tagaaagtga   4860
cgtgttaaaa accagcgctg ccctctttga aagccaggga gcatcattca tttagcctgc    4920
tgagaagaag aaaccaagtg tccgggattc agacctctct gcggcccaa gtgttcgtgg    4980
taagtgcagt gactcccaac ctgcttttga accctctttt tccattagga ttttctccgt   5040
ggaggcagat ttccatggga gtttgctgtg gcattttgaa atctgtttct tacctagttc   5100
cattggcctt aaatgttaag gccaaagcct ttacatttct ctgtaatgaa aagaaggtcg   5160
aggaaattgg gtcattgggt ttccataatg attgcaggaa ctgctgacac aagcacggct   5220
ggggagattc tctaggtcag actcccttgg tttggctaat tcagcagttt gatcccattc   5280
agctgattaa tgggaatgtg cagtggcttc tttggatgtt tgattttgca tcctaatcca   5340
aagcagctat cagcctcagc acttccttgt tggaaggctt tccagaacgt agtctatgtt   5400
ggacacttcc ttctgcctct ctgcattttc ctgccacttc tctagagaat ggggtgcagg    5460
gggtgggaga cggggaaagc tggtcgctga gtggctgatg ggacttgaca tcacccagcc   5520
ccaccccac ctgcccgtga gtcagcctcc ggggagagtt catcgcgtca ccggcactct     5580
aatgtggaca gacacctagc agtgttgttt atctgcacac gtttgggtgg tgattttcc    5640
ctccaaggat ttcagagcac cagcaggctt cagagcagac ttaggtggct tgcaaagcag   5700
gccctcagga attcagaggg tagcagaagt ccatcccaga tgctctgttt tccttcagga   5760
gctaggtaaa tcagaggggc tgaggacaa atgaaaaaag ttacagcctt tgagtcccat   5820
ctgctcctcc tggccaatga gagggatct gggaggggca gatgtagagg aaaatctgtc    5880
taaatgttga tgctcgttat tttccttta agaattaata gcctaaaata aaccctacag    5940
atacagtctg tgtttattat ggcgacttag agaaatgcag aaaatatca agaaaataa      6000
aaccactctt ggttctacca tgcaaagata atcatcttta atgttttgta atatttccga   6060
```

```
tcttttatat acatacattt tataaggaca ttcagatgat caggttcgta aagttttatg    6120
ttcggttaaa tttaacagcg tgtcattgtt caggttatta aatgtttgaa ataagatttt    6180
tggtggtcct gtcacagtct ccatgaagta gcatttcagg atcgaaaggt atgctgtgtt    6240
taaagtgttg attcttactc ctttcagtta aggccagtgc agtttgtcca ggtagtgact    6300
gagacccagt ttttccacac tctcctccgc agtgggcatt gttttgggcc ttttcagcc     6360 caagagctct cttctcccca tgccgctctg ctggtctgag attttccac tcctcctcct     6420 ccctagttgc tctctgacca gactctaggt attcaggaga aagtgttcat tgtctcactc    6480
tctcatgtgg caatcaagta gtgccaagca gtgagagggt gaaggtgggt gggtgaggga    6540
cactcacctt gctgagaaag ggcccagcc tgttcgggtg attataaagc agagacagtg      6600
ccaggaaaag tctgacactg gctgagaatc acccggggac caaccatccc gaatgcggat    6660
ccctgacact gggtgaggat ggagcttgga gatctgcatt gttaataagc agcctagcag    6720
agtggtgaag agtccagaca cactacctag gtccaagggt aaccttgagc taattacttt    6780
ttgagcctct gtttcctcat cagtaccatg gggaagaata gtagcacctt gctccaggat    6840
gtttagtgcc ggctaagggc tcagcaggtg ctggtccatc tccaccagcc cccagtggcc    6900
tgggccacct ttgagaaaca gtgatcctaa gggattcagc atttcctaag ttggtgcctc    6960
ccacctgtca cccccacccc accaggctag gagggttgtg attagagggt gcccttgctg    7020
tgacagctga gactagctct tccctgatta ttccttaatg acagctctct ccttccctgc    7080
tttcttgaag tcttggtcct cgttgttgtg ggcacagctt caggggaggc cttggaggaa    7140
tttttgaaag tggaatgagg gaagcagcct gctcaaggga cacttgtttt ctggtgagg     7200 aggccgcatg tatgaatgac gtttgtgggt tagaaagcat gttttgtagt ttttccttgt    7260
ttcttcctga agacatgtca ggtcttgatg agaccgggcc tgggcacagg gcaggcagtc    7320
agcgagtgtg gatgatgacg acagtggtca ccaggtcact gtctagacca ggtcactgtc    7380
tagcgcagtg tcacatggaa agggtatggt cctttaaccc taccctcccc agcacaacta    7440
tcacagatgt cagggaacct ctgctcacag aactgctttc cagggattgt ctttttttc     7500 tttttctttt tctttctttt tttttgaga cagagtctca ctctgtcgcc caggctgaag      7560
tgcagtggtg cgatctcagc tcactgcagc ctccgcctcc tgggttcaag tgattatctt    7620
gctacagcct tctgagtagc tgggattaca ggtgcctgcc accatgtcca gctaattttt    7680
gtatttttat tagagacggg gtttcccat gttggctagg ctggtcttga actcctgacc      7740
tcaggtgatc tgcccacctc agacaggcat gagcaccgca cccagcccca gggagcgtct    7800
tattagtggt tggcaactga atggagacgt gggaattgta aggaactgat tctacttgat    7860
cctgggtccc ctgcttctcc atcttcaccc acccatcagc tcccttctc ctttaaacag      7920 gcacctttgc tctctgctta tccattttg ttgtgcattg ctatttggga gcctaagaaa      7980
cacaacatcc tctgaatgct ccagctgttg tgggtctgaa gggtgagcct gccctctgtc    8040
attggaggct gcagcctgtg gctttttagg tacagggact cccagaactg ctcctccagt    8100
catagcagag ataaatcaca ggagcttaag aggcatggga agaacagagg gaggagatcg    8160
tagcttccct gttcattcac acccaaaaca aaactgtcat actagaaaag gaggtattaa    8220
aagagccacc tgtacagcct cgtatctcat ccagcacact gctgcagatg gaatattatg    8280
atttagcttg agaaaatgca gcaactcttt gttgtggtgc ccctctttga gtaagagtga    8340
attccccatt gccagagtgg atagtgaggg aaaccctggg tccaggcagg agtctgttta    8400
```

```
ggatttatct agtgaggctg agccagagga ggaccttaca gttttttctc ttcaatttct    8460
tttatttatt tatttatttt tgtagagatg gggttttgcc atgttaccca ggctggtctt    8520
gaactcctgg gctcaagcga tctgtctgcc tcagcctccc aaactgttgg gattacaggc    8580
gtgagccgag ccaccatacc cggcccttct cctgcatttc cacctgataa tttctctcat    8640
ttccatagat gatgaaggaa ctaaagccaa gaactttcca aggtcctgca gctctttggg    8700
ggatgtgaag ctgtgctcta tttgtatgga ttttgctggt tcccagaact tccctgtggc    8760
cctggggcct agtctgaggg tactctgagt gaagagggag gagggcccac acctcttctg    8820
caaaggctgc ttttgtaaag ttcacttcag ttcacatctt cctcctggtc agaaagcttc    8880
gggggctctc ctctgctgca ttaagctctt actcctccat caggcaccaa actcctccct    8940
ggcatggccc atcctaccag gtccccacac ttgagccaca tccaattgct cgatattatc    9000
aggataggtt atgttatgtt cccaactcat atgtttactt aagtggttac ctctttccag    9060
aatgagcccc ctcctccaaa ctctgcctgg tgaaatattc ctaacctttg cagcttcaca    9120
tccctcttac ttcttgtgac ctgaggcatc tactcctgac aactgataga ctgtgtcccc    9180
tcctgtcggg tgcattgtcc ttgtcactac cctcctggct tttagctggc tttgcttccc    9240
gctgttgtta ctcctgtact tgtctcatct atcctaaaca gaaggtgctg caggctgggg    9300
agtttgttca tgttgaaatc cctgtgatgg aggtgagcag aggcagtctc tgcctgtgcc    9360
tcttatttgg ggatgaagtt aaagtccctg taggaataat ccaggccata gccggggttg    9420
ctgtcttcag aaagaagggc agccacaggt cttgttaagg ggattgaaat tggctgactt    9480
ggtggaagga acctgcctgc tttgtttaaa aaccacatat agctgagtgt agtggttcac    9540
actctgtaat accagtgctt tgggaggctg aggcaggagg atcacttgag gccaggagtt    9600
tgagactagc ttgggcaaca acgtgagacc ctcatttcta caaaatattt taaaaattag    9660
cctagtatgg tggcgtgcat ctgcagccct agctactgag gaggctgaag tgggagaatt    9720
gcttgaaccc aggagttcaa ggctgcagtg agctatgatt gcaccactgt actccaacgt    9780
aagtgaccag tgagaccctg tctctagaaa taaaaataaa aaaatcaca tatattgtgg    9840
ggtgacttac ttggagacga actttcagca gagcgcacac ctgctatccc tgcccagggt    9900
gtgaagctca gccctgaggg tctctggaca gcgatcactc agcctctgga cagcgatcac    9960
tcagcctctg gacagacagc gatcactcag cctctggaca gcgatcactc agcctctgga   10020
cagcgatcac tcagcctctg gacagcgata actcagcctc tgtccccgtc tgagatgttg   10080
gcagggactg tcagatttgc caggcattgt ttgaagttct tcccagccca gaaacctgca   10140
tgtgtagatt ttggtacact gggtccccca cttggtacta ctgtgtgaaa ccccacttgg   10200
cactgtttta gggggcaggc ttccctcctg tccccttggc cttggccttc cctgggtcc    10260
cgccctcagt ggcacttccc cacctcacac gtctgctctc atggcttagg tctccacttc   10320
taacctcagg agacctggtc ctcagacacc tcccagacag cttccccatt ttatcccata   10380
gacactcaaa gggtgaaatt catggtcttt cccgagactc tcttctccgg tcttccctgt   10440
cttagtcccc acctggctgc cattctagac tgtgttttct ctcctgcgtc aggtcctgcc   10500
cttgacctct tgacccctt tggactctgc cctcacttgc atccatcctg ctgctgtcct   10560
cagctctcct cacctgccac agttgtctct gggggtcact ttccctctct ggtcagtggc   10620
cagactgact tttataaacc tggttcagat cttgtctgtc aagattgtcc tcagggtgat   10680
gtgtgtctcc ttaacatggt gcctgagacc ctgatcatct ccactgcccg ccccacagtg   10740
tgaggccctc actggaacat tgtgccttct gcccttccct cctcctggga aaaccagtct   10800
```

```
ccatcagata ggctcttctc tagaaaacat tcgtgatctc tgagatttgg ttccactttt   10860
gtgcttctgc acctaccatc aaacacccgg attgtatcat ttgtcacatt agatgatttt   10920
tgttttgttt taagacaagg gtgtttctta ctcatctttt tatccccaga gcccagcatg   10980
atctttggtg cataatagat gcaccacaga tgtttgctga ttgaatgaat gagcacactg   11040
acagtttgga gctgccctga ctttcgtggc tatgcgtttt gcccctggg atgtgagtca    11100 cctcaggcca gccccaggca aggccgctgc tgcctccatg gtaactctca aggcctcttg   11160
ttttatggca gtcgtttgat tgacaggcat ctcttggaag cttttggggc aggacttgtg   11220
tccaagtctc caggtcgcct ccagccaccc cctgagtcct ccactgcctt tgtctcacag   11280
gaaagtggaa caaggtcctt gtgctccttt ttccaggtgc ttccagaggc agggctatgc   11340
tcacattcat ggcctctgac agcgaggaag aagtgtgtga tgagcggacg tcctaatgt    11400 cggctgagag ccccacgccg cgctcctgcc aggagggcag gcagggccca gaggatggag   11460
agaacactgc ccagtgggta ggtcccacca gcagctgggg gccttcaaac aggtccctgc   11520
ggctactgta ccttacagat gaaaaccaga cattcattcc ctgatgcggg agggagaagg   11580
gaagtaatga tgaggattgg ccgaaaaggt gggtggctgg ccatgatgga ccttccatct   11640
gcagggtttc ataggactgc gcattcacag ccagagatgg acttggcagt gggctgaagg   11700
acgctgtcca ctctgccacc ttgggtttac ctctctcatg caggtcactg tttccactgt   11760
aataggagag tttgtttgga tgcctgggtg ctaggacagg taacacagaa gcttaggatg   11820
gtagcagggg aagcattttt tggcagatgg ccagacatgg taagtgtgag aggagtctgc   11880
ctgatacacg attgactttt gagctgggga tatttgggct tcactgtgat cattcagccc   11940
ccaggggagg agattgtaac gttagaaaga gtaggatatc gttgggagag ccacttagtt   12000
gtgtcctttc tctcccgatc agggcagaac atctgaattt gcctgaaccc tgttctctgt   12060
tttgcccatt atagaattaa aaaatgtctc tgtgtggact gttttcttgc agccagtctt   12120
aatcctgctt gctgaaattt gagctcactt ctccatgttc tccttgagaa cggaaccatc   12180
gtccctaagc cctgagtgaa atcacaccag cttaaggcca ctgctctgcc actcctcagc   12240
cttttcttgt ttgttatctc cgggaagttt tgtacacttt ggttgtttca gtttctgttc   12300
atgagtagtc ttcttcttg gctgaacgtc tagattggga ctctctctgc agagaaccgg   12360
tactgaagca actgtcattt tcagtttttg tttcatttgg cttttttcttt agctgttcac   12420 ctcattagca aggcagccca tgaccttgac ttgccacagt tccaaaacac aaattcttac   12480
agatcggttt gtgctagtgt ctggcaggtg tcctgccctc cctcgttacc tcctcatttg   12540
tgcctgccca ccttcccaga gcctgcgtct tctcagatgc ttaacacctg tttagcctct   12600
ctagttcaga gctacaaatt tacatgcttg attctgtggg gcagaaagtt caaagtaatt   12660
tcttcctctg caaattccca gtatcttagt cacacgcaaa gagagtgtcc ctgtgcactg   12720
actcctctag ctagtgattt gtcagccaaa aatgtttatt tatctcctgg cctgtttcct   12780
cccatatcag tatggccaca tgaacagaat tgagtgacct cctgagtccc tgtattagga   12840
aggggaaaga tcttttgatt cattaaccat taagttgatt cattaaccat taagtcttgg   12900
gcctgcagac catagcaacc ttccttcctt catttatggt gcttcatcca gctccaaatc   12960
ttctctactt tgtcctcaca aacttttcat atgccctagt agctcataga ctgctcctta   13020
tatctggaaa gcaacattca aacttctcat ttctggttcc aaaaatccgt gcattacatg   13080
gataggctgc cgtgggggac attctgcggc cctcacgatg tggtttccca cagagaagcc   13140
```

-continued

```
aggagaacga ggaggacggt gaggaggacc ctgaccgcta tgtctgtagt ggggttcccg   13200
ggcggccgcc aggcctggag gaagagctga ccctcaaata cggagcgaag cacgtgatca   13260
tgctgtttgt gcctgtcact ctgtgcatga tcgtggtggt agccaccatc aagtctgtgc   13320
gcttctacac agagaagaat ggacagctgt gagttggggg ctgggggga gcagggtggg    13380 gtgagggctg agttgccagg gggtgggggg cgcagcagcc tgtgttggtc actgtacctg   13440
cagctccaca ccagcagcgg taaagagcag ggatgaagaa ccgcccaggt tcatggcctg   13500
gctcactgcc tcctggattg tgacctactt gggcatgctt ttaacatccc tatgcctcag   13560
cttccttgtt cgtataatgg gttgataacg cagttactgg gagaattaag tgagttaata   13620
tgagtgaagg gcttagaaga gtgtctactg cacgtgagtg ctcaggcaag ctggatcctg   13680
ctgcagaaag caagctcttg atcctgggca tggctgtgcc actgatccct gtgtgactgc   13740
aaacaaatca cttcctctct gagtctctgc ttccctgaat gtgaaacaag gtggttggac   13800
cagatatttc tcagctcact tccagccttg tgaggaagac ttataaagcc tttcgtttat   13860
tttagtaaaa tacatgcaga ggcagcagcg tagaaaaatg agaagcttcc tccacttctt   13920
ccccctcccc tttctgtggt cctcactgct aagcaccttc tgtaaacttt ttttttttt    13980 tttaaagtta gggattttg tttcatttcg tgtgtgttgg ttttttttgt tgttgttgtt    14040
tcttttaaag aaaggaataa ggccaggtgt ggtgtctcat gcctgtaatc ccagcacttt   14100
gggagactga ggtgagagga ttatttgagc ccaggagttt gagaccagcc tgggaaatgt   14160
ggcgagaccc tgtctgtaca aaaaatgcaa aaattagcca ggtgtggtgg tacatgcctg   14220
tagtctcagc tacttgggag actgaggtgg aagaacacct gagcccagaa gtcgaggctg   14280
cagtgagcca tgattgcgcc actgcactgc agcctcagca acagagtgag accctgtctc   14340 aaaattttt taaaaaatta aaaagaagt agagtcccat cctcagaaag cttatagtgt     14400 gtggggatt cagcgcagaa caggtgaaag catggagaga atgcagccag cggtttgttt    14460
gcagcagtcc aggctgggaa gagtgaggtt tgagtgaatt gcttcctgtg tctgcttcct   14520
gagcttatga gctgcaagga cagcagttgc ttcagcggat gggggtcggg tagtagcagg   14580
tggaggagtg ctgggctggg tggagctggt ggagaggtgt gggtgggtgg gggaatgaga   14640
actggatggg tgagagaagt gcctagggag cctttaatcc ctgtgggggt ggggaaagca   14700
gcagggaggt catctagccc tcgtcctcac tgctgcactg ggcccagttg gcaggctgag   14760
agccacaggt ctgtggtcag ggtgccagga aatgagctgg aggacaggaa ctgctcatgg   14820
ggatggtgcc cgcactccat cagggcagca tgtgggcagc atgggcatcc caggcacctc   14880
ccctagcagg tccagaatca ctcaaggtgg ggagcctcga ggagcagtca gggccgggag   14940
catcagccct tgccttctc cctcagcatc tacacgccat tcactgagga cacaccctcg    15000
gtgggccagc gcctcctcaa ctccgtgctg aacaccctca tcatgatcag cgtcatcgtg   15060
gttatgacca tcttcttggt ggtgctctac aagtaccgct gctacaaggt gaggccctgg   15120
ccctgccctc cagccacgct tctctccgtc tgccccacac catggcggca gggcccgtga   15180
aacagccgcc tttagaaaaa cacaaattag aggaaaatag acccagattt tttgtactcc   15240
tccccacccc atcctgtctc ccaccgtgga tgacctaata ctgttgtctt ttattttat    15300 ttatttcttt tttcttgaaa catggtctca ctccattgcc caggctggag tgcagtggtg   15360
cgatcatgac tcactgcagc ctcaacctcc tgggctcaag ttctcccacc cagcccctca   15420
agtagctagg actacaggtt tgcaccacca tacctggcta attaaaaaat ttttttttgt   15480
gcaggctaga tctcacagtg ttgcccaggc tggtctcaaa ctcctggact caagtgatct   15540
```

-continued

```
cccaccttgg cctcccaaag ttctgggatt acatgtgtga gccattgcat ccagcctgtt    15600
gtcttttaaa tttacacatt atcccacttg agttcctcat tgcagtgttc caagcatcat    15660
ttctcatatt tcaaagttaa ttttgttttg cttctctttc tgaagttcta ttttaggctc    15720
ccctcacccc gatacttccc ctgaagattt attttagtt ttccttttcc ttttcgggca     15780
aggatgtgca gaggccatgc tgaggtcttg cagccctggg agacttttgg gttgtagctg    15840
cctatagctg ccgagtagcc cagggagta gtggaagggc agatcccatc tggccagaat     15900
catgggcact gcctgtcccc aaagatgcca taagctttta gacagcggct tcaggctttt    15960
ctcccaggta aggggttgaa ccctaacga tggaaaggaa attaagctgg gcattaccta     16020
ttttaaaact gtttacacac aggtgcctca cagcattttt tgttcaggcc gctgccatcc    16080
atggagcagg tagatagaag tgcagagtgc ccaggctaga gggatgggac agggacagtg    16140
cagggaggga gctgagcccc cttccagcgg gggcagcaga ggggaaagcc atgggagggg    16200
ctgcaggatg tgtcctgagc tgaagcttat caacaagtaa tgagtaccag ctgggcattg    16260
tggtgcacgc ctgtggtccc aactacttgg gagactgagg caggaggatc gcctgacccc    16320
aggagttcaa gtctagcctg gcaatgtaa gaccctgtct ctaaaaaaat aataataaaa      16380
taagtaacaa ttacctgtgt aactgtgacg aggcagggtt tgaacattgc cgctgggagg    16440
ttggcagatg gtgggaagca gggtggaggg ctgctggttt ggagcagagg atacagattg    16500 catgggtca agctagaaat tgcgtggcag atgtgaagag ctggcccac tgcgggcagt      16560 aggtgtctgg tggccagtcc cagaggctgt gaagagggc tcagccatct gtctagtagg     16620
gcttccttgg aggttccacg atacaggcag atggtggtgg cccgggcagc caggtggtgg    16680
ctgggatgaa gagggttggc aggtcccaga ggcagcccct tcccttttg gctgtgtgtg      16740 cagcagggcc gtggaggctg cttttagtcc aggtagacca gggccacgct gaggtcccag    16800
tgggctgagc tggtgactga tgagttggtc ctcagggtg aggctggtgg gaagtgatgt      16860
cactgtcccg ccgatggcca gctaagggac tgggttagga tcagcccct cttgtccttc      16920 actctcccat ccttggccag gagaagagga acaggtcttt ctgaggacct gcttgtagac    16980
ctttgggtag gaggggactt cccaggttct ctgttgaggc cactctatct aaaatagcac    17040
cccagtgagt ctcctatcac tgtatcctaa cattattttc tccatggccc tcatcattac    17100
ctgctgatat actgtatgtt tgtctatatg tcatctaaca cccctcacac tggaacacaa    17160
tgcccgtggg cagagacttt gctagccttg gttccagagc ctagaacagt gcctggcaag    17220
taggagacac ccagcattac cttctaagt gaaccagtag agatggggg agaccgcaag       17280 gctatgccgg cagacctgag ggagtcctgt ctgcatgcgc tgcaggatga cctgagggga    17340
actccttgga cttctgtgcc ctctttatct gtaaggtggc cacctgatcc cttccagcgt    17400
aggcatgaag tagcctaatg aagagcattc aggcttgggt atcagtctca ggatcctggg    17460
ggccttagaa tttgtggcgc ttggggacac cttgtgatcg tgcaatttct gttgtctagt    17520
tcatccatgg ctggttgatc atgtcttcac tgatgctgct gttcctcttc acctatatct    17580
accttgggta agtgacagat aagcagcagg gtccctggga gccctctcc atgtggcaca      17640 agtggacatg ggcatgagga cctgggcggg gaaagatgac catcgagctc cagtcttccc    17700
cagtgccagc cgttttggga acccaggcct ccgtcgccct ctctcatggc cttgacacag    17760
gggagtggaa gtgggctgc atggtggacc acatgtttct gtctcgttcc tgatttaaaa     17820
tgaacccttc atggagaagg ctctctgtga accccagggg gatagaaacc ccccaaaatt    17880
```

-continued

```
tacattctga ttttaggct aggcctgggt actttctggt tgtgggaaa aattatctgt    17940
tctatcgccc cttgatttgg gatatcagcc tgacccaggg gcccaaagag actgggagga    18000
caagagaaaa cactttccca aggacctttc catgtgcaca gggtcttcca ggtcatgccc    18060
atgcacattt ctgtgatctg ttccaagcat ccccaccttg ttttagaaaa tgctgcaaat    18120
ggtaaattgt aaggacagtg aaggtcgggg aaggaaatgt tagtaaagag gccaggttg     18180
ggactgaatg gtggtaaact gctaggctgt aatgcctcca ctgagtccca gtcacaggct    18240
ccaccttggt cctgcaggga agtgctcaag acctacaatg tggccatgga ctaccccacc    18300
ctcttgctga ctgtctggaa cttcggggca gtgggcatgg tgtgcatcca ctggaagggc    18360
cctctggtgc tgcagcaggc ctacctcatc atgatcagtg cgctcatggc cctagtgttc    18420
atcaagtacc tcccagagtg gtccgcgtgg gtcatcctgg gcgccatctc tgtgtatggt    18480
aggtgggcag caaggctggt gggggcagtg ggggcgatgt ccagggccaa atcgtcccca    18540
gtgctgcaca aggagggcag gtgctgaagg gcttgcatcc cttctgcag  aggcctgggt    18600
gggatccctc ctgagagagt cgcctttgta aaacagaggg gggtccacta tttctggaac    18660
actcctggtg gtctagataa aacgcagtag tcactgagct cctcatttac ttttttttt    18720
tttgagatgg agtcttgctc tgtcgcccag gctgagtgt agtggcgcca tcttggctga    18780
ctgcaacctc cgcctcccgg gttcaagtga ttctcctgcc tcagcctcct gagtagatag    18840
gattataggc atgtgccacc acgctgggct aattttgta tttttagtag agatggggtt    18900
tcaccatgtt ggccaggctg atctcgaact cctgaccttg tgatcggccc gcctcagcct    18960
cccaaagtac tgggattaca ggcatgagcc actacaccca gcctcatttt ccattattac    19020
tgctatgctg attgagcaag tgcactgtta agcactggac acgctgtaag tgatttgttc    19080
atcaagacag tcctttgggt accatgcata tacataaccc caaatgttag ctgctatttg    19140
atattagcat gattatcatt gccagtattg ttacttccat tttaaggtta aagaattgga    19200
ggctcagaga agtgggactc cccagcctgg ccaccgcgtc tcgggtgcac agctcctcca    19260
tgcttgcagt tgcctgcgag gccctactct ggctcacacc agggcctgct ctaagttgtg    19320
actggagaat gagaatttgg gatgccagcc cagaggcaag gcatgctctg agagctccac    19380
ccggggctcc tgtgctacag ggcaggctct tcttcagggg gctgcccggg gatagtttga    19440
caaggatgtc tctgtcttcc tagatctcgt ggctgtgctg tgtcccaaag gcctctgag     19500
aatgctggta gaaactgccc aggagagaaa tgagcccata ttccctgccc tgatatactc    19560
atgtgagtga gccccccgtg cctctgcctg actcggggtc agcaggcagc ctgtgggggg    19620
acaggggcct gcttcctggc cgtggctttc agagttgact gggcgatccc aggagggtct    19680
ccactttcag aagccaggga gggcagtatc ttgttattac acagtaagaa gcttagaaag    19740
ttaggacagg aagcaggcat ctgctgggat gtgctgcagt ccctgacttc atcccgtcca    19800
tcctccagcg gcatgctgcg gtgcaggttg cattcctgtg atcccgcagc caccccctcag    19860
ctctccaggc tcttgagaag ggactttgga gagggattct tcaggcagg gggtcgggga    19920
gcaaggagct tctgggcttc cttgacagca gcgtggctga ttggcattaa tcctaactga    19980
agggaaggca cacgggatgg cccctggcct cgggtcaat gtgtagagat ttggacttac     20040
acatgcagtc aacaaaggca catcaagtcc ccattttgtg acaggcactg tgctaggcat    20100
tgggggaccc agcaggaaag aagaccacag ggtcccaggc tcatggagc tcacggccct     20160
gtgattgtga tgccctcggt ctgttgatgg cggggcttaa atagcctgaa tttctggagc    20220
tctggcgtct gcaaggtggc ctgggaaaga gtttatggaa cagctacaga gttctaggta    20280
```

```
ccttcatgca gttgaggatt cgagcccgta gaggagaatc gcctgcagcg tggccccacg    20340
ggaaagcaca ttccaggcgc attccgagga tgagcggaga ccatgtatgg aaaggtagtg    20400
ccaggactgt catgagtgtc ccagggctcg ggggattcac ccgtgaactg tgaggtcttg    20460
gctctgatag acctggttct tatgctttag gaggggagac aaacagtaac agaatagaca    20520
aatgcaagag agagtgactc tggacccctc ccacaacggc ctcctaacaa tggagcatga    20580
gcagatacct gcaggatgga gggtcctgtg caggctttct gggacgcaga ctggccacct    20640
cccccaggcc ctgcaggcag ccactgttag caccgcctga gatgtgaacc ttttctcctc    20700
ccccagctgc catggtgtgg acggttggca tggcgaagct ggaccccctcc tctcagggtg    20760 ccctccagct cccctacgac ccggagatgg gtgagtatct tggggagcta acagcctctc    20820
atcactgggg ggcagctccc tacctgcacc cagctctgct cggcctggct tccctgagag    20880
gcatgagttc aggaggggca gagggaaagg tccgttgaaa accagccgga cacatgcggc    20940
ttgaagattc agcaagtgtt ggaccctcgg tcctctgcca gcctctgttg catcgttctg    21000
ctgggcgtgg gtgggtggag tgggggaagc cctggtgtca ggtgctggtg ctcaggggga    21060
ccccttcttg gagctttgtt ccctggtaac actctgacca gctgttgttt ctctctcttg    21120
ttgtcccctc ctcacggtga tgacggacat cttctcttcc tggacaccca gaagaagact    21180
cctatgacag ttttggggag ccttcatacc ccgaagtctt tgagcctccc ttgactggct    21240
acccagggga ggagctggag gaagaggagg aaagtaaggt gcccatgttc acacggcctg    21300
cttcagccta cggcgggagc ggagacagag ggtggaggct ccctgcagcc tgggtggagg    21360
agggcatgag gggaggggcc ccttttccca tcagaggcat ctctgtgaaa gtagaagatg    21420
cctgcagcgc tggggtcttc tcagcaggcc ccatgtagtt gtccggcatg tattgagtat    21480
gggccacgtg cccgtgctgt gctgggtgag gcccagccct ggtgggaccc acaggctaag    21540
gagacacggg cagtaatcac atagactgag aagccaagga ctatgaaggg ggccatgggg    21600
ttggggaggg gcggcaggag agcatgccac ggggcttctt gacctggttg gcaggggtga    21660
gagaaagtca gctgaggaag taactgctga gctgagctct gaaggttgag tcacagcagt    21720
cactagagga gaggagcaca gggtggggag catttcctga cagacagact caggaatcag    21780
aggaagccgg ggcgggatgc agagagcaga agtgtgggag agccttgcaa acaggcctgg    21840
agacatgcga agataggagt tcatcctggc gtcagtacac ggtgcctgcc taacacccaa    21900
tgccagccca ctgctgcgtg ccaggcagca ccctggagca gggagatgct gcactgtcgt    21960
aacagcccct gccttgagag gtgccttacg ggagcagcct ggtgacagtg gcttggcata    22020
caggactcca gtgacacggg aggggcaagc tagggaaaga tcactctgcg gtgggtctgg    22080
aaggaggagc aggtgcgcac cctccaggca ggcttggggg aggtatttat tccaaggcca    22140
actggtgtgc tgcagaccag gagttagcac agatcccacg gggcccgcag gactggcctc    22200
cctccagaca ccagccacaa gctctagagg gtctagatgc cacttgtgct tctgaccggc    22260
tgcaaattta gggctcccat gacccccttg ggttcaataa cttgctagaa tgactcacag    22320
aactcaggaa agcactacac ttaaaattgc agtttgtttt tgttgtcgt tttgttttgg    22380 agacagggtc tcgctctgtt gcccaggctg gagtgcagta gcacgattgt ggctcactgc    22440
aaccttgact tcctgggctc aagtgatcct cccaccttgg cctcctgagt agctgggatt    22500
acaggcacgt gctaccacac ctggctcatt tatattttta gtagagacaa ggttttgact    22560
tgttgcccgg gctggtttcg aactcctggg ctcaagtgat ccacctgcct tggccttcca    22620
```

```
aagtactggg attataggtc tgagccacag cacccggcca aaattagttt tattataaga   22680
gatgcaactc aggaccagcc aaatgaagag acagtgaaga agtaatgctg atggatcaca   22740
cctggtgggg gaaggaggac agctggggcc aggagcagga gggacacctg cagggctgga   22800
agggcagggg aggtgggcct ccatggtttg tgtttattgc ataaccattt ttattgtcta   22860
cagtgagcaa agttatccta taaacaagtg tcagggacca ttgcactaaa gaaaacaaac   22920
gagagcattt tggaagctct aatttcctga tcagtaatgg gtagactaat tcccagttat   22980
atttacctgt tgtaaggtga aaggttcttc agaggacctc tgtcttggtg ttatatgggc   23040
ttttgaatgt actgaaatta aattccctaa aaatctgtga ttcagacttc atactaaatt   23100
gtacagcagt gcccagccca aggccttgca tttctatttg ttgttttctt tactctctaa   23160
gtgcccaaca ctggttttac ctgagtttca gaactgcccg cttttctctg cccaggttgt   23220
aagtcaccca gtccacaggt gtcccctgct ttcccactgg ccactgattt ggggaggcag   23280
ctgtccatgt ccccagtcca catcttagct tctagaggcc aggtggggtg ggctgggctg   23340
ggcaagagca gctgggcctt ctgggccaga gtttctcttc tttttccatt ctgtgcacgc   23400
ctcttcagta cgggttactg tctctcctca cacaggggc gtgaagcttg gcctcgggga   23460
cttcatcttc tacagtgtgc tggtgggcaa ggcggctgcc acgggcagcg gggactggaa   23520
taccacgctg gcctgcttcg tggccatcct cattgtgagt ggctggggat gcgtccagct   23580
gcctcgtggt gggggccccc agggtcctca ttgtggtggg ggcaggtctc aggatcccta   23640 gggattttc atttcttctc ttccctctga gggacaagag cagggagcgg ggctggaagg   23700
gtcagcttga gaccaaggct cacaggaggt gtgctcgccc ctaggtgggc tccagcctgt   23760
ggaggacagt gcaggggagg gtgaggagtg taccggcccc agcgtggctg agcacacagc   23820
ctccaggccg aggacccagc tgacagcttt gcgcagtgat gataccctcg aggtggttgt   23880
gatgacatca gatttgcaga aaagaaaatt gcttaagggc cttgcccatg ggcgcaaagc   23940
tagtgaggac catgttttcc ccctcctcca tgccattggg acaccacagg gtctgaatct   24000
ggggcactag gggtggcccc gttactgtga accacagcag tgaaatgtgg aggccctgta   24060
gtcagttaac gtgaccagat acacataatg gggagacgtc ctgccgtgac ttcatctcag   24120
agatttcgct gtcacgttag aggaggagga gcgtctgagc cgtgcgcttg gcatctgccc   24180
cttagtgaaa accctgggca tggcatgatt aaggttgatg ctccagtgtc cagaaggttt   24240 tcttttgcc cacaagtata tcagggatgg gatggtggac ccaggctcct ccaccaccag   24300
actgccttac ctgagccctg ctggccccaa agatatagaa ggcaccctgg ttccctgtgc   24360
tcacctggac cactgcctgc atcagctggg tcaggggagg atgggcagcc cccacacctg   24420
cttcccaggg gcaggttgcc tggcggctct gattcccttg gtgccagctg ctgagaacct   24480
tactgccatt tcagttgagc ccacctagct ctcatataaa tacatgttcc ctgagggcat   24540
cttaccatcc catgtgacca ctccagccag acagggagg cagcacggcc tcggggcaca   24600
gcactgctcc aggagtcagg aggcctgcct tctggttcac tcactaacag gtgaggtgat   24660
ctaatggggg tgagaacttc tgcccttaac acctcaagag ctgttgcagg accagggaag   24720
ataatgtggg gtctagcgcc gttatccgac tggtcctcga acaagctcct gtgcccaggg   24780
actagaccat gactcacagc tcctgtccac accagggatc accacgctca ccctccctc   24840 catgtcctgc agggcttgtg tctgacccctc tgctgcttg ctgtgttcaa gaaggcgctg   24900
cccgccctcc ccatctccat cacgttcggg ctcatctttt acttctccac ggacaacctg   24960
gtgcggccgt tcatggacac cctggcctcc catcagctct acatctgagg gacatggtgt   25020
```

-continued

```
gccacaggct gcaagctgca gggaattttc attggatgca gttgtatagt tttacactct   25080
agtgccatat attttttaaga cttttctttc cttaaaaaat aaagtacgtg tttacttggt   25140
gaggaggagg cagaaccagc tctttggtgc cagctgtttc atcaccagac tttggctccc   25200
gctttgggga gcgcctcgct tcacggacag gaagcacagc aggtttatcc agatgaactg   25260
agaaggtcag attagggcgg ggagaagagc atccggcatg agggctgaga tgcgcaaaga   25320
gtgtgctcgg gagtggcccc tggcacctgg gtgctctggc tggagaggaa aagccagttc   25380
cctacgagga gtgttcccaa tgctttgtcc atgatgtcct tgttatttta ttgcctttag   25440
aaactgagtc ctgttcttgt tacggcagtc acactgctgg gaagtggctt aatagtaata   25500
tcaataaata gatgagtcct gttagaatct tggagtttgg tccgttgtaa atgttgaccc   25560
ctctccctgc atcttgggca cccctgggat aacttgtgct gtgagcccag gatggaggca   25620
gtttgccctg tttgaaggaa cttttaatga tctcgcctct ctgcacacat ttctttaact   25680
agaaagtttc ctaagcaaag gagttaggag agcagggtgg cctgacatct gccagccctg   25740
agctgtaagg ctgtggatgc tgagcaggtc cctggactca gttgtgcacg gtggcacaga   25800
cactgccagg tggttgccaa acatccagt ggttccttca gcaagtgttc accctctgca   25860
gaagcctgtg agggcctgag ctcagaaacc actctccttt ccttctctgg ctttggccct   25920
gggcactgtg gtgggagagt ggacagtttg gctttgcctt ctctgtacat caatcatggg   25980
ttgcaaagag aatctcagaa gtgcctcttc ctgagcacag tggctcacac ctgtaatccc   26040
aatacttcgg gaggtcgagt cggaaggatc acttgagccc aggagtttga ccagccgg    26100
ggcaacatag tgagactttg tacaaaaaaa aatttaaaaa ttagccaagc atggtggcat   26160
gcatctgtag tctcagctac tctggaggct gaggtgggag gatcacttaa gcccaggagg   26220
ctgaggctgc aatgagccga gatcaagcag gtgttaggta tatcagacag ctgagaagac   26280
gcaagtgtgc cctggggttc aaactggtac ccctgtctcc ctgttccagg aataacatga   26340
gtgccgggac aatgcatctt tattatgaga ggaatgagaa ttgtgtatct tgacatttga   26400
caggagcttg cttccccca ggctgtttga ggaagggcag aggaaaatgt ggtgccctaa   26460
gaaggaagga cagaggaggc cgaacactgg cgggtggaat cccactgatt agtagtgcag   26520
gtcagagacc tgggatgggg ggcattgccg tcatggaagc cacagcgggg agcgggtaaa   26580
gcagacaggg atggtccctg atggtgacaa ctcgcaagag gttaagggga aagaaaaact   26640
gaaaagctta ttcaatttgg caattatggc agtgtttatc ttcagaagag cagttttagg   26700
gtggggtttc caaagatggg attggacata tattttgaat cattaagctt gaggtctttc   26760
aaaggcctgg ccaagggttg ctgggtggag accacattca gaggtaaagg cagaaattgg   26820
gggcccttaa gtagacagcg agggaggaag aaatgaaggg gcctggtgat ggttagggtg   26880
aagtgttaag actgagaaaa caaggacatg tgagaagacg agggaagagc attggagaga   26940
acaaagacac tggaggagat gctacttgga ggtccccaga gagcagggag acaaatgaac   27000
ccagaacaca aatggcaaag aagaaaaatg agagaatttg taaagacag cattcgaaca   27060
tgccgaacaa gagcagggta ctggtgttca aacacctgta tctcccccgt gtaacccgtc   27120
aactaatatc tttccatatt tgctccagat ttgtctttga aaataaaacc cacgttctga   27180
agtcctgttt gtatgtggcc ccagtcctgt tgcctccgcc tcctgtcctg aagtcgattt   27240
ctgcccttct catctatggt tagttttgtt ttgtatgttg gcatgttttc ttaactttac   27300
agaaatggta tcatactgta catatttgat aattttttaa aatattgcat tctggaggca   27360
```

```
tgtataaatg tagctccagt tcatttattt tatttatttt ttgagatgga gttttgctct   27420
tgtcacccag gctagagtgc aatggcgtga tgttggctca ctgcaacctc tgcctcctgg   27480
gttcaagcaa ttctcctgtc tcaatttcct gagtagctgg gattacagtt gcccgccacc   27540
atgcctggct aattttgtat tttagtagag acggggtttc accacgttag ccaggctggt   27600
ctcaaactcc tgactgcagg tgatccacgc accttggcct ccaaaagtgc tgggattaca   27660
ggcgtgagcc accgtgccca gcccagttat tttaactatt gtatagtgtt ccattgtatg   27720
agttctactg tttatatgct attgatcgac ctgtaggggt tttgcagtgt ttctgtatta   27780
cagctgtgct gcagtgagca tcccatcaca ttgtgtggat ttgaggaagt attggaattc   27840
ccccaattga ctggacattc ccaattaccc tccaagtatg tgtctgttta tccttccatc   27900
cgcaatctga gagttcccca actctataat acttggtgtc atcagacttt tcatcttgtc   27960
tgattggatg ggtgtcattt cctttaggtt ttataattat cttttcatat gtgtattggc   28020
tgtacaaggt tccttctctg ttcattatta ttaattttt tagacagagt ctcgcgctgt   28080
cgcccaggct ggagtgcagc agcgtgatct tggctcactg caagctccgc ctcccgggtt   28140
catgccattc tcctgcctca gcctcctgag tagctgggat tacaggtgcc tgccatcacg   28200
cccggctagt tttttttgtat tttgagtaga tgggggttt accgtgtta gccaggaggg   28260
tctcgatctc ctgacctcgt gatccacccg cctcggcctc ccaaagtgct gggattacag   28320
gtgtgagtca ctgcgcccag cccaagtttc cttctctgtt acttgttcat atcctctgcc   28380
cattttttcac ttggatttt tgtcttacgg atatttaagc ctcttaaaat atatattctg   28440
gagagatgct aatctttgat taattatatg cattgcaaat gtctggtaca ttgtggcttg   28500
cctctcttcc ctgcctttag gagtgttttg ctggacccaa gtaattttta aatgttaatg   28560
ttattaaatc tatcagtttt ttgcttgtat ggcttatgcc attgaatctt gttttaagag   28620
atccttccct accctcaagg ttttctaaat tttatttttc ataataagat ttttagttca   28680
tctgaaatgt attttttatga ttgtatttag tagggaccta attttgtttt tctttgtaac   28740
caggtgtccc agcactgttt actgaacagt ctctcctttc tcgctggtct gtagaactct   28800
cctgacatat accaagtttc cataagtggg tggatgggtt cctgagctct ctactgttaa   28860
tagaacttgc tctctcgcag gccaatgcct caccaggtga ttgaagcaga gaaacttagg   28920
tggtgaaagg agaagatggg gcctgtcctg agagtttctg ttcctgagat gctagaggca   28980
gagggtatgt aaatctgaag ttacactgga tctcctaaaa cagtataaag ctacagaagt   29040
ataatagtgt ggaatggtgg tgggagtcag taagggttag gtcactgcag tggtttaaac   29100
aagatgggct agaatccttt cacaggcaca ggcagcttgg agagggtgca atagtgcatg   29160
gtatcagggg tcagatgcct cttttttcctt tgagatcagt aagtggcttt cacctcatga   29220
cctaggctgg ctgctgtgtg ctagccgtca agtcacactc catccagcat gaaaggaggt   29280
tagaaaaggg tgcatttcct cttcttaaaa acatgtctca aagttgcaca cagcactttt   29340
gcctatattc aattggccat tagtcccacg gccatacctg tctgagactg agagactggg   29400
aaatgtcttt atttcaagtg gccatatatc cacctaaaca agataaggga tacgtggtta   29460
tggcgtgtct tttggtttac caatgcagat aatgaagtta ccaaaacaat gagaaaatgg   29520
ggtcgtgagg gatcatgtga atcacaagct gatgtcttca aagacggtgg aaatgggccc   29580
cgggaggcag cagatgacag cagtggggat taaggtagac ctccatcctg gggttaaaat   29640
gaggggaagg tgatggagct ggaccagcag tcagaatggt cagtggttag gagaccctct   29700
gccccccacc gctgccacca ttggctctct acagaatgcc tgcgagtggc ttagagtgac   29760
```

```
caaggatgag gtgcagatcc atgtgcaccc ccctgccccc tctgtggaca attttcatgc    29820
ctgacagcac agtctatgtg gattgcaagc cgatgaaact atgcaaagta gaagcatgcc    29880
tgcagtttgt gattcggtga tgtgttttat gcttatgtga gtcgaatggg gcggcagggt    29940
cctgtggtca cccgctgaga aggaagggtc ctgtaaccac tgcctttctt tcagctactt    30000
gagaaaggtg ttgtgaggga ccgtggattt tgggacagct ttgaatggtg gtagggagga    30060
agggtccggt ctgagtgaat ggccagaaag ctgtggggaa gcttttagga cattggccaa    30120
gagctccctg aaggcagcca gggagatact tgtcagtaca tgtgactaat ggccaactga    30180
atataagcag aagtgctgtg ttgctgtgtg caacactgga caccttagga aggacctcga    30240
gacagtggtt gtggactctg tagagagtaa cagtgacagt agcaaaccct acccagtgc     30300 caaccttgtg ctaggctcgc actaaatgag tttaccttca attctcgtaa caataggagg    30360
taactactat tctaatttcc attttataga tgaggaaact aaggcacaga gatcactgac    30420
ttgcccaaaa tcaagcaggg agtagttagt atataagccc acggtatgtg gtttgtagaa    30480
taggtgctct tgactagcag aaataggtcc tccctgcagt gtgtaattga taacaagcat    30540
gggctgccat cttcctgtcg aggccactca aaacacccaa caggctacgc acggtggctc    30600
acacctgtaa tcccagcact gtgggaggcc gaggtgggcg ggtcacctga ggtcaggagt    30660
tcgagaccag cctggccgac atggtgaaac tccgtctcta ctaacagtac aaaaattagc    30720
tgggcgtggt ggcgggcacc tgtaatccca gctactcagg aggctgagac agaagaatca    30780
cttgaaccag ggaggcagag gttgcagtga cacaagatca cgccattgca ctccagcctg    30840
tgtgacaaaa gcgaaactgt ctcaaaaaaa aaaaaaaaa aagtatgatt ttataatccc     30900
agcaccttgg gaggctgagt cgtgagaatc acttgagccc aggagtttaa gaccaatcta    30960
ggcaacatgg caagaccca tctctgccaa aaataaaaaa tagtctaatt ttagctattc      31020
atgtgtgtgt gaagtggtgt ctcttcgtgg ctttgatctg catttcccta atgctgacta    31080
atgacgttgg gcacctgttc atgtgcttac tggtcagata tctttctttt gttacatttt    31140
attaagtttt aaaatttaaa gtcaaagatt tccctatgag aatgacttt aaaatgacca     31200 aaaagggaa gataacatta attcttgaag agaaggcctc tgagaaaaat acagttgtag      31260
caagctgcta ctttgcaaat gacccatgca ttttaatttt cccctaagga aggccaagga    31320
agagtcttat cacctcaggg caggagatgt agggacttgg gtcatttaat aagagtggta    31380
ggtttgaaaa ctcaaaccca gaagactcct tagagtttct cccaggaggt agggaagggg    31440
ccgcatccat ggagagagga ggatgtgact tagagcagtg gtccccaatc tttagggacc    31500
agggactggt gtcatggtag acagtttttc cacagatagg ggttgggggg atgatttgga    31560
gctgaaactg ctccacctca ggtcatcagg cattagattc tcatgtggag tgtgccactt    31620
agatccttgg cgtgcacagt tcacaatggg gttcgaggtc ctatgagaat ccgatgccac    31680
tgatttgaca ggaggcggag ctcaggtggt aatgctcatc tccaccgctt accacctgct    31740
gtgcagcctg gttcctaata ggctatagac tggtactggt ccatggcctg ggggttgggg    31800
acccctgatt tagaggaagt aagggcatgg cttaccgtgg gccctgggt gttctgggaa      31860 tggggaggat ggagagaaga gaggaggtag ggaagacctc cccttgctcc ccatttggga    31920
tttggggaga aagtcaggtc tcaggctcaa cagtacctga tcctgtacca tcttccaaag    31980
ggaagtcagt ggggttggaa ggtaggcagg ggttatcttc tctgagccac ggcacaagac    32040
agaagtttcc caccattcct gaggggggcag gtggtaggtc cccaagcaga gagccagcag   32100
```

```
tccctctctg aggcctgcaa tggaatgggg tggggtgtcc actgagccaa gggtctgtca    32160
gtgagagctg gggaggctgg gctggcttgc aagcacctgt tataaccaaa ccaggaaatc    32220
aggttccgag tcttgccagc aagggcctac agctgccagc agagatggac agccaggaga    32280
ccccaattgg ccacccagag ccaccctcct ctgcctaccc cacccctcag tactccagag    32340
cctactcgga ggggaacaga aacctgagag gctgaacaca cacacatgga gaaacaaacg    32400
tagtaaaata tttggggaat caggaagaat tatttgtact attcctgcaa cctttctata    32460
ggcttgaaat tatcaaaata aattttttaaa aattgtaata acattctcat actaaaacac    32520 tgagttttt tctttcattt tttgattttt tcttttttgac tccagcatga cttactctaa    32580
caatgggtgg tctcgatttt gaaatacttt cttctccaag cctttcatga caccctgtct    32640
ctgttggttc tgaaaatgtt ggattttgtc tcagcccttg cttctggaaa cagccaaggt    32700
taagaaaacc ccccatgctt tgtgttctag cagacagctt cctgcaaaga gccatcttcc    32760
cagagcactt aggcctctta gatgtctccc ttgtttaatt atgacaagag cacacacaca    32820
gaccctccaa attcccattc ttagtcttct aaatgattag ctgagctgct tttccccact    32880
gattaatcgg aataaaatgc tcattaacca aacttccctc cttttcccag gtccctaaac    32940
tttcctgagt cggcagacat cccctctgga gaagaggttg gccccagagt cgaacatcct    33000
ctgatctacc tgatcctgct gcccttccat tccacttccc cacatctgtt ctttctggtc    33060
gtgtttactc ccctattaaa aaacaaaac cagaaaacgt gtttgcctag atcttgagac    33120
tctggaagat cttaacagtc agaggttccc cctatttgca atgatctcct ttcctgcccc    33180
ttcctatcct tgcaataatc cttttgaata aagtctctcc ttactaaatc cagttcctaa    33240
aaattaattt ttttagag                                                  33258
```

<210> SEQ ID NO 2
<211> LENGTH: 448
<212> TYPE: PRT
<213> ORGANISM: Homo sapiens
<220> FEATURE:
<221> NAME/KEY: misc_feature
<223> OTHER INFORMATION: presenilin-2 isoform 1

<400> SEQUENCE: 2

```
Met Leu Thr Phe Met Ala Ser Asp Ser Glu Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
```

```
                145                 150                 155                 160
Lys Tyr Arg Cys Tyr Lys Phe Ile His Gly Trp Leu Ile Met Ser Ser
                    165                 170                 175
Leu Met Leu Leu Phe Leu Phe Thr Tyr Ile Tyr Leu Gly Glu Val Leu
                180                 185                 190
Lys Thr Tyr Asn Val Ala Met Asp Tyr Pro Thr Leu Leu Thr Val
            195                 200                 205
Trp Asn Phe Gly Ala Val Gly Met Val Cys Ile His Trp Lys Gly Pro
210                 215                 220
Leu Val Leu Gln Gln Ala Tyr Leu Ile Met Ile Ser Ala Leu Met Ala
225                 230                 235                 240
Leu Val Phe Ile Lys Tyr Leu Pro Glu Trp Ser Ala Trp Val Ile Leu
                245                 250                 255
Gly Ala Ile Ser Val Tyr Asp Leu Val Ala Val Leu Cys Pro Lys Gly
                260                 265                 270
Pro Leu Arg Met Leu Val Glu Thr Ala Gln Glu Arg Asn Glu Pro Ile
            275                 280                 285
Phe Pro Ala Leu Ile Tyr Ser Ser Ala Met Val Trp Thr Val Gly Met
290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Glu Pro Ser Tyr
                325                 330                 335
Pro Glu Val Phe Glu Pro Pro Leu Thr Gly Tyr Pro Gly Glu Glu Leu
                340                 345                 350
Glu Glu Glu Glu Glu Arg Gly Val Lys Leu Gly Leu Gly Asp Phe Ile
            355                 360                 365
Phe Tyr Ser Val Leu Val Gly Lys Ala Ala Ala Thr Gly Ser Gly Asp
            370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
                405                 410                 415
Pro Ile Ser Ile Thr Phe Gly Leu Ile Phe Tyr Phe Ser Thr Asp Asn
                420                 425                 430
Leu Val Arg Pro Phe Met Asp Thr Leu Ala Ser His Gln Leu Tyr Ile
            435                 440                 445

<210> SEQ ID NO 3
<211> LENGTH: 19
<212> TYPE: DNA
<213> ORGANISM: Homo sapiens
<220> FEATURE:
<221> NAME/KEY: misc_feature
<223> OTHER INFORMATION: Forward 5'-3' Primer

<400> SEQUENCE: 3
catcagccct ttgccttct                                                19

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: Reverse 3'-5' Primer

<400> SEQUENCE: 4
```
ctcaccttgt agcagcggta                                           20

<210> SEQ ID NO 5
<211> LENGTH: 26
<212> TYPE: DNA
<213> ORGANISM: Homo sapiens
<220> FEATURE:
<221> NAME/KEY: misc_feature
<223> OTHER INFORMATION: Forward 5'-3' Primer

<400> SEQUENCE: 5
acagaattcg ccccggcctg gtacac                                    26

<210> SEQ ID NO 6
<211> LENGTH: 25
<212> TYPE: DNA
<213> ORGANISM: Homo sapiens
<220> FEATURE:
<221> NAME/KEY: misc_feature
<223> OTHER INFORMATION: Reverse 3'-5' Primer

<400> SEQUENCE: 6
taagcttggc acggctgtcc aagga                                     25

<210> SEQ ID NO 7
<211> LENGTH: 20
<212> TYPE: DNA
<213> ORGANISM: Homo sapiens
<220> FEATURE:
<221> NAME/KEY: misc_feature
<223> OTHER INFORMATION: Forward 5'-3' Primer

<400> SEQUENCE: 7
tcagcatcta cacgccattc                                           20

<210> SEQ ID NO 8
<211> LENGTH: 20
<212> TYPE: DNA
<213> ORGANISM: Homo sapiens
<220> FEATURE:
<221> NAME/KEY: misc_feature
<223> OTHER INFORMATION: Reverse 3'-5' Primer

<400> SEQUENCE: 8
agcaccacca agaagatggt                                           20

<210> SEQ ID NO 9
<211> LENGTH: 26
<212> TYPE: DNA
<213> ORGANISM: Homo sapiens
<220> FEATURE:
<221> NAME/KEY: misc_feature
<223> OTHER INFORMATION: Forwad 5'-3' Primer

<400> SEQUENCE: 9
attcgccccg gcctggtaca ctgcca                                    26

<210> SEQ ID NO 10
<211> LENGTH: 27
<212> TYPE: DNA
<213> ORGANISM: Homo sapiens
<220> FEATURE:
<221> NAME/KEY: misc_feature
<223> OTHER INFORMATION: Reverse 3'-5' Primer

<400> SEQUENCE: 10

```
ctgtccaagg agctgcaggc ggcgcag                                          27

<210> SEQ ID NO 11
<211> LENGTH: 25
<212> TYPE: DNA
<213> ORGANISM: Homo sapiens
<220> FEATURE:
<221> NAME/KEY: misc_feature
<223> OTHER INFORMATION: g1N141I guide RNA F

<400> SEQUENCE: 11
caccgcatca tgatcagcgt catcg                                            25

<210> SEQ ID NO 12
<211> LENGTH: 25
<212> TYPE: DNA
<213> ORGANISM: Homo sapiens
<220> FEATURE:
<221> NAME/KEY: misc_feature
<223> OTHER INFORMATION: g1N141I guide RNA R

<400> SEQUENCE: 12
aaaccgatga cgctgatcat gatgc                                            25

<210> SEQ ID NO 13
<211> LENGTH: 100
<212> TYPE: DNA
<213> ORGANISM: Homo sapiens
<220> FEATURE:
<221> NAME/KEY: misc_feature
<223> OTHER INFORMATION: Donor ssODN#A N141I

<400> SEQUENCE: 13
gagagaagcg tggctggagg gcagggccag ggcctcacct tgtagcagcg gtacttgtag      60
agcaccacca agaagatggt cagggtgttc agcacggagt                            100

<210> SEQ ID NO 14
<211> LENGTH: 21
<212> TYPE: DNA
<213> ORGANISM: Homo sapiens
<220> FEATURE:
<221> NAME/KEY: misc_feature
<223> OTHER INFORMATION: Forward 5' Primer

<400> SEQUENCE: 14
taacggcggc agacaaaaag a                                                21

<210> SEQ ID NO 15
<211> LENGTH: 22
<212> TYPE: DNA
<213> ORGANISM: Homo sapiens
<220> FEATURE:
<221> NAME/KEY: misc_feature
<223> OTHER INFORMATION: Reverse 5'-3' Primer

<400> SEQUENCE: 15
gaagtattgc ttcagttggc ct                                               22

<210> SEQ ID NO 16
<211> LENGTH: 21
<212> TYPE: DNA
<213> ORGANISM: Homo sapiens
<220> FEATURE:
<221> NAME/KEY: misc_feature
<223> OTHER INFORMATION: Forward 5' Primer

<400> SEQUENCE: 16
```

-continued agaagaacgg caagtacgag a                                          21

<210> SEQ ID NO 17
<211> LENGTH: 21
<212> TYPE: DNA
<213> ORGANISM: Homo sapiens
<220> FEATURE:
<221> NAME/KEY: misc_feature
<223> OTHER INFORMATION: Reverse 5'-3' Primer

<400> SEQUENCE: 17
tgttgaggga cagattgtgg c                                          21

<210> SEQ ID NO 18
<211> LENGTH: 21
<212> TYPE: DNA
<213> ORGANISM: Homo sapiens
<220> FEATURE:
<221> NAME/KEY: misc_feature
<223> OTHER INFORMATION: Forward 5' Primer

<400> SEQUENCE: 18
taacggcggc agacaaaaag a                                          21

<210> SEQ ID NO 19
<211> LENGTH: 22
<212> TYPE: DNA
<213> ORGANISM: Homo sapiens
<220> FEATURE:
<221> NAME/KEY: misc_feature
<223> OTHER INFORMATION: Reverse 5'-3' Primer

<400> SEQUENCE: 19
gaagtattgc ttcagttggc ct                                         22

<210> SEQ ID NO 20

<400> SEQUENCE: 20

000

<210> SEQ ID NO 21

<400> SEQUENCE: 21

000

<210> SEQ ID NO 22
<211> LENGTH: 20
<212> TYPE: DNA
<213> ORGANISM: Homo sapiens
<220> FEATURE:
<221> NAME/KEY: misc_feature
<223> OTHER INFORMATION: Forward 5' Primer

<400> SEQUENCE: 22
acgaatctcc gaccaccact                                            20

<210> SEQ ID NO 23
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5'-3' Primer

<400> SEQUENCE: 23
ccatggccac aacaactgac                                               20

<210> SEQ ID NO 24
<211> LENGTH: 22
<212> TYPE: DNA
<213> ORGANISM: Homo sapiens
<220> FEATURE:
<221> NAME/KEY: misc_feature
<223> OTHER INFORMATION: Forward 5' Primer

<400> SEQUENCE: 24
gaagtgtccc aggacatgat aa                                            22

<210> SEQ ID NO 25
<211> LENGTH: 22
<212> TYPE: DNA
<213> ORGANISM: Homo sapiens
<220> FEATURE:
<221> NAME/KEY: misc_feature
<223> OTHER INFORMATION: Reverse 5'-3' Primer

<400> SEQUENCE: 25
ctcttgagta gctgggattg ag                                            22

<210> SEQ ID NO 26
<211> LENGTH: 46
<212> TYPE: DNA
<213> ORGANISM: Homo sapiens
<220> FEATURE:
<221> NAME/KEY: misc_feature
<223> OTHER INFORMATION: Forward 5'-3' Primer

<400> SEQUENCE: 26
ctccgtgctg atcaccctca tcatgatcag cgtcatcggt tatgac                  46

<210> SEQ ID NO 27
<211> LENGTH: 48
<212> TYPE: DNA
<213> ORGANISM: Homo sapiens
<220> FEATURE:
<221> NAME/KEY: misc_feature
<223> OTHER INFORMATION: Reverse 3'-5' Primer

<400> SEQUENCE: 27
gaggcacgac tagtgggagt agtactagtc gcagtagcac caatactg                48

<210> SEQ ID NO 28
<211> LENGTH: 20
<212> TYPE: DNA
<213> ORGANISM: Homo sapiens
<220> FEATURE:
<221> NAME/KEY: misc_feature
<223> OTHER INFORMATION: Forward 5'-3' Primer

<400> SEQUENCE: 28
catcatgatc agcgtcatcg                                               20

<210> SEQ ID NO 29
<211> LENGTH: 25
<212> TYPE: DNA
<213> ORGANISM: Homo sapiens
<220> FEATURE:
<221> NAME/KEY: misc_feature
<223> OTHER INFORMATION: g1N2411 guide RNA F

<400> SEQUENCE: 29

```
caccgcatca tgatcagcgt catcg                                            25

<210> SEQ ID NO 30
<211> LENGTH: 25
<212> TYPE: DNA
<213> ORGANISM: Homo sapiens
<220> FEATURE:
<221> NAME/KEY: misc_feature
<223> OTHER INFORMATION: g1N2411 guide RNA R

<400> SEQUENCE: 30
aaaccgatga cgctgatcat gatgc                                            25

<210> SEQ ID NO 31
<211> LENGTH: 118
<212> TYPE: DNA
<213> ORGANISM: Homo sapiens
<220> FEATURE:
<221> NAME/KEY: misc_feature
<223> OTHER INFORMATION: Donor ssODN#A N141I

<400> SEQUENCE: 31
gagagaagcg tggctggagg gcagggccag ggcctcacct tgtagcagcg gtacttgtag      60
agcaccacca agaagatggt cataaccacg atgacgctga tcatgatgag ggtgttca       118
```

METHOD AND COMPOSITION FOR GENERATING BASAL FOREBRAIN CHOLINERGIC NEURONS (BFCNS)

CROSS REFERENCE TO RELATED APPLICATION(S)

This application claims the benefit of priority under 35 U.S.C. § 119(e) of U.S. Provisional Patent Application Ser. No. 62/511,271, filed May 25, 2017, U.S. Provisional Patent Application Ser. No. 62/571,741, filed Oct. 12, 2017, U.S. Provisional Patent Application Ser. No. 62/574,639, filed Oct. 19, 2017, and U.S. Provisional Patent Application Ser. No. 62/586,571, filed Nov. 15, 2017, the entire contents of each of which is incorporated herein by reference in their entireties.

STATEMENT OF GOVERNMENT SUPPORT

This invention was made with government support under Grant Nos. AG005138, AG046170, and AG042965 awarded by the National Institutes of Health. The government has certain rights in the invention.

INCORPORATION OF SEQUENCE LISTING

The material in the accompanying sequence listing is hereby incorporated by reference into this application. The accompanying sequence listing text file, name NYSC1390_4_Sequence_Listing.txt, was created on May 24, 2018, and is 53 kb. The file can be accessed using Microsoft Word on a computer that uses Windows OS.

BACKGROUND OF THE INVENTION

Field of the Invention

The present invention relates generally to the field of medicine, and more specifically to methods and compositions for developing basal forebrain cholinergic neurons (BFCNs) from stem cells, and in particular, BFCNs comprising repaired electrophysiological defects relating to one or more mutations in the presenilin 2 gene (PSEN2), and the use of such BFCNs in cell-based therapies to treat Alzheimer's disease.

Background Information

Alzheimer's disease (AD) is a progressive disease resulting in senile dementia. Broadly speaking the disease falls into two categories: late onset, which occurs in old age (65+ years) and early onset, which develops well before the senile period, i.e, between 35 and 60 years. In both types of disease, the pathology is the same but the abnormalities tend to be more severe and widespread in cases beginning at an earlier age. The disease is characterized by at least two types of lesions in the brain, senile plaques and neurofibrillary tangles. Senile plaques are areas of disorganized neuropil up to 150 µm across with extracellular amyloid deposits at the center visible by microscopic analysis of sections of brain tissue. Neurofibrillary tangles are intracellular deposits of microtubule associated tau protein consisting of two filaments twisted about each other in pairs.

The principal constituent of the plaques is a peptide termed Aβ or β-amyloid peptide. Aβ peptide is an internal fragment of 39-43 amino acids of a precursor protein termed amyloid precursor protein (APP). Several mutations within the APP protein have been correlated with the presence of Alzheimer's disease. Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PSEN1 and PSEN2, are thought indirectly to affect processing of APP to generate increased amounts of long form Aβ. These observations suggest that Aβ, and particularly its long form, is a causative element in Alzheimer's disease.

There are 5 million people currently affected by Alzheimer's disease in the US and, according to the Alzheimer's Association, this number will increase to 16 million by the year 2050. Unfortunately, we only have direct evidence for genetic causation that accounts for 3-5% of these patients. This percentage encompasses the autosomal dominant early onset familial Alzheimer's disease (EOFAD) variants caused by inherited fully penetrant autosomal dominant mutations in the APP, or PSEN1, PSEN2 that constitute the γ-secretase apparatus [87], and changes in their function increases the production of Aβ42 oligomers and/or deposition of amyloid plaques.

After decades studying murine models of AD that do not fully recapitulate the pathophysiology of this disease in the human brain [5, 57, 58], a complementary new concept of AD modeling in vitro has emerged upon the breakthrough by [81] allowing adult human tissue reprogramming into iPSC using defined factors, and their subsequent in vitro differentiation into specific brain cell types.

BFCNs are one of the most vulnerable neuronal populations whose deterioration explains, in part, the cognitive decline in AD patients. Apart from the evidence for BFCN failure and atrophy, other studies have revealed that human embryonic stem cell-derived BFCNs transplanted into AD mouse models can be associated with improvement in the learning behavior of the implanted mouse [94]. These findings highlight the relevance of iPSC- and ESC-derived BFCNs as not only early clinical indicators but also as a potential strategy for subtype-specific cell-based therapy for AD [39]. In order to move this cell-based therapeutic strategy forward, there has been an urgent need for a refined differentiation protocol to generate human ESC- and/or iPSC-derived BFCNs.

SUMMARY OF THE INVENTION

The present invention provides a highly reproducible protocol to efficiently derive BFCNs from pluripotent stem cells (PSCs), including embryonic stem cells (ESCs) and induced pluripotent stem cells (iPSCs).

Accordingly, in one embodiment, the invention provides a method of generating BFCNs. The method includes culturing PSCs in a basal media comprising an inhibitor of transforming growth factor beta (TGF-β) signaling and an activator of sonic hedgehog (Shh) signaling to induce neuroectodermal differentiation. In some aspects, the basal media is a modified mTeSR1 formulation that lacks factors that support pluripotency including basic fibroblast growth factor (bFGF), TGF-β, lithium chloride (Li—Cl), GABA and pipecolic acid. In some aspects, culturing is performed in the presence of dual SMAD inhibitors, such as SB431542 and LDN193189 along with one or more agonists of smoothened protein, such as smoothened agonist (SAG) and purmorphamine. After about 9, 10, 11 or 12 days of culturing, CD271+ cells are selected and in a neuronal basal medium, such as Brainphys™ to generate neuronal embryoid bodies (NEBs). The neuronal basal medium is optionally supplemented with one or more of B27 supplement, an inhibitor of rho-associated protein kinase (ROCK), nerve growth factor (NGF) and brain derived neurotrophic factor (BDNF). After about 7, 8, 9 or 10 days of culturing the CD271+ cells, the formed NEBs are harvested, dissociated, and plated as monolayer cultures and further cultured in a neuronal basal medium optionally supplemented with B27 supplement, NGF and BDNF. To ensure differentiation into BFCNs, the cultured cells are analyzed for positive expression of Tuj1, MAP2, BF1, Nkx2.1 and p75.

In another embodiment, the method utilizes iPSCs which may be treated with a gene editing system to repair one or more mutations, such as a mutation of presenilin 1 (PSEN1) or presenilin 2 (PSEN2). In one aspect, the mutation is PSEN2$^{N141I}$, repair of which restores neuronal excitability in BFCNs.

Accordingly, in another embodiment, the invention provides a method of treating a disease or disorder in a subject. The method includes administering to a subject a BFCN generated using the culturing method described herein. In certain aspects, the disease or disorder is an amyloidogenic disease, such as systemic amyloidosis, Alzheimer's disease, mature onset diabetes, Parkinson's disease, Huntington's disease, fronto-temporal dementia, and prion-related transmissible spongiform encephalopathies. In embodiments, a BFCN having a mutation that impairs neuronal excitability, such as PSEN2$^{N141I}$, may be obtained from a subject and used to generate an iPSC, which in turn may be treated with a gene editing system to repair the mutation. The gene edited iPSC is then cultured as described herein to produce BFCNs having restored neuronal excitability which are administered to the subject to treat the disease or disorder. In certain aspects, the disease or disorder is AD.

In a related embodiment, the invention provides a method of restoring neuronal excitability in BFCNs in a subject. The method includes: a) isolating a BFCN from the subject, wherein the BFCN has a mutation in PSEN2 resulting in impaired neuronal excitability of the BFCN; b) generating an iPSC using the BFCN of (a); c) repairing the PSEN2 mutation in the iPSC; d) culturing the iPSC of (c) using the differentiation protocol described herein to generate a BFCN having the repaired mutation; and e) administering the iPSC of (d) to the subject, thereby restoring neuronal excitability in BFCNs in the subject.

Also provided is a method of identifying a compound for treatment or prevention of a disease or disorder associated with diminished neuronal excitability in BFCNs. The method includes: a) contacting a BFCN or neuronal embryoid body (NEB) generated using the differentiation protocol described herein with a candidate compound, wherein the BFCN comprises a mutation in PSEN2 resulting in impaired neuronal excitability of the BFCN; and b) detecting neuronal excitability of the BFCN after contact with the candidate compound. An increase in neuronal excitability of the BFCN after contact with the candidate compound identifies the compound as a compound potentially capable of restoring neuronal excitability in BFCNs.

The invention further provides a BFCN generated using the differentiation protocol as described herein. The BFCN may include a gene edited repair of PSEN2, as well as a detectable marker recombinantly introduced into the BFCN genome.

The invention also provides a kit for generating a BFCN. The kit includes a culture media having an inhibitor of TGF-β signaling and an activator of Shh signaling. In embodiments, the culture media is a modified mTeSR1 formulation that lacks factors that support pluripotency including bFGF, TGF-β, lithium chloride (Li—Cl), GABA and pipecolic acid. In embodiments, the culture media includes dual SMAD inhibitors, such as SB431542 and LDN193189, along with one or more agonists of smoothened protein, such as smoothened agonist (SAG) and purmorphamine. The kit may also include a neuronal basal medium, such as Brainphys™ optionally supplemented with one or more of B27 supplement, an inhibitor of ROCK, NGF sand BDNF. In embodiments, the kit includes reagents for detection of CD271+ cells as well as cells which positively express Tuj1, MAP2, BF1, Nkx2.1 and p75.

DETAILED DESCRIPTION OF THE INVENTION

Figures 1A, 1B, 1C, 1D, 1E:
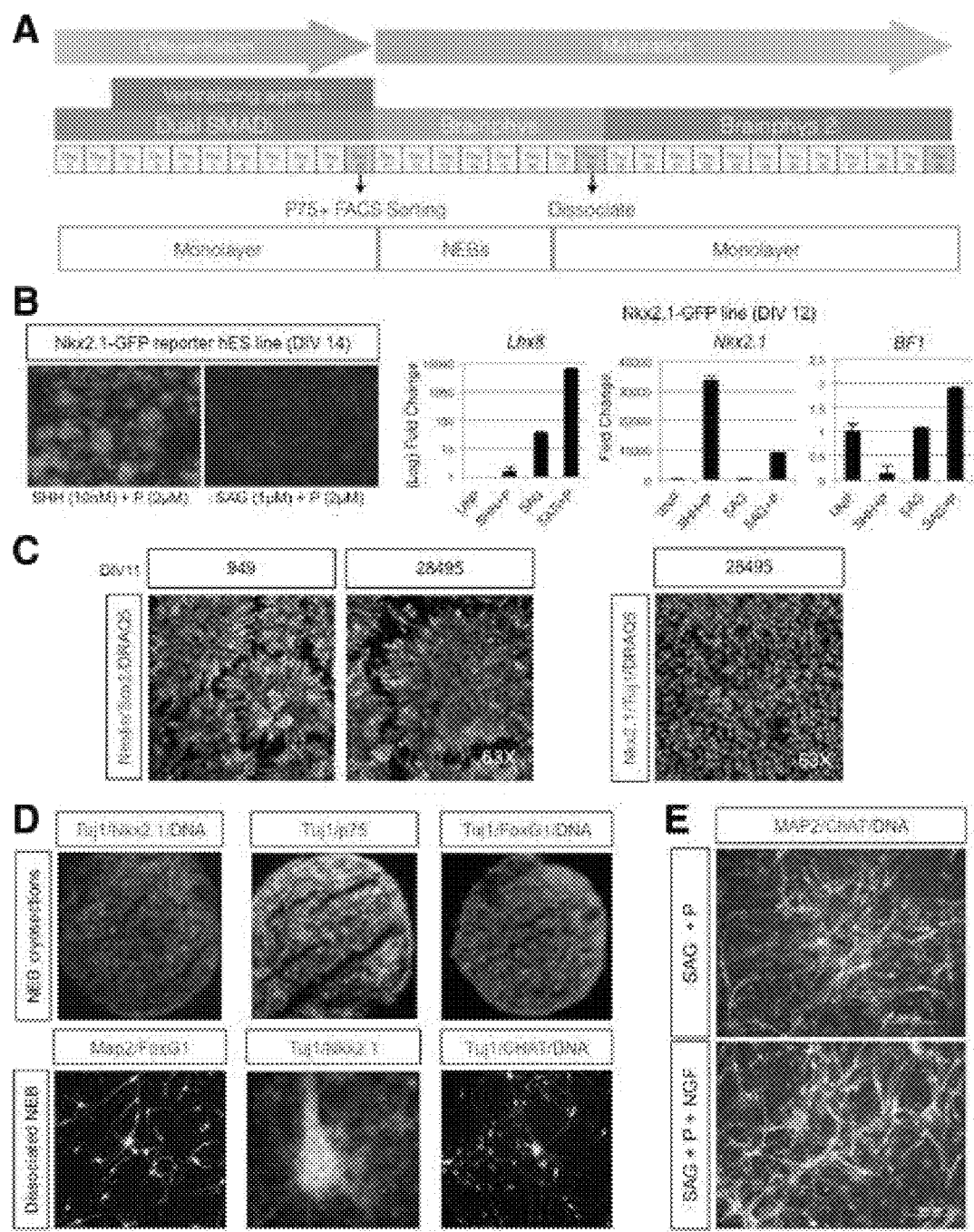
FIGS. 1A-1E. Overview schematic of basal cholinergic differentiation protocol. (A) Cells are plated and allowed to reach 100% confluency (Day 0), before the initiation of dual SMAD inhibition and the subsequent introduction of ventralizing agents (Day 2). At day 10 the monolayer is dissociated, sorted for p75+ cells, and kept as NEBs until day 19. Then the culture is dissociated again into a monolayer (See Methods for more details). (B) Left panel shows sustained EGFP expression driven by Nkx2.1 induction in NKx2.1-EGFP hESCs upon SHH plus purmorphamine or SAG plus purmorphamine treatment, maintained at Day 14, after removal of treatment at Day 8. Right panel shows Nkx2.1, Lhx8 and BF1 relative gene expression to GAPDH measured by qPCR, in NKx2.1-EGFP cell line in the presence of the indicated ventralizing agents, or unpatterned (UNP) at Day 12. n=3, in technical triplicates. (C) Confocal microscope images of Nestin, Sox2 and DRAQ5 immunostaining in fControl and control lines at Day 11, showing typical neural rosettes (left panel), or Tuj1, Nkx2.1 right and DRAQ5 in the right panel. Images representative of 3 independent experiments. (D) Fluorescence microscope images of immunostained NEB cryosections or dissociated NEBs into a monolayer with the BFCN markers Nkx2.1/Tuj1/p75/BF1/MAP2/ChAT. (E) Dissociated NEBs into a monolayer immunostained at Day 50 with MAP2, ChAT and Hoescht. Fluorescence microscope images the effect of NGF addition to SAG plus purmorphamine treatment alone. Images are representative of at least 3 independent experiments.

The present invention is based on the discovery of a robust, fast, and reproducible differentiation protocol to generate BFCNs from PSCs using a chemically defined medium.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described. herein can also be used in the practice or testing of the present invention, the preferred methods and materials are now described. All publications mentioned herein are incorporated herein by reference to disclose and described the methods and/or materials in connection with which the publications are cited.

Unless otherwise defined, all technical and scientific terms used herein have the same meaning as commonly understood by one of ordinary skill in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The terminology used in the description is for describing particular embodiments only and is not intended to be limiting of the invention. Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein. shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, in certain methods described herein that include more than one step or act, the order of the steps or acts of the method is not necessarily limited to the order in which the steps or acts of the method are recited unless the context indicates otherwise.

The term "PSEN2 gene" refers herein to a gene that encodes a PSEN2 polypeptide. The PSEN2 gene is represented by NCBI Reference Sequence: NC_000001.11 (SEQ ID NO: 1) as well as known orthologs. The term "PSEN2 polypeptide" refers herein to a polypeptide that is represented by NCBI Reference Sequence: NP_000438.2 (SEQ ID NO: 2) as well as known orthologs.

The term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

The term "patient" or "subject" is used throughout the specification to describe an animal, preferably a human or a domesticated animal, to whom treatment, including prophylactic treatment, with the compositions according to the present disclosure is provided. For treatment of conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The terms "β-amyloid protein", "β-amyloid peptide", "β-amyloid", "Aβ" and "Aβ peptide" are used interchangeably herein. Aβ peptide (e.g., Aβ 39, Aβ 40, Aβ 41, Aβ 42 and Aβ 43) is about 4-kDa internal fragment of 39-43 amino acids of APP. Aβ 40, for example, consists of residues 672-711 of APP and Aβ 42 consists of residues 672-713 of APP. Aβ peptides include peptides resulting from secretase cleavage of APP and synthetic peptides having the same or essentially the same sequence as the cleavage products. Aβ peptides can be derived from a variety of sources, for example, tissues, cell lines, or body fluids (e.g. sera or cerebrospinal fluid). For example, an A β can be derived from APP-expressing cells such as Chinese hamster ovary (CHO) cells stably transfected with $APP_{717V}$F, as described, for example, in Walsh et al., (2002), Nature, 416, pp 535-539. An A B preparation can be derived from tissue sources using methods previously described (see, e.g., Johnson-Wood et al., (1997), Proc. Natl. Acad. Sci. USA 94:1550). Alternatively, Aβ peptides can be synthesized using methods which are well known to those in the art. See, for example, Fields et al., Synthetic Peptides: A User's Guide, ed. Grant, W.H. Freeman & Co., New York, N.Y., 1992, p 77). Hence, peptides can be synthesized using the automated Merrifield techniques of solid phase synthesis with the .alpha.-amino group protected by either t-Boc or F-moc chemistry using side chain protected amino acids on, for example, an Applied Biosystems Peptide Synthesizer Model 430A or 431. Longer peptide antigens can be synthesized using well known recombinant DNA techniques. For example, a polynucleotide encoding the peptide or fusion peptide can be synthesized or molecularly cloned and inserted in a suitable expression vector for the transfection and heterologous expression by a suitable host cell. A β peptide also refers to related Aβ sequences that results from mutations in the Aβ region of the normal gene.

As used herein the phrase "substantially pure" refers to a population of cells wherein at least 95% of the cells have the recited phenotype. In all embodiments that refer to a "substantially pure" cell population, alternative embodiments in which the cell populations have a lower or higher level of purity are also contemplated. For example, in some embodiments, instead of a given cell population being "substantially pure" the cell population may be one in which at least 35%, 40%, 45%, 50%, 55%, 60%, 65%, 70%, 75%, 80%, 85%, 90%, 95%, 96%, 97%, 98%, or 99% of the cells, or 100% of the cells, have the recited phenotype.

The terms "co-administration", "co-administered" and "co-administering" or "combination therapy" refer to both concurrent administration (administration of two or more agents at the same time) and time varied administration (administration of one or more agents at a time different from that of the administration of an additional agent or agents), as long as the agents are present in the area to be treated to some extent, preferably at effective amounts, at the same time.

The term "therapeutically effective amount" means the amount required to achieve a therapeutic effect. The therapeutic effect could be any therapeutic effect ranging from prevention, symptom amelioration, symptom treatment, to disease termination or cure, e.g., the treatment of Alzheimer's disease or an associated condition.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

The term "effective" is used to describe an amount of a compound, composition or component which, when used within the context of its intended use, effects an intended result. The term effective subsumes all other effective amount or effective concentration terms, which are otherwise described or used in the present application.

As used herein, the term "comprising" is intended to mean that the compositions and methods include the recited elements, but do not exclude other elements. "Consisting essentially or", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

As used herein, "kits" are understood to contain at least the non-standard laboratory reagents of the invention and one or more non-standard laboratory reagents for use in the methods of the invention.

The term "obtaining" is understood herein as manufacturing, purchasing, or otherwise coming into possession of.

As used herein, the term "treated," "treating" or "treatment" includes the diminishment or alleviation of at least one symptom associated or caused by the state, disorder or disease being treated. A subject that has been treated can exhibit a partial or total alleviation of symptoms (for example, Alzheimer's disease or associated condition), or symptoms can remain static following treatment according to the invention. The term "treatment" is intended to encompass prophylaxis, therapy and cure.

As used herein, the term "control" refers to a sample or standard used for comparison with an experimental sample. In some embodiments, the control is a sample obtained from a healthy patient. In other embodiments, the control is a historical control or standard reference value or range of values (such as a previously tested sample, subject, or group of samples or subjects).

Methods

BFCNs are believed to be one of the first cell types to be affected in all forms of AD, and their dysfunction is clinically correlated with impaired short-term memory formation and retrieval. As detailed in the Example of this disclosure, the inventors present an optimized in vitro protocol to generate human BFCNs from iPSCs, using cell lines from PSEN2 mutation carriers and controls. Cell lines harboring the $PSEN2^{N141I}$ mutation displayed an increase in the Aβ42/40 in iPSC-derived BFCNs. Neurons derived from $PSEN2^{N141I}$ lines generated fewer maximum number of spikes in response to a square depolarizing current injection. The height of the first action potential at rheobase current injection was also significantly decreased in $PSEN2^{N141I}$ BFCNs. CRISPR/Cas9 correction of the PSEN2 point mutation abolished the electrophysiological deficit, restoring both the maximal number of spikes and spike height to the levels recorded in controls. Increased Aβ42/40 was also normalized following CRISPR/Cas-mediated correction of the $PSEN2^{N141I}$ mutation. The genome editing data set forth herein confirms the robust consistency of mutation-related changes in Aβ42/40 ratio while also showing a PSEN2-mutation-related alteration in electrophysiology.

Accordingly, in one embodiment, the invention provides a method of generating BFCNs. The method may first include preparing PSC colonies. PSCs are seeded (plated) at low density and grown in an adherent culture for about 1-2 days. "Low density" means about 8,000 to about 11,000 cells/cm². Cells are preferably seeded at about 9,500 to about 10,500 cells/cm², more preferably at about 10,000 cells/cm². After about 1-2 days (or greater, i.e., 3, 4, 5, 6, 7, 8, 9, 10 or more), the PSCs form colonies, which are preferably about 75 μm to about 300 μm in diameter, more preferably about 100 μm to about 250 μm in diameter.

The term "PSCs" has its usual meaning in the art, i.e., self-replicating cells that have the ability to develop into endoderm, ectoderm, and mesoderm cells. Preferably, PSCs are hPSCs. PSCs include ESCs and iPSCs, preferably hESCs and hiPSCs. PSCs can be seeded on a surface comprising a matrix, such as a gel or basement membrane matrix. A preferable matrix is the protein mixture secreted by Engelbreth-Holm-Swarm (EHS) mouse sarcoma cells, sold under trade names including MATRIGEL®, CULTREX®, and GELTREX®. Other suitable matrices include, without limitation, collagen, fibronectin, gelatin, laminin, poly-lysine, vitronectin, and combinations thereof.

In some embodiments, media suitable for use in maintaining pluripotent stem cells is used. In embodiments such a medium is mTeSR1 medium from Stem Cell Technologies. However, one of skill in the art will recognize that there are several other types of media that are equivalent to mTeSR medium in terms of their suitability for use in maintaining pluripotent stem cells, any of which could be used. Typically such media will contain one or more pluripotency factors to facilitate the maintenance of cells in a pluripotent state. The composition of mTeSR1 medium is known in the art and described in, for example, Ludwig et al., 2006 (Nat Methods. 2006 August; 3(8):637-46; "Feeder-Independent Culture of Human Embryonic Stem Cells"), the contents of which are hereby incorporated by reference.

The pluripotent stem cells used in the method of the invention can be any suitable type of pluripotent stem cells. Where iPSCs are used, such cells may have been "reprogrammed" to the pluripotent state from a non-pluripotent state using any suitable means known in the art, including, but not limited to, modified RNA-based methods, Sendai virus based methods, and the like. Furthermore, such cells may have been reprogrammed to the pluripotent state using any suitable cocktail of reprogramming factors known in the art.

In one embodiment, after PSCs are prepared and grown to confluence in, for example mTeSR1 media, the method includes culturing the PSCs in a basal media comprising an inhibitor of transforming growth factor beta (TGF-β) signaling and an activator of sonic hedgehog (Shh) signaling to induce neuroectodermal differentiation. The basal media utilized is a modified mTeSR1 medium, which is a variant of mTeSR1 medium (sometimes referred to herein as "mTeSR1 Custom" medium) that does not comprise lithium chloride, GABA, pipecolic acid, bFGF or TGFβ1. Inhibitors of TGFβ signaling include, for example, one or more of SB431542, GW788388, LDN193189, LY2109761, LY2157299, and LY364947. Activators of Shh signaling include agonists of Smoothened, such as Smoothened Agonist (SAG; 3-chloro-N-[(1r,4r)-4-(methylamino)cyclohexyl]-N-[3-(pyridin-4-yl)benzyl]benzo[b]thiophene-2-carboxamide) and purmorphamine.

After about 6, 7, 8, 9, 10, 11 or 12 days (or greater, i.e., 15, 16, 17, 18, 19, 20, 25, 30 or more) of culturing, CD271+ cells are selected and cultured in a neuronal basal medium, such as Brainphys™ to generate neuronal embryoid bodies (NEBs). The neuronal basal medium is optionally supplemented with one or more of B27 supplement, an inhibitor of rho-associated protein kinase (ROCK), nerve growth factor (NGF) and brain derived neurotrophic factor (BDNF). Inhibitors of ROCK include, for example, GSK269962, GSK429286, H-1152, HA-1077, RKI-1447, thiazovivin, Y-27632, or derivatives thereof.

To select for CD271+ cells, overconfluent cells are lifted from the culture surface and purified by FACS and re-plated. This process allows for the formation of cell aggregates or spheres, also referred to herein as NEBs. For purposes of the present invention, the terms "NEB," "aggregate" and "sphere" are used interchangeably and refer to a multicellular three-dimensional structure, preferably, but not necessarily, of at least about 100 cells.

Lifting can be performed mechanically, with a cell scraper or other suitable implement, or chemically. Chemical lifting can be achieved using a proteolytic enzyme, for example, collagenase, trypsin, trypsin-like proteinase, recombinant enzymes, such as that sold under the trade name TRYPLE™, naturally derived enzymes, such as that sold under the trade name ACCUTASE™, and combinations thereof. Chemical lifting can also be done using a chelator, such as EDTA, or a compound such as urea. Mechanical lifting or detachment offers the advantage of minimal cell death, however it produces aggregates of variable size, thus suitable spheres need to be selected through a manual picking process. Good spheres are defined as those having a round-shape, golden/brown color, with darker core and with a diameter between about 300 μm and about 800 μm. Detaching the cells using chemical methods, such as enzymatic digestion predominantly produces spheres that are appropriate for further culture. Therefore manual picking of spheres is not required, and the detachment steps can be adapted for automation and used in high throughput studies. However, enzymatic digestion increases cell death, resulting in a lower number of spheres.

After about 5, 6, 7, 8, 9 or 10 days (or greater, i.e., 11, 12, 13, 14, 15, 16, 17, 18, 19, 20, 25, 30 or more) of culturing selected CD271+ cells, the formed NEBs are harvested, dissociated, and plated as monolayer cultures and further cultured in a neuronal basal medium, such as Brainphys™, optionally supplemented with B27 supplement, NGF and BDNF. The surface on which the cells are plated and cultured can comprise an extracellular matrix protein (e.g., collagen, fibronectin, laminin) and/or a positively charged poly-amino acid (e.g., poly-arginine, poly-lysine, poly-ornithine). Preferably the surface comprises laminin and/or poly-ornithine.

To ensure differentiation into BFCNs, the cultured cells are analyzed for positive expression of Tuj1, MAP2, BF1, Nkx2.1 and p75.

Many of the embodiments of the present invention involve certain factors to be used in (or excluded from) the compositions and methods described herein, for example as media supplements. These include, but are not limited to, bFGF, GABA, pipecolic acid, lithium chloride, TGF-β, NGF and BDNF. Each of these factors is well known in the art, including the full names of each of these factors in the cases where acronyms or other abbreviations are used. Furthermore, all of these factors are available to the public from multiple sources, including commercial sources. Exemplary amounts/concentrations for use of each of these factors in the methods and compositions of the present invention are provided in the Examples section of this patent disclosure. For all embodiments where specified amounts are referred to, amounts that are "about" the specified amount are also intended. Furthermore, one of skill in the art will recognize that in some situations further deviations from the specified amounts can be used, and will be able to determine how much of each factor to use by performing routine testing, optimization, dose-response studies, and the like, for example to reduce or increase the specified amounts, as long as the amounts used still achieve the stated effect, e.g. the stated differentiation effect. For example, in some embodiments specified amounts of the specified agents may be reduced to 10%, or 20%, or 30%, or 40%, or 50%, or 60%, or 70%, or 80%, or 90% of the stated amounts. Similarly, in some embodiments the specified amounts of the specified agents may be increased by 10%, by 20%, by 30%, by 40%, by 50%, by 60%, by 70%, by 80%, by 90%, by 100%, by 150%, by 200%, by 300%, by 400%, or by 500% of the stated amounts. Similarly, where specified factors are referred to, one of skill in the art will recognize that analogs, variants, or derivatives of such factors can also be used as long as the analogs, variants, or derivatives have the same general function/activity as the specified factors.

As discussed herein, the inventors have discovered that mutation of PSEN2 results in impaired neuronal excitability in BFCNs. As discussed in the Example herein the inventors observed significant mutation-related, editing-reversible differences in excitability of BFCNs via repair of PSEN2$^{N141I}$ mutation which restored neuronal excitability. Accordingly, the method of the invention may utilize iPSCs which may be treated with a gene editing system to repair one or more mutations, such as a mutation of presenilin 1 (PSEN1) or presenilin 2 (PSEN2). In one embodiment, the mutation is PSEN2$^{N141I}$, repair of which restores neuronal excitability in BFCNs.

As used herein the term "gene editing" or "genome editing" refers to a type of genetic engineering in which DNA is inserted, replaced, or removed from a target DNA, e.g., the genome of a cell, using one or more nucleases and/or nickases. The nucleases create specific double-strand breaks (DSBs) at desired locations in the genome, and harness the cell's endogenous mechanisms to repair the induced break by homology-directed repair (HDR) (e.g., homologous recombination) or by nonhomologous end joining (NHEJ). The nickases create specific single-strand breaks at desired locations in the genome. In one non-limiting example, two nickases can be used to create two single-strand breaks on opposite strands of a target DNA, thereby generating a blunt or a sticky end. Any suitable nuclease can be introduced into a cell to induce genome editing of a target DNA sequence including, but not limited to, CRISPR-associated protein (Cas) nucleases, zinc finger nucleases (ZFNs), transcription activator-like effector nucleases (TALENs), meganucleases, other endo- or exo-nucleases, variants thereof, fragments thereof, and combinations thereof. In particular embodiments, nuclease-mediated genome editing of a target DNA sequence (e.g., a safe harbor gene) by homology-directed repair (HDR) (e.g., homologous recombination) is used for generating a genetically modified human neural stem cell in accordance with the methods described herein.

The term "DNA nuclease" refers to an enzyme capable of cleaving the phosphodiester bonds between the nucleotide subunits of DNA, and may be an endonuclease or an exonuclease. According to the invention, the DNA nuclease may be an engineered (e.g., programmable or targetable) DNA nuclease which can be used to induce genome editing of a target DNA sequence such as a safe harbor gene. Any suitable DNA nuclease can be used including, but not limited to, CRISPR-associated protein (Cas) nucleases, zinc finger nucleases (ZFNs), transcription activator-like effector nucleases (TALENs), meganucleases, other endo- or exo-nucleases, variants thereof, fragments thereof, and combinations thereof.

In various embodiments of the invention, a gene editing system utilizes a DNA nuclease to edit a gene and repair a mutation. In specific embodiments, a mutation is repaired using one or more of the following gene editing system: CRISPR/Cas system, Cre/Lox system, TALEN system and homologous recombination.

The differentiation protocol of the present invention may be utilized to treat a disease or disorder in a subject. The method includes administering to a subject a BFCN generated using the culturing method described herein. In various embodiments, the disease or disorder is an amyloidogenic disease, such as systemic amyloidosis, Alzheimer's disease, mature onset diabetes, Parkinson's disease, Huntington's disease, fronto-temporal dementia, and prion-related transmissible spongiform encephalopathies. In embodiments, a BFCN having a mutation that impairs neuronal excitability, such PSEN2$^{N141I}$, may be obtained from a subject and used to generate an iPSC, which in turn may be treated with a gene editing system to repair the mutation. The gene edited iPSC is then cultured as described herein to produce BFCNs having restored neuronal excitability which are administered to the subject to treat the disease or disorder.

In a related manner, neuronal excitability in BFCNs in a subject may be restored. This method includes: a) isolating a BFCN from the subject, wherein the BFCN has a genetic mutation resulting in impaired neuronal excitability of the BFCN; h) generating an iPSC using the BFCN of (a); c) repairing the mutation in the iPSC; d) culturing the iPSC of (c) using the differentiation protocol described herein to generate a BFCN having the repaired mutation; and e) administering the iPSC of (d) to the subject, thereby restoring neuronal excitability in BFCNs in the subject. In embodiments, the mutations is of PSEN1 or PSEN2, such as PSEN2$^{N141I}$.

The invention also encompasses BFCNs generated using the differentiation protocol as described herein. The BFCN may include a gene edited repair of PSEN2, as well as a detectable marker recombinantly introduced into the BFCN genome. In some embodiments, BFCNs are differentiated from PSCs, and in such embodiments, the PSCs can be iPSCs. The iPSCs can be derived from a somatic cell of a subject. In one aspect, the subject has an amyloidogenic disease or disorder.

Alongside its potential for autologous cell transplantation, iPSC technology is emerging as a tool for developing new drugs and gaining insight into disease pathogenesis. Han, S. S. W. et al., Neuron. 70:626-644 (2011). The methods and cells of the invention can aid the development of high-throughput in vitro screens for compounds that promote restoration of neuronal excitability. To that end, the disclosure provides a method of identifying a compound that can be used for treatment or prevention of a disease or disorder associated with diminished neuronal excitability in BFCNs. The method includes: a) contacting a BFCN or neuronal embryoid body (NEB) generated using the differentiation protocol described herein with a candidate compound, wherein the BFCN comprises a mutation in PSEN2 resulting in impaired neuronal excitability of the BFCN; and b) detecting neuronal excitability of the BFCN after contact with the candidate compound. A beneficial effect on neuronal excitability is evident in partial or complete restoration of neuronal excitability, thereby being indicative of a candidate therapeutic agent for treating a disease or disorder associated with diminished neuronal excitability in BFCNs, such as an amyloidogenic disease or disorder. Preferably, the method is conducted in a high-throughput format.

The invention also provides a model system for a neurological disease, preferably a disease or disorder associated with diminished neuronal excitability in BFCNs, such as an amyloidogenic disease or disorder. In one aspect, the model system comprises a BFCN differentiated from an iPSC derived from a subject having a disease or disorder associated with diminished neuronal excitability in BFCNs, such as an amyloidogenic disease or disorder. The model system can further comprise a non-human mammal into which the myelin-producing cell has been transplanted. In one embodiment, the non-human mammal is a mouse or a rat. Model systems provided by the invention can be used to study diseases or disorders, including understanding underlying mechanisms and defining therapeutic targets.

In some embodiments the present invention provides tissue culture media, tissue culture media supplements, and various kits useful in performing the various methods described herein.

In one embodiment, the invention provides a kit for generating a BFCN via the differentiation protocol of the invention. The kit includes a culture media having an inhibitor of TGF-β signaling and an activator of Shh signaling. In embodiments, the culture media is a modified mTeSR1 formulation that lacks factors that support pluripotency including bFGF, TGF-β, lithium chloride (Li—Cl), GABA and pipecolic acid. In embodiments, the culture media includes dual SMAD inhibitors, such as SB431542 and LDN193189, along with one or more agonists of smoothened protein, such as smoothened agonist (SAG) and purmorphamine.

The kit may also include an additional neuronal basal medium, such as Brainphys™ optionally supplemented with one or more of B27 supplement, an inhibitor of ROCK, NGF and BDNF.

The kit may also include reagents for detection and isolation of CD271+ cells via FACS as well as detection of expression of Tuj1, MAP2, BF1, Nkx2.1 and p75.

The kit may optionally comprise instructions for use, one or more containers, one or more antibodies, or any combination thereof. A label typically accompanies the kit, and includes any writing or recorded material, which may be electronic or computer readable form (e.g., disk, optical disc, memory chip, or tape) providing instructions or other information for use of the kit contents.

The following example is provided to further illustrate the advantages and features of the present invention, but it is not intended to limit the scope of the invention. While this example is typical of those that might be used, other procedures, methodologies, or techniques known to those skilled in the art may alternatively be used.

Example I

CRISPR/Cas9-Correctable Mutation-Related Molecular and Physiological Phenotypes in iPSC-Derived Alzheimer's PSEN2$^{N141I}$ Mutation Basal forebrain cholinergic neurons (BFCNs) are believed to be one of the first cell types to be affected in all forms of AD, and their dysfunction is clinically correlated with impaired short-term memory formation and retrieval. We present an optimized in vitro protocol to generate human BFCNs from iPSCs, using cell lines from presenilin 2 (PSEN2) mutation carriers and controls. As expected, cell lines harboring the PSEN2$^{N141I}$ mutation displayed an increase in the Aβ42/40 in iPSC-derived BFCNs. Neurons derived from PSEN2$^{N141I}$ lines generated fewer maximum number of spikes in response to a square depolarizing current injection. The height of the first action potential at rheobase current injection was also significantly decreased in PSEN2$^{N141I}$ BFCNs. CRISPR/Cas9 correction of the PSEN2 point mutation abolished the electrophysiological deficit, restoring both the maximal number of spikes and spike height to the levels recorded in controls. Increased Aβ42/40 was also normalized following CRISPR/Cas-mediated correction of the PSEN2$^{N141I}$ mutation. The genome editing data confirms the robust consistency of mutation-related changes in Aβ42/40 ratio while also showing a PSEN2-mutation-related alteration in electrophysiology.

The "amyloid hypothesis" is one of the most popular formulations for the pathogenesis of Alzheimer's disease (AD). Recent examples of clinicopathological and/or clinicoradiological dissociation have led to the consideration of alternative models in order to explain, respectively, why neuropathological AD is not always associated with dementia [24], and why about one-third of patients with clinical AD have negative amyloid brain scans [40]. It has been proposed that clinical AD can be caused by one of several "feed-forward" scenarios linking amyloidosis, tauopathy, neuroinflammation, and neurodegeneration [22]. Mutations in the gene encoding presenilin 2 (PSEN2) are associated with autosomal dominant early onset familial Alzheimer's disease (EOFAD). The linkage of a locus on human chromosome 1q31-42 linked to EOFAD led to the identification of the PSEN2$^{N141I}$ point mutation in the Volga German kindreds in 1995 [43]. This mutation causes elevation in the Aβ42-43/40 ratio, thereby promoting assembly of Aβ oligomers and fibrils [83].

In considering the progression of AD, human basal forebrain cholinergic neurons (BFCNs) are one of the first cell types whose dysfunction underlies the early loss of short-term memory recall in all forms of AD. The "cholinergic hypothesis of AD" was formulated in the mid-1970s [6, 20, 61], and the discoveries of reduced acetylcholine release from neurons of the nucleus basalis of Meynert confirmed the presence of a presynaptic cholinergic deficit in the basal forebrain of AD patients [1, 71]. Based on those observations, acetylcholinesterase inhibitors were developed and continue as the most widely used symptomatic treatments for AD [21, 28, 33, 82]. Eventually, post-mortem brain biochemical and volumetric studies at different stages of the disease identified several other regions of the brain that were also affected early in the course of AD [63]. These studies have traditionally focused on the hippocampus and cortex, but more recently, attention has begun shifting back to the basal forebrain and adding other areas, such as the striatum [27, 62]. The latest analyses suggest that cholinergic basal forebrain volume measurement may be a better predictor of the transition from MCI to AD than the previous standard, hippocampal volume [10].

We previously reported the generation of iPSC-derived neurons from banked fibroblasts from subjects harboring PSEN1$^{A246E}$ and PSEN1$^{M146L}$ mutations [77]. In characterizing the gene expression profiles from these iPSC-derived neurons, we observed an unexpected association of elevated expression of the inflammasome gene NLRP2 in undifferentiated PSEN1 mutant iPSCs and their and neuronally differentiated progeny [77]. This led us to examine NLRP2 expression in our PSEN2 mutant lines and employ CRISPR/Cas9 [15] to investigate if activation of the inflammasome was tightly linked to the pathogenic mutation in PSEN2. While we did not find altered expression of NLRP2 in gene-corrected PSEN2 lines, we observed significant mutation-related, editing-reversible differences in excitability of BFCNs.

Materials and Methods

Generation and Maintenance of iPSC Lines

7889(s)B, 050643 (Control), 948 (AD1), 949(fControl), and 950 (AD2) iPSC lines were obtained via the NYSCF Repository following the guidelines from [60]. The derivation and characterization of Nkx2.1-GFP ESC line was previously published [30]. ES and iPS cell lines were expanded and maintained in serum-free mTeSR1™ media (Stem Cell Technologies). Cells were lifted using StremPro™ Accutase (ThermoFisher) and media was supplemented with 10 μM ROCK inhibitor (Y27632, Stemgent) during cell passaging.

For all studies in this paper, cell lines underwent at least 3 independent differentiations from the iPSC stage to the mature neuron stage. Data were routinely compared across these independently derived genotype-identical neurons (or in some cases neuronal precursors), and if comparable results were obtained across independently genotype-identical derived cells, they were considered to be qualified representatives of their genotype and so were passed along for genotype-specific experimentation.

Aβ42 Oligomer Preparation

Aβ42 oligomers were prepared as previously reported [23, 78]. Briefly, we dissolved 1 mg of Aβ42 (American Peptide Company) in 1,1,1,3,3,3-hexafluoro-2-propanol (HFIP) (Sigma). This preparation was aliquoted and dried using a SpeedVac™ centrifuge. The pellet was then resuspended in DMSO to obtain a 5 mM solution which was sonicated in a water bath for 10 min. From here aliquots were stored at −20 C and used within 2 weeks by diluting with 100 μl of PBS and leaving for 12 h at 4° C. in order for oligomerization to proceed. This final solution was diluted 1:16 in cell media for studies, allowing cells to be exposed to 5 μM of Aβ42 oligomers. Control wells were diluted with 1:16 PBS. Cells were exposed to oligomers or PBS without media change for a period of 3 days.

Cell Death Assays

Cells were assayed in a 96-well plate format. Oligomer or vehicle solutions were added to media and allowed to incubate for a period of 3 days. Media was then collected and assayed using a lactate dehydrogenase toxicity assay (Thermo Fisher Scientific). 50 μl of media and an equal amount of reaction mix buffer were incubated for a period of 30 min. An additional set of wells per experiment were treated with 2% Triton™ X-100 for a 5-min period in order to lyse all cells, and media from these wells was also collected and incubated as described. After incubation absorbance was recorded at 490 nm and 680 nm, signal and background absorbance, respectively. Signal values were subtracted from background, and values were adapted to the total LDH content as determined by Triton X-100 treated wells. Propidium iodide (Thermo Fisher Scientific) was added to cell media for a 1 μM final concentration and allowed to incubate for 5 min. Cells were then washed twice with media and imaged. Images were captured using CELIGO™ image cytometer and accompanying software (Nexcelom Bioscience). Each biological variable was assessed in technical triplicates within each designated "Experiment", and each designated "Experiment" was performed in at least three complete "start to finish" iterations.

Differentiation of Basal Forebrain Cholinergic Neurons from iPS and ES Cells

Human ES or iPSC were plated as single cells after chemical dissociation using Accutase™ (Sigma-Aldrich) into Cul-Trex™ (Trevigen) coated plates, at a density of $4\text{-}8\times10^5$ cells per well in 6-well plates or petri dishes and adapting cell numbers. Cells were initially maintained in mTeSR1™ media (Stem Cell Technologies) until reaching full confluency. On "day 0" of differentiation, media was replaced by Custom mTeSR1™ media (Stem Cell Technologies) lacking factors promoting pluripotency i.e., bFGF, TGF-β, Li—Cl, GABA and pipecolic acid. The addition of dual SMAD inhibitors (SB431542 10 μM plus LDN193189 250 nM, Selleckchem) at day 0 drives cells towards neuroectoderm specification. At day 2 of differentiation, media was replaced by Custom mTeSR1 containing dual SMAD inhibitors plus two ventralizing agents: SAG at 500 nM (R&D) and Purmorphamine at 2 μM (Stemgent™). Cells were fed every 2 days with this media until day 9, when media was progressively switched to Brainphys™ media (Stemcell Technologies) supplemented with B27 (Life Technologies) [3]. Neural progenitors were harvested at day 11 using Accutase, p75+(CD271) NPCs were purified by FACS and plated at a density of 80,000 cells per well into non-adherent 96 well V-bottom plates in Brainphys™+B27 supplemented with 10 μM ROCK inhibitor (Y27632, Stemgent), Nerve Growth Factor, NGF, (Alamone labs, 50 ng/mL) and Brain Derived Neurotrophic Factor, BDNF, (R&D, 50 ng/mL). Cells were allowed to aggregate and form Neuronal Embryoid Bodies (NEBs) and were fed every other day until day 19. At day 19 NEBs were dissociated using Accutase (Sigma-Aldrich) and were plated as monolayer cultures on plates coated with branched polyethynilimine (0.1%, Sigma-Aldrich) and laminin (10 mg/mL, Life Technology) in Brainphys™ media+B27 supplement with BDNF and NGF. The media was changed every 2 days until analysis. As an alternative, 3D NEBs were dissected manually into 3-4 pieces for expansion and further grown, or were cryopreserved. Initial versions of the protocol used Neurobasal™ as a base media instead of Brainphys™.

Genomic DNA Isolation and Sequencing

Genomic DNA was isolated from PSEN2 mutant or control iPSC lines using High Pure™ PCR Template Preparation Kit (Roche) following manufacturer instructions. Genomic samples were treated with RNAse (QIAGEN) prior to amplification. A fragment from exon 5 of PSEN2 containing $PSEN2^{N141I}$ mutation was amplified using the following primers: Forward 5'-CATCAGCCC TTTGC-CTTCT-3' (SEQ ID NO: 3), Reverse: 5'-CTCACCTTGTAGCAGCGGTA-3' (SEQ ID NO: 4), generating a 173 bp fragment, regardless of the genotype. For detection of ApoE allelic variants, a fragment of 244 bp was amplified prior to sequencing using the primers: Forward: 5'-ACAGAATTCGCCCCGGCCTGGTACAC-3' (SEQ ID NO: 5), Reverse: 5'-TAAGCTTGGCACGGCTGTC-CAAGGA-3' (SEQ ID NO: 6). Both PCR were performed with the following settings: 10 min 94 C, 40 cycles (30 s 94 C, 20 s 62 C, 10 s 72 C) 7 min 72 C. PCR products were run in a 2% agarose gel to check the size of the amplified fragment. After amplification, samples were cleaned using EXOSAP-It™ (Thermo Fisher Scientific) and then sequenced using the following primers: PSEN2 (Forward: 5'-TCAGCATCTACACGCCATTC-3' (SEQ ID NO: 7), Reverse: 5'-AGCACCACCAAGAAGATGGT-3') (SEQ ID NO: 8), from [53]; ApoE (Forward: 5'-ATTCGCC-CCGGCCTGGTACACTGCCA-3' (SEQ ID NO: 9), Reverse: 5'-CTGTCCAAGGAGCTGCAGGCGGCGCAG-3' (SEQ ID NO: 10)), from [36].

CRISPR/Cas9 Gene Correction iAD1 Control and iAD2 Control lines were originated from 948 (AD1) and 950 (AD2) iPSC lines by CRISPR/Cas9-mediated correction of the $PSEN2^{N141I/WT}$ heterozygous point mutation to $PSEN2^{WT/WT}$. g1N141I single guide RNA (sgRNA) was cloned into pSpCas9(BB)-2A-GFP (PX458) vector, generating pSpCas9-g1N141I-GFP vector to direct gene editing to the sequence in exon 5 of PSEN2 where the Volga mutation is located. Single stranded oligonucleotides (ssODN) are efficient templates for the CRISPR/Cas9 correction [13, 66]. ssODN#A-N141I (sequence detail below) was used as donor sequence for gene correction. We designed asymmetric ssODN sequences with a long homology arm of 91 bp, and a short homology arm of 36 bp since asymmetrical ssODNs showed a higher efficiency of homology-directed repair using CRISPR/Cas9 [68].

TABLE 1

| Sequence Name | Bases | Sequence | SEQ ID NO |
|---|---|---|---|
| g1N141I guide RNA F | 25 | /5Phos/CACCGCATCATGATCAGCGTCATCG | 11 |
| g1N141I guide RNA R | 25 | /5Phos/AAACCGATGACGCTGATCATGATGC | 12 |
| Donor ssODN#A N141I | 127 | GAGAGAAGCGTGGCTGGAGGGCAGGGC CAGGGCCTCACCTTGTAGCAGCGGTACT TGTAGAGCACCACCAAGAAGATGGTCA TAACCACGATGACGCTGATCATGATGA GGGTG<u>T</u>TCAGCACGGAGT | 13 |

Underline = base of the ssODN that corrects the point mutation.

The donor sequence and pSpCas9-g1N141I-GFP vector were transduced in the AD1 and AD2 iPSC lines, plated at 50-70% confluency, using Amaxa Human Stem Cell Nucleofector™ kit (Lonza VPH-5002) and re-plated for recovery. GFP+ cells were sorted in a BD FACSAria IIu Cell Sorter™ and were seeded at 30-50 cells per well in 96-well format to detect and pick single clones. Positive clones were expanded, qDNA was extracted and analyzed for successful HDR was determined using a custom designed TaqMan™ genotyping assay with a probe specific for the SNP (dbSNP ID: r563750215) located in Chr1:227,073,304 A>T. Selected clones were analyzed by Sanger sequencing to confirm correction of Chr1:227,073,304 location and discard possible insertions or deletions in the surrounding areas.

Fluorescence-Activated Cell Sorting (FACS)

Neural progenitors at day 12 of differentiation were dissociated with Accutase (Sigma-Aldrich) for 5 min at 37 C and inactivated in Neurobasal media. Cells were spun at 1000 rpm for 4 min and the pellets were resuspended in FACS buffer (DPBS, 0.5% BSA Fraction V-Solution, 100 U/mL Penicillin-Streptomycin, 0.5%. EDTA and 20 mM Glucose) with PE Mouse anti-human CD271 antibody (clone C40-1457, BD) at 1:100, also known as p75 or NGFR, and incubated for 20 min at room temperature (RT) in the dark. After the incubation time, cells were washed with FACS buffer and the pellet was resuspended in 2 mL of FACS buffer with 10 µM ROCK inhibitor (Y27632, Stemgent), p75 positive cells were purified in a BD FACSAria Hu Cell Sorter™ and data was analyzed using FlowJo™ software.

Real-Time Quantitative Polymerase Chain Reaction (RT-qPCR)

Human iPSC from PSEN2 mutants or control patients were grown in a monolayer and lysed directly in the cell culture wells with RLT buffer. Total RNA purification was performed with the RNeasy™ Micro kit (Qiagen), and was carried out according to the manufacturer's instructions. cDNA was synthesized using SuperScript™ III Reverse Transcriptase (RT) (Invitrogen, Carlsbad, Calif.). Semi-quantitative real-time PCR was performed on StepOne-Plus™ Real-Time PCR System (Applied Biosystems, Foster City, Calif.) using the primers listed in Table 2 below. We normalized expression levels to GAPDH. The PCR cycling parameters were: 50° C. for 2 min, 95° C. for 10 min, followed by 40 cycles of 95° C. for 15 s and 60° C. for 1 min. Each biological variable was assessed in technical triplicates within each designated "Experiment", and each designated "Experiment" was performed in at least three complete "start to finish" iterations. Expression levels were normalized to the control line, and results were expressed as AVG±SEM.

TABLE 2

| Gene | Forward Primer 5'-3' | SEQ ID NO | Reverse Primer 5'-3' | SEQ ID NO |
|---|---|---|---|---|
| BDNF | TAACGGCGGCAGAC AAAAAGA | 14 | GAAGTATTGCTTCAG TTGGCCT | 15 |
| BF1 | AGAAGAACGGCAA GTACGAGA | 16 | TGTTGAGGGACAGAT TGTGGC | 17 |
| Nkx2.1 | TAACGGCGGCAGAC AAAAAGA | 18 | GAAGTATTGCTTCAG TTGGCCT | 19 |
| NLRP2, ASB9 | From [77] | 20 | From [77] | 21 |
| NLRP3 | ACGAATCTCCGACC ACCACT | 22 | CCATGGCCACAACAA CTGAC | 23 |
| Tuj1 | GAAGTGTCCCAGGA CATGATAA | 24 | CTCTTGAGTAGCTGG GATTGAG | 25 |

Aβ Assays

Cells were conditioned for 3 days after day 8 of dual SMAD inhibition to measure secretion of Aβ by neural progenitors in vitro. Aβ levels were quantified using human/rat β amyloid 40 ELISA Kit and β amyloid 42 ELISA Kit high sensitive (Wako). Each biological variable was assessed using technical triplicates within each designated "Experiment", and each designated "Experiment" was performed in at least three complete "start to finish" iterations.

Immunostaining/ICC

Cells were fixed with PFA 4% directly on the wells of 12, 48 or 96 well plates for 20 min, washed 3 times with DPBS 1x(ThermoFisher). For the staining, cells were incubated in blocking solution (DPBS 1x with 0.1% Triton™ X-100 plus 5% Donkey serum) for two hours at room temperature. The corresponding primary antibodies were diluted at suitable concentration in blocking solution, and incubated overnight at 4 C. The primary antibodies used are represented in the table below. Cells were washed three times with DPBST (DPBS 1x+0.1% Triton™ X-100) and suitable secondary antibody was added in blocking solution for 1 h at room temperature. Then cells were washed three times with DPBST and incubated with DRAQ5 or Hoescht 33,342 (1 µg/mL, diluted in DPBS 1x) for 10 min at room temperature for nuclear counterstain. Cells were visualized using an inverted fluorescence microscope (Olympus™ IX71 microscope) or a confocal microscope (Zeiss™ LSMS Pascal microscope) under 10×, 20× or 63× magnification.

Western Blots

Human iPSC from PSEN2 mutants or control patients were grown in a monolayer and lysed directly in the cell culture wells with RIPA buffer (Thermo Scientific) with protease and phosphatase inhibitors. The protein concentration was measured using the BCA protein assay kit (Thermo Scientific). After protein estimation, 20 µg of cell lysate were separated by SDS-PAGE electrophoresis on a 4-12% Bis-Tris gel (Bolt™ protein gels) and transferred onto nitrocellulose membranes by electrophoresis blotting. The membranes were blocked with blocking buffer 1×TBST (tris-buffered saline +0.1% Tween) plus 5% nonfat dry milk for 1 h in agitation at room temperature and washed three times with TBST. After washing, membranes were incubated at 4° C. overnight in agitation, with the primary antibodies against NLRP2 (1:1000), PSEN2 (1:200) or β-actin (1:1000). After rinsing, the membranes were incubated with horseradish peroxidase (HRP)-conjugated suitable secondary antibodies for 1 h at room temperature. Finally, protein bands were visualized with a chemiluminescent reagent according to the manufacturer's instructions. β-actin was used as loading control.

Electrophysiology

Whole cell patch-clamp recordings were obtained from single neurons between differentiation days 38 and 55. Cells were seeded at low density onto plastic coverslips which were placed in a perfusion based enclosed recording chamber. Neurons were localized using differential interference contrast optics under an Olympus BX61WI microscope fitted with a Hamamatsu Orca™ $R^2$ CCD camera. Recordings were carried out at room temperature using MultiClamp™ 700 B amplifier (Molecular Devices, Sunnyvale, Calif., USA). Signals were sampled at 10 kHz and filtered at 6 kHz using a Digidata™ 1440 A analog to digital converter (Molecular Devices). Amplifier control and data acquisition was done using pClamp™ 10.0 software (Molecular Devices).

During recordings neurons were perfused with oxygenated Brainphys™ media (StemCell Technologies Inc). Medium resistance recording pipettes (4-6 MΩ) were filled with an intracellular solution consisting of (in mM) 130 K-gluconate, 10 KCl, 2 Mg-ATP, 0.2 Na-GTP, 0.6 CaCl2, 2 MgCl2, 0.6 EGTA, and 5 HEPES titrated to pH 7.1 and osmolarity of 310 mOsm. In some experiments, the intracellular solution also contained 4 mg/mL biocytin (Sigma-Aldrich) for post-hoc identification of individual neurons, which were visualized with streptavidin-conjugated Alexa 488 (Life Sciences) as described elsewhere [42]. After initial break-in, access resistance (Rs) was constantly monitored and recordings were discarded if Rs exceeded 20 MΩ or changed more than 30%. The voltage protocol for compound Na+ and K+ currents characterization was as follows: cells were held at −80 mV potential followed by 500 ms steps from −100 mV to 30 mV with 10 mV increment at a frequency of 0.1 Hz. Following transition to current-clamp mode, resting membrane potential was recorded and cells were hyperpolarized by a negative DC current injection to −70 mV to ensure consistency of excitability measurements. Action potentials were evoked with square 1 s current steps from −10 pA to 40 pA with 1 pA steps.

Electrophysiological recordings were analyzed using ClampFit™ software (Molecular Devices, Sunnyvale, Calif., USA) and statistical significance of the results was measured using ANOVA test with Tukey's post-hoc comparison of means. Salts and other reagents were purchased from Sigma-Aldrich (St. Louis, Mo., USA).

Statistical Analysis qPCR gene expression experiments and Aβ42/40 ELISAs were analyzed for statistical significance using Student t-test. LDH Release assays were analyzed by 2-Way ANOVA Bonferroni post hoc tests. ANOVA test with Tukey's post hoc comparisons were used for analysis of electrophysiology results. The experiments needed to study each of the 94 neurons recorded for electrophysiology analyses required days to weeks. On each experimental day, representatives from each genotype were included, with at least three samples from each genotype studied on each day. *, $p<0.05$; , $p<0.01$; *, $p<0.001$.

Results

Optimization of Protocol for BFCN Differentiation

The scheme of BFCN differentiation is described in FIG. 1A. iPSCs from control subjects or AD patients were plated iii feeder-free conditions and allowed to reach 100% confluency prior to differentiation using mTeSR1 basal media. Both branches of TGF-β signaling were inhibited (dual SMAD inhibition) to induce neuroectodermal fate on "day 0" [12]. Differentiations (day 2-10) were performed using a modified mTeSR1 formulation, lacking factors that support pluripotency (bFGF, TGF-β, Li—Cl, GABA and pipecolic acid). To specify these cells to basal forebrain cholinergic neurons, ventralization for medial ganglionic eminences (MGE) induction is required [19, 85, 91]. As such cells were treated with the Sonic Hedgehog (Shh) analog (SAG) at 500 nM and Purmorphamine at 2 µM from days 2 to 8. SAG is a suitable substitute to activate Shh signaling, as demonstrated during differentiation of ChAT+ motor neurons and glutamatergic interneurons [91], with lower cost than recombinant Shh and some advantages in neuronal survival properties over Shh itself [7, 35]. We used the Nkx2.1-GFP embryonic stem cell (ESC) reporter line as a tool to adjust the combination, dosage and timing of ventralizing agents more beneficial for specification of BFCNs from induced Nkx2.1 basal forebrain precursors.

However, given the potential of Nkx2.1 intermediate neural precursors to generate multiple neuronal subtypes, such as TH+ and GABA+ hypothalamic neurons, we analyzed the expression of the downstream cholinergic specification factor Lhx8 over expression of the GABAergic interneuron specific transcription factor Lhx6 [26] under different specification conditions (FIG. 1b). These data agree with those from [50] supporting the existence of a synergistic effect of SAG and purmorphamine on Nkx2.1 induction although an effect that is less than the effect of Shh plus purmorphamine (FIG. 1B). Nkx2.1-driven GFP levels were maintained after Day 14, even after withdrawal of SAG+ purmorphamine at day 8 (FIG. 1B). We observed higher Lhx8 induction upon SAG plus purmorphamine treatment than SAG alone, or even Shh plus purmorphamine (FIG. 1B). Interestingly, intermediate Nkx2.1 levels driven by SAG plus purmorphamine correlate with higher induction of Lhx8 and BF1 gene expression (FIG. 1B). Our choice of starting SHH pathway-driven ventralization at day 2 was based on reports demonstrating other MGE-derived populations being generated by earlier (e.g., hypothalamic neurons) or later (e.g., GABAergic interneurons.) ventralization in the context of dual smad inhibition protocols.

Following the patterning stage, we gradually switched from Custom mTESR1™ media to Brainphys™ media with B27 supplement to support neuronal survival and growth [3]. At day 11, we observed neural rosettes positive for Nestin and Sox2 markers (FIG. 1C); also, we observed Tuj1+ neurites as early as day 11 (FIG. 1C). To obtain cholinergic populations of a higher purity, we developed a P75+ FACS strategy to isolate progenitors specific for cholinergic neurons due to the fact that BFCNs are the only CNS neuron type to express robust levels of P75 under non-pathogenic conditions in the adult brain). Support for this strategy includes a previously published protocol using FACS to isolate high expressing P75+ cells from the embryonic murine septum [65]. This population correlated with best expression of cholinergic-related markers.

At day 11/12, we lifted the cells using chemical dissociation (Accutase) and purified day 11-12 p75+(CD271) neural progenitors and generated 3D neuronal embryoid bodies (NEBs) by spinning down neural progenitors in V-bottom 96 well plates. On day 19 NEBs were dissociated and re-plated as a monolayer on plates coated with branched polyethylenimine (Aldrich catalog number 408727) and laminin. Monolayer cultures were maintained with the addition of growth factors BDNF, NGF and DAPT until day 26, when cultures no longer had DAPT added. Immunostaining of both cryosections of NEB structures and fixed monolayers, resulting from chemical dissociation of NEBs from several control iPSC and H9 hESC lines, demonstrated expression of BFCN lineage markers Tuj1, MAP2, BF1, Nkx2.1 and p75, at final stages of the differentiation protocol (FIG. 1D). NGF addition to neuronal cultures showed an advantageous effect on maturation, neurite outgrowth and presence of ChAT (FIG. 1E).

Generation and QC of PSEN2$^{N141I}$ iPSC Lines

Figures 2A, 2B, 2C, 2D, 2E, 2F:
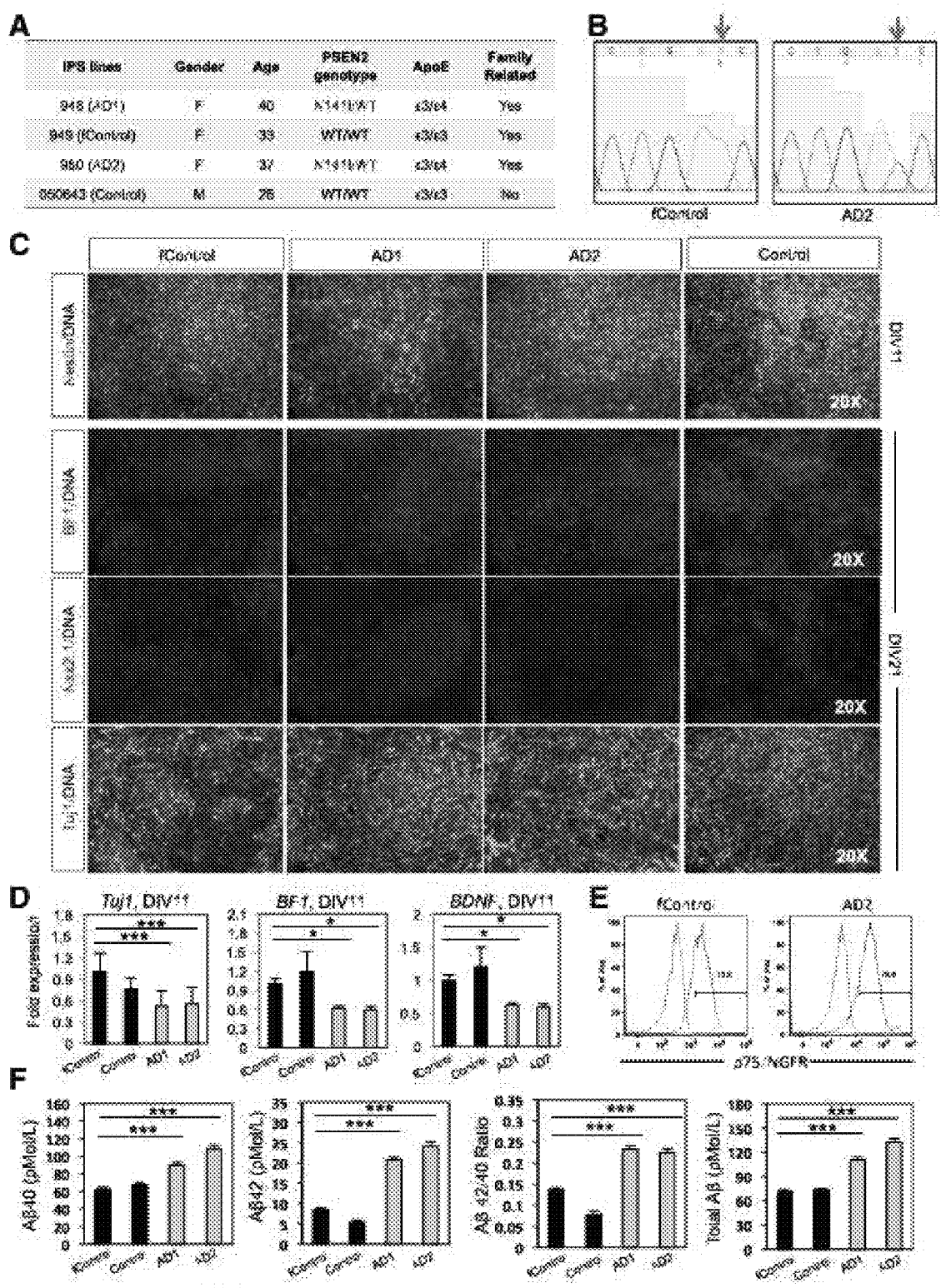
FIGS. 2A-2F. Basal cholinergic markers in PSEN2$^{N141I}$ neuroprecursors. (A) Table showing the cell lines used. Four iPS lines reprogrammed from fibroblasts were used; two controls (949 and 050643, labelled as fControl and Control, respectively) that do not carry the PSEN2$^{N141I}$ mutation nor the £4 allele; and two AD patients (948 and 950, labelled as AD1 and AD2, respectively) who carry the mutation and the £4 allele. Three of the four iPS lines were family related (fControl, AD1, and AD2). (B) Representative Sanger sequencing chromatograms showing a fragment of exon 5 of PSEN2. Arrow marks site of the missense point mutation Chr1:227,073,304 A>T. (C) Immunocytochemistry and RT-PCR for early neuronal and basal forebrain markers. n=3, 3 independent experiments with technical triplicates. (D) RTPCR fold changes for TUJ1 and BF1. n=3, 3 independent experiments with technical triplicates. (E) Representative histograms for P75 staining. n>6. (F) Aβ40 and Aβ42 ELISA quantifications. n=3, 3 independent experiments with technical triplicates. ***, p<0.001. *, p<0.05.
Figures 10A, 10B:
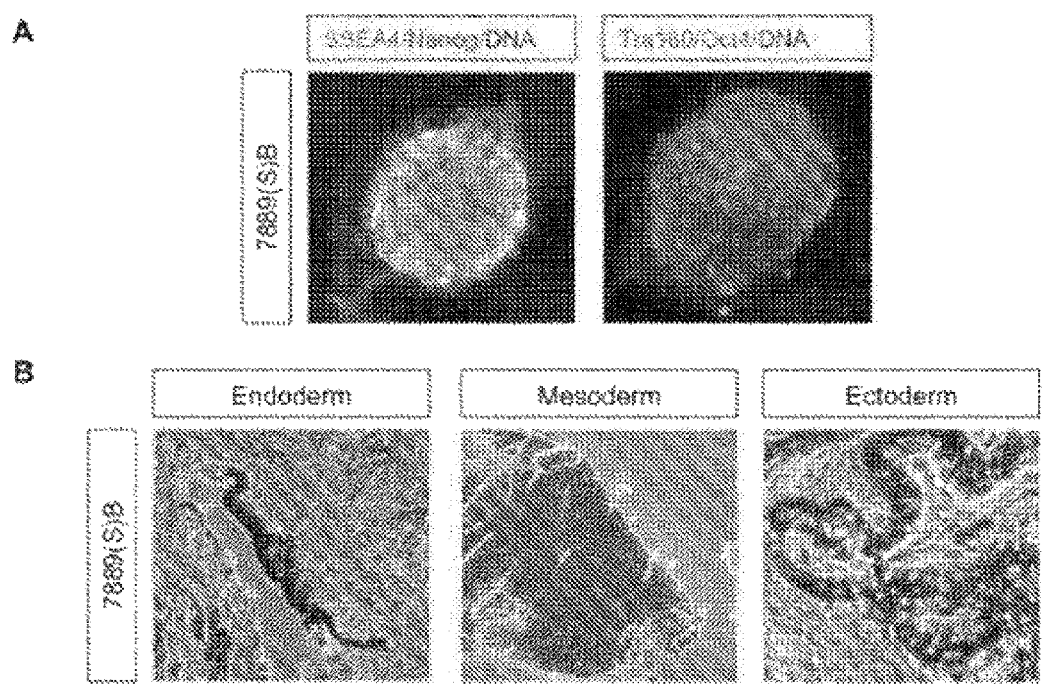
FIGS. 10A-10B. Quality control of iPSC lines. (A) Immunofluorescence shows expression of pluripotency markers SSEA4, Nanog, Tra160 and in 7889(S)B iPSC line. (B) Three germ layers (endoderm, mesoderm, and ectoderm) from teratomas generated by 7889(S)B iPSC line.

PSEN2$^{N141I}$ mutant iPSC and control lines were generated from fresh skin biopsies. Established fibroblast lines were grown from skin punches donated by a kindred of 2 carriers for presenilin 2 Volga familial AD mutation (PSEN2$^{N141I}$) and one non-affected member. Additionally, we included a non-family related control. Fibroblasts were reprogrammed using modified RNA method to introduce the Yamanaka factors (Oct4, KLF4, SOX2 and c-Myc), and the iPSC lines obtained were subject to several quality control processes to ensure robust cell-renewal and pluripotency, including alkaline-phosphatase (AP) enzymatic activity, gene expression analysis and immunostaining for pluripotency markers, as well as karyotyping for detection of chromosome abnormalities, following the automated iPSC reprogramming and QC methods developed by [60]. A summary of the genotypes, sex and age of the subjects included in the study is shown in FIG. 2a. The two PSEN2$^{N141I}$ iPSC lines were also heterozygous for APOE ε4 (ε3/ε4), whereas the control iPSC lines were homozygous ε3/ε3. The characterization of the iPSC lines, expression of pluripotency markers and quality control results are shown in FIG. 10. Briefly, all iPSC clones selected demonstrated pluripotency by embryoid body formation and differentiation into the three germ layers (FIG. 10A), incorporated herein by reference). Finally, the lines were fingerprinted (Cell Line Genetics) to ensure they matched the parental fibroblast lines (data not shown). All the parental fibroblast lines and the iPSC lines were subject to Sanger sequencing to determine PSEN2 and APOE genotypes. A 173 bp fragment from the exon 5 of PSEN2, surrounding the area where the PSEN2$^{N141I}$ point mutation is located (Chr1:227,073, 304 A>T), was amplified by PCR and sequenced using the primers published in [53]; similarly a fragment of 244 bp from APOE locus that contains two SNPs which determine the three allelic variants was amplified by PCR from genomic DNA, and subsequently sequenced to distinguish between ε2/ε3/ε4 variants, using the primers from [36]. Sample chromatograms showing the presence of PSEN2N141I point mutation are shown in FIG. 2B, and all genotypes are summarized in FIG. 2A.

Characterization of PSEN2$^{N141I}$ Neural Progenitors

To study the effect of the PSEN2$^{N141I}$ mutation in early stages of the differentiation of cholinergic neurons, we analyzed the neural progenitors (NPCs) obtained at DIV 11-16 along the BFCN differentiation protocol. The analysis of this intermediate immature population allows us to detect possible early alterations in the generation of BFCNs that would otherwise not be detected in terminally differentiated cholinergic neurons. Such defects could potentially play roles in mature neurons and contribute to the pathophysiology of AD. We analyzed the expression of early neuronal markers in PSEN2$^{N141I}$ mutant and control NPCs by gene expression and immunofluorescence methods. Although, we found a lower RNA expression of Tuj1 (βIII-Tubulin), a general neuronal marker, in mutant NPCs at day 11 of differentiation, we did not detected quantifiable differences by immunocytochemistry circa days 16-21, (FIGS. 2C and D). NPC monolayer cultures at day 11 were also immunostained for typical NPC markers: Sox2, and Pax6; with Pax6 levels dropping as expected along with Nkx2.1 induction (not shown). We observed comparable expression of Sox2 and Nestin in PSEN2$^{N141I}$ cultures at day 11 (FIG. 2C, top panel). At day 21, mutant NPCs expressed comparable levels of Nkx2.1 (MGE marker), but reduced levels of BF1 (forebrain marker) by qPCR; however, BF1 protein expression did not seem affected by immunostaining at this differentiation stage (FIG. 2C bottom panel, and D). We did not observe differences in the surface expression of NGFR (p75/CD271) in DIV11-12 PSEN2$^{N141I}$ cells, in terms of percentage of positive cells or fluorescence mean peak value (FIG. 2E).

As previously published by [59, 73], the expression of mutant PSEN2$^{N141I}$ causes an increase in the Aβ42/40 ratio in the brains of transgenic mice; additionally, this enhanced Aβ42 production was observed in neural cell lines upon induced overexpression of mutant PSEN2$^{N141I}$ protein [83] and in iPSC derived from PSEN2$^{N141I}$ mutant patients [93]. Consistently, we observed a 2-fold increase in the Aβ42/40 ratio, a 50% increase in the amount of secreted Aβ40 and 2.5-fold increase in Aβ42 species in the conditioned media from PSEN2N141' neural progenitors at DIV 11 (***p<0.001) (FIG. 2e). The levels of secreted Aβ40 and 42 observed in our study and the levels found in [93], using a different neuronal differentiation method applied to FAD1/PS2 iPSC lines derived from fibroblasts from the Coriell repository are very similar in both absolute number and in fold-increase.

Characterization of Mature BFCNs from PSEN2$^{N141I}$ iPSC Lines and Controls

Figures 3A, 3B:
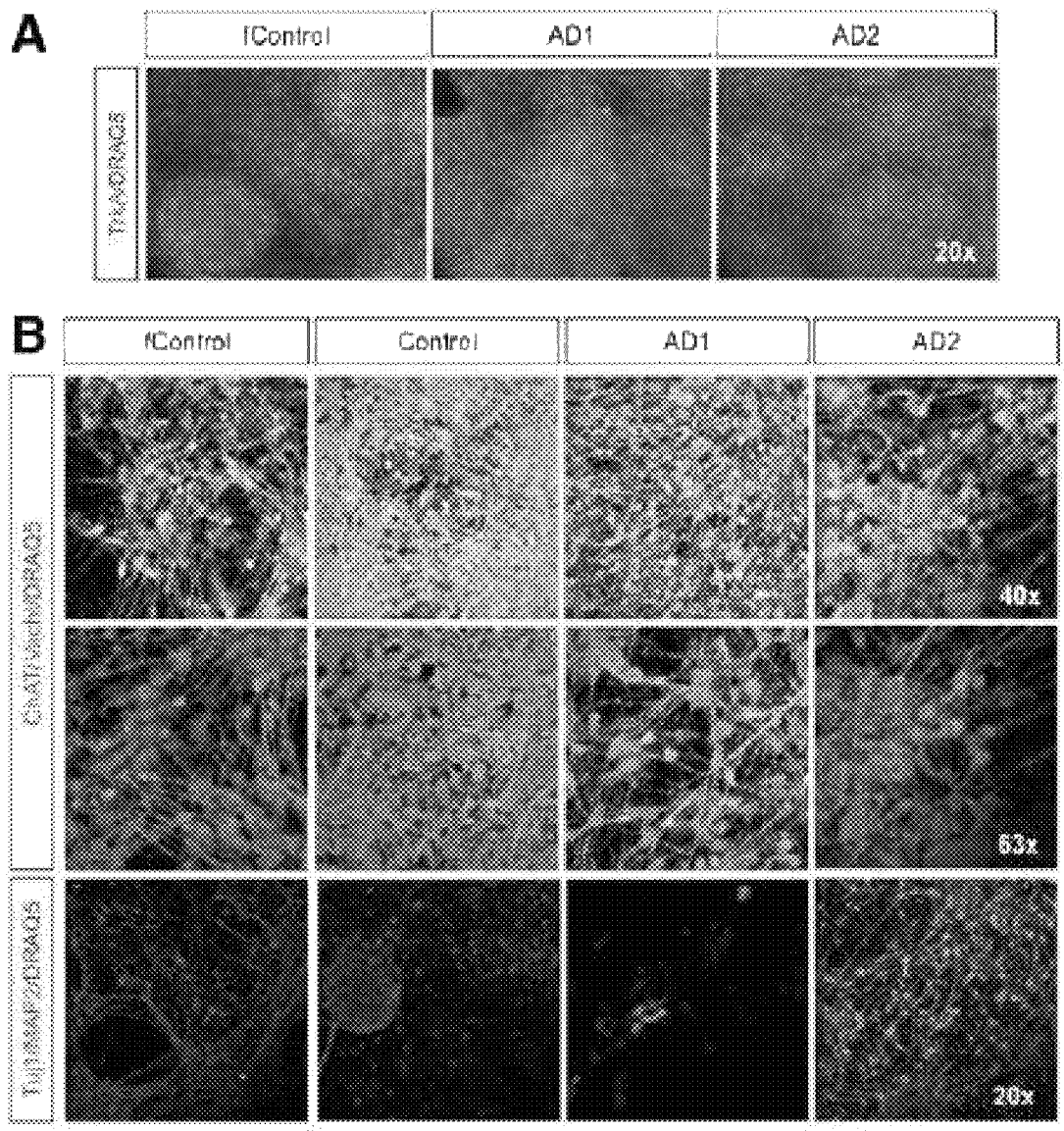
FIGS. 3A-3B. Neuronal and basal cholinergic markers by immunocytochemistry. (A) Immunostaining for TrkA on DIV 21. (B) Immunostainings for ChAT and vAChT at different magnifications at DIV65; and Tuj1 and MAP2. Images are representative of at least 3 independent experiments.

With the aim of determining the impact of PSEN2$^{N141I}$ mutation on the differentiation, gene expression, function, and communication of BFCNs, we characterized cells at later time points for appropriate expression markers; our goal was to explore whether PSEN2$^{N141I}$ iPSC were able to complete BFCN maturation process and if so, if any abnormalities along later stages of BFCN differentiation may account for the pathophysiology of EOFAD (FIG. 3). In addition to p75, which preferentially binds pro-NGF, we analyzed the expression of TrkA, the primary mature NGF receptor, was also expressed in PSEN2$^{N141I}$ BFCNs and control (FIG. 3a). This suggested that PSEN2$^{N141I}$ BFCNs are susceptible to receiving and benefiting from NGF pro-survival and differentiation signals as expected and further confirms their proper identity. We observed comparable expression of additional cholinergic neuron specific markers choline acetyltransferase (ChAT) and vesicular acetylcholine transporter (vAChT) in PSEN2$^{N141I}$ BFCNs and controls (FIG. 3b). Other general neuronal markers such as Tuj1, and the mature marker microtubule-associated protein 2 (MAP2) showed no apparent differences by immunofluorescence (FIG. 3b).

Figures 4A, 4B, 4C, 4D:
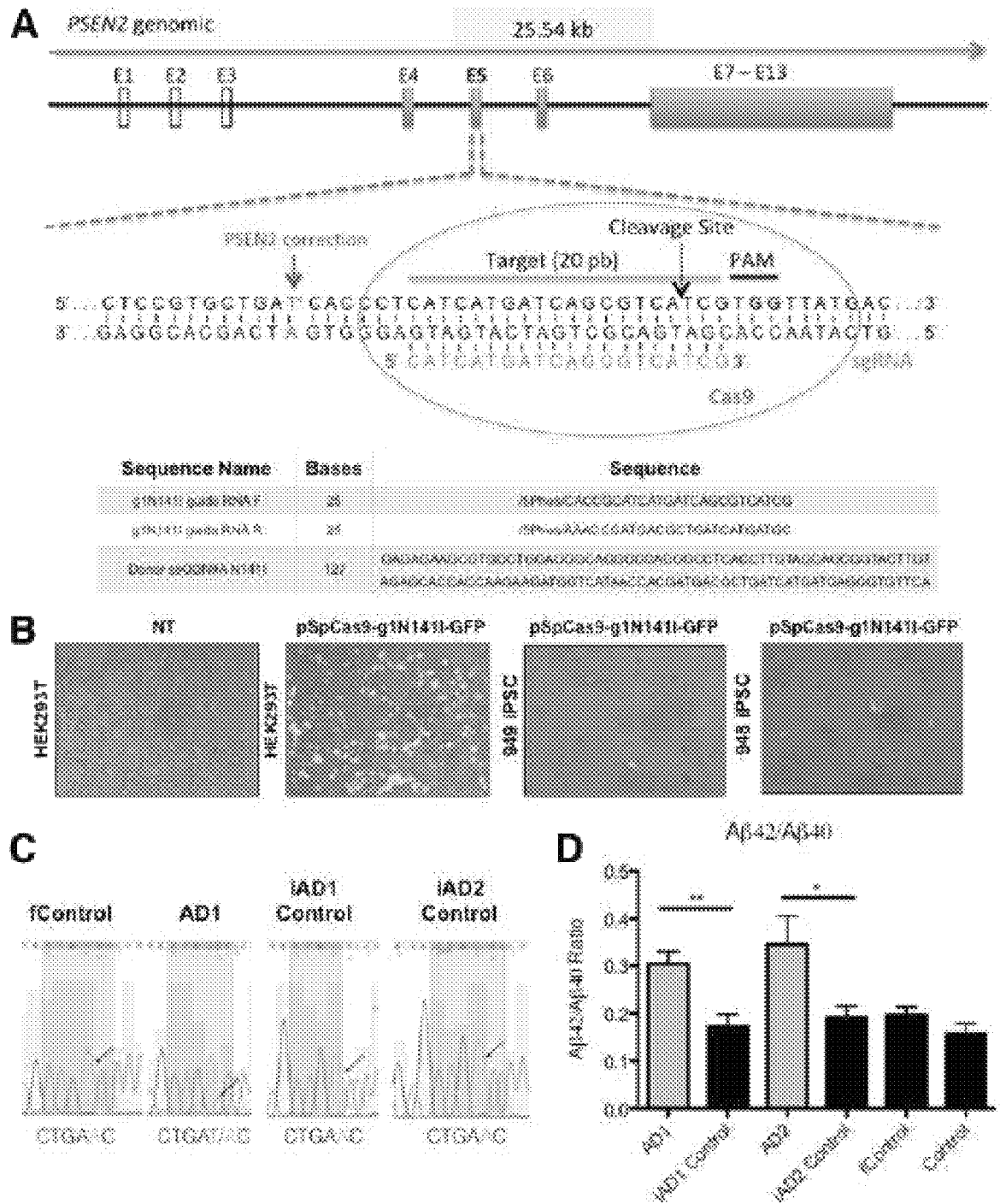
FIGS. 4A-4D. CRISPR/Cas9-mediated correction of PSEN2$^{N141I}$ iPS lines. (A) Schematic showing guide RNAs used in the targeting of CRISPR/Cas9, as well as donor ssODNs utilized to introduce wild-type genotype. Sequence identifiers from top to bottom: SEQ ID NOs: 26-31. (B) Left 2 panels show GFP positive HEK293T cells indicating Cas9 system with guide RNA expression, NT refers to non-transfected; right 2 panels show sample of GFP positive iPSCs after lipofection with pCas9-gN141I-GFP vector. (C) Sanger sequencing results from iPSC lines, showing corrections in the N141I mutation. (D) Aβ 42/40 ratio detected by ELISA in 72 h conditioned media from mutant, control or Cispr-Cas9 corrected BFCNs (DIV 34). n=4, 4 independent experiments with technical triplicates. *, p<0.05; **, p<0.01 Student T-test.

CRISPR/Cas9-Mediated Correction of PSEN2$^{N141I}$ Mutation and Effect on Aβ 42/40 Ratio To determine if the molecular alterations in the processing and cleavage of APP and/or the exacerbated activation of NLRP2 inflammasome, as previously observed in PSEN1 mutants [77], can be attributed to PSEN2$^{N141I}$ mutation only, we modified the PSEN2 locus in our iPSC lines employing CRISPR/Cas9 technology. We did this by correcting the PSEN2$^{N141I}$ point mutation in the two PSEN2 mutant iPSC lines (AD1, AD2). For this purpose, a specific guide RNA (g1N141I) was designed using an online tool (tools.genome-engineering.org) to direct Cas9 to the region of PSEN2 exon 5 surrounding PSEN2$^{N141I}$ mutation (23 bp upstream of Chr1:227,073,304 A>T). g1N141I was cloned into pSpCas9 (BB)-2A-GFP (PX458) vector. Expression was assessed by GFP fluorescence upon transfection of pSpCas9-g1N141I-GFP in HEK293T (FIG. 4a).

In order to correct the mutation, we designed an asymmetric ssODN HDR (homology directed repair) template, ssODN#A-N141I, with a long homology arm of 91 bp, and a short homology arm of 36 bp since asymmetrical donor sequences with a shorter arm oriented to the area closer to the PAM side demonstrated a superior efficiency of homology-directed repair using CRISPR/Cas9 system [13]. We then proceeded to trans-duce pSpCas9-g1N141I-GFP and ssODN #A-N141I into the iPSC lines using Amaxa™ nucleofection (FIG. 4a). Forty-eight hours post-nucleofection cells were dissociated and the GFP$^+$ population was purified by FACS and replated at low density feeder free for isolation of single gene-corrected clones (FIG. 4b). Subsequently, clones were grown and gDNA extracted post expansion. The screening of positive clones that demonstrated successful HDR was determined by qPCR using a custom designed TaqMan™ genotyping assay with a probe specific for the SNP (dbSNP ID: rs63750215) located in Chr1:227, 073,304 A>T. We were able to distinguish by this method between homozygous PSEN2$^{N141I}$ heterozygous PSEN2$^{N141I}$ and PSEN2$^{WT}$ single clones derived from the original iPSC lines, and pre-selected clones were subjected to Sanger sequencing to confirm Chr1:227,073,304 location and detect possible insertions, deletions or mismatches introduced by CRISPR/Cas9 modification in the surrounding area and corroborate successful HDR (FIG. 4c).

Figure 11B:
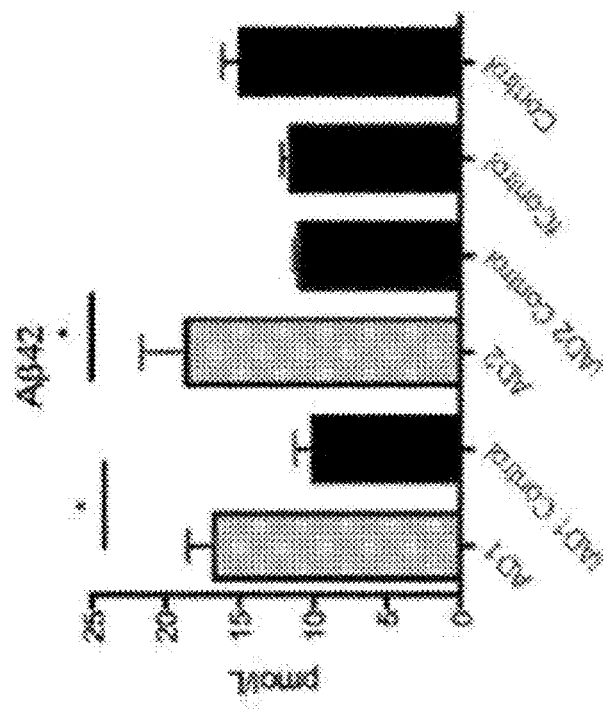
FIGS. 11A-11B. Amyloid β levels in mature BFCNs. (A) Levels of Aβ40 on BFCNs (DIV 34). *, P<0.01 vs. other lines in study according to One-Way ANOVA Bonferroni Post-hoc test. (B) Levels of Aβ42 on BFCNs (DIV 34). n=3, 3 independent experiments with technical triplicates. *, P<0.01 based on Student's T-test.
Figure 11A:
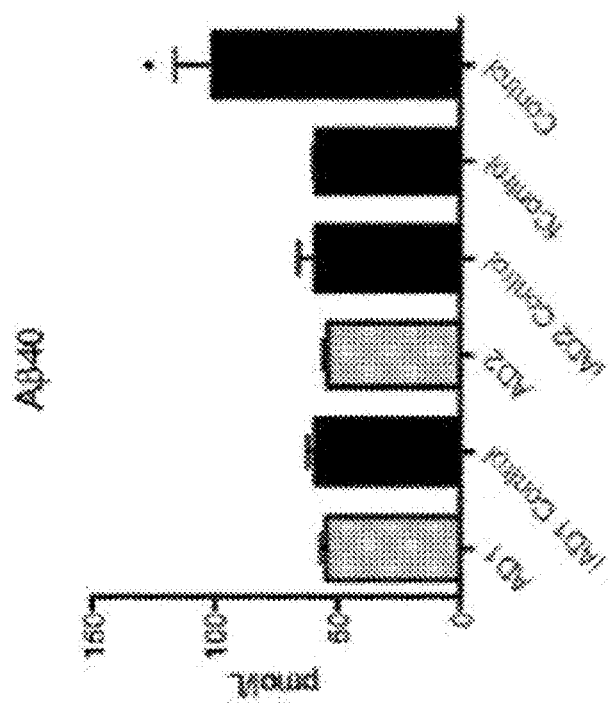

Successfully corrected clones were expanded and subjected to the BFCN differentiation protocol in parallel to the other 4 lines used in the study. We collected media from BFCNs (DIV 34) and re-tested for amyloid beta production. In support of our previous finding in NPCs at DIV11-12 (FIG. 20, we observed that mature BFCNs also display significant increases in Aβ42/40 ratio (FIG. 4d) and overall A3 production (FIG. 11). Importantly, these results also showed a normalization of Aβ42/40 ratio to control levels in corrected lines (iAD1 Control and iAD2 Control, are corrected clones of AD1 and AD2, respectively) (FIG. 4d). These results also strengthen previous findings linking the PSEN2$^{N141I}$ mutation to abnormal APP processing and reinforcing that presenilins contains the catalytic site of γ-secretase [90].

Figures 5A, 5B:
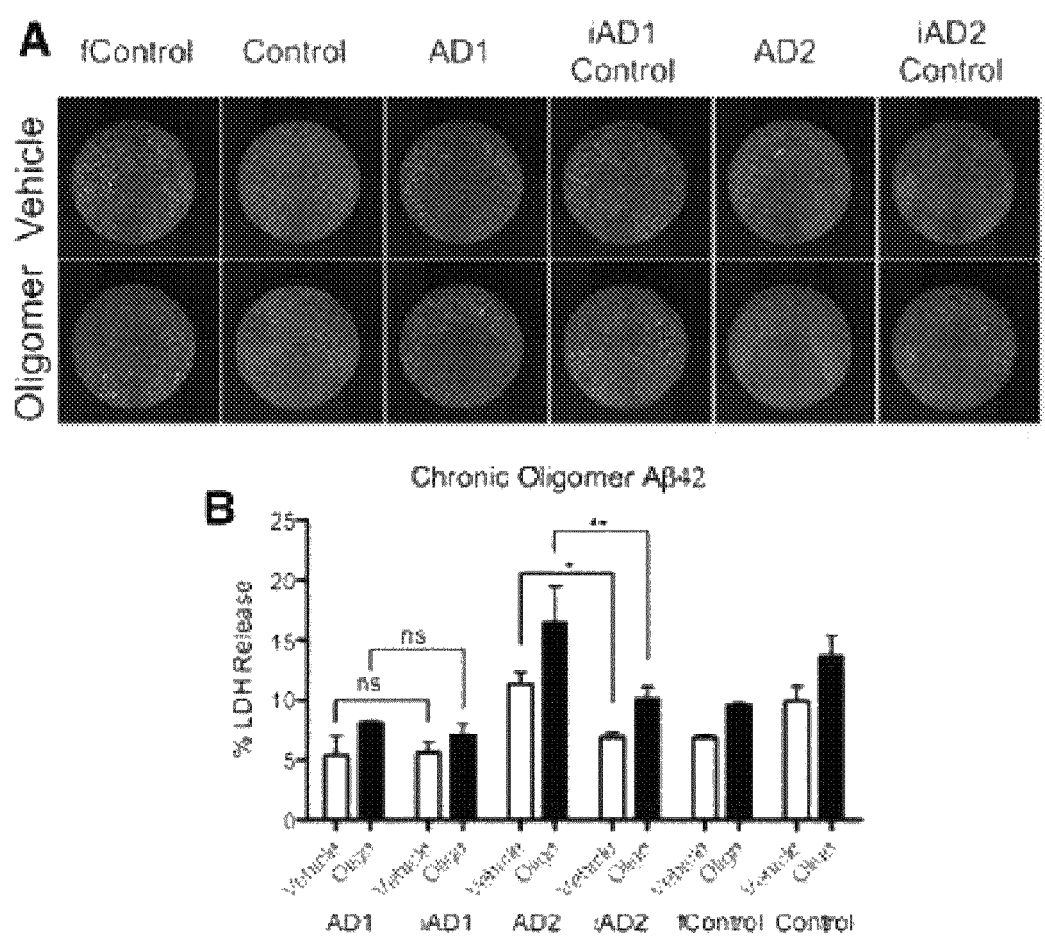
FIGS. 5A-5B. BFCNs carrying various PSEN mutations are not consistently more susceptible to Aβ42 oligomer toxicity. (A) Sample images of BFCNs from the indicated genotypes treated with propidium iodide to visualize cell death in response to 72-h exposure to Aβ42 oligomers (5 µM). (B) % LDH Release recorded from media collected after 72-h exposure. n=3, 3 independent experiments with technical triplicates. *, p<0.05; **, p<0.01 as detected by 2-Way ANOVA Bonferroni post hoc tests.

Assessment of Sensitivity to Aβ42 Oligomer Toxicity in iPSC-Derived PSEN2$^{N141I}$ Neurons Previous reports have shown that iPSC lines carrying FAD mutations may display an enhanced susceptibility to noxious stimuli, such as high concentrations of Aβ42 oligomers [2]. We therefore tested whether our BFCNs from PSEN2$^{N141I}$ mutants would display enhanced toxicity to Aβ42 oligomers in the media (FIG. 5). We assessed neurotoxicity by measuring the percentage of lactate dehydrogenase (LDH) released by dead cells, thus providing an indirect measurement for toxicity. Using this methodology by 2-way ANOVA we detected a significant effect in toxicity driven by 5 μM Aβ42 oligomer addition to the culture media, after 72-h exposure (***, $p<0.01$). Post hoc Bonferroni analysis revealed significant differences between the AD2 line and its corrected isogenic control (iAD2 Control). However, this apparent enhanced sensitivity to Aβ42 oligomer toxicity was not observed in the AD1 line and its corresponding control. These results indicate that differences in susceptibility to Aβ42 are not exclusively linked to mutant PSEN2 genotype, and that likely additional genetic factors different between AD1 and AD2 subjects affect susceptibility to this stress, further emphasizing the importance of multiple isogenic models.

Assessment of NLRP2 mRNA in iPSC-Derived PSEN2$^{N141I}$ Neurons

Figures 6A, 6B, 6C, 6D, 6E, 6F:
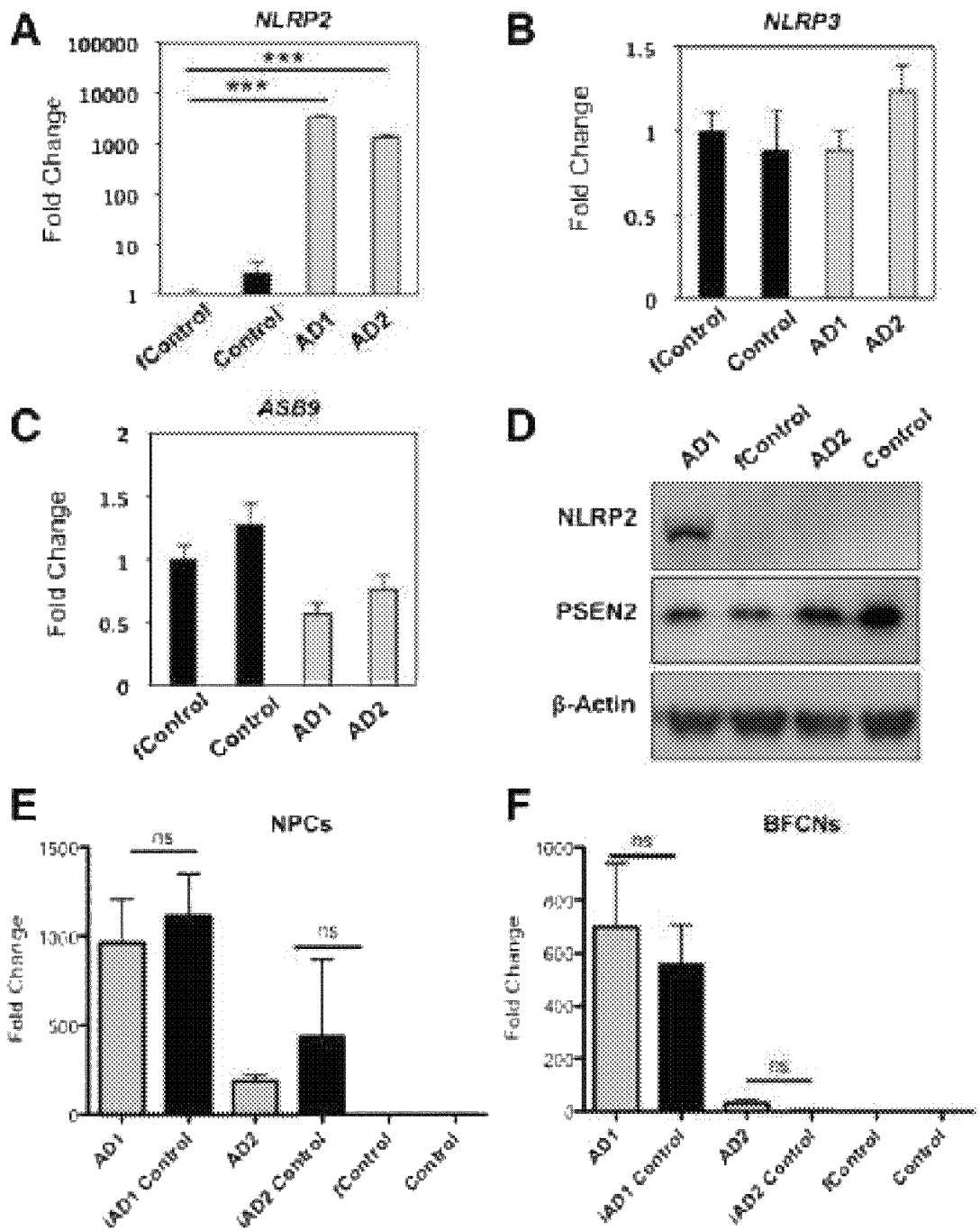
FIGS. 6A-6F. NLRP2 inflammasome mRNA levels are over-expressed in some PSEN2$^{N141I}$ cells, but it is not driven by mutation. RT-PCR expression of (A) NLRP2, (B) NLRP3, and (C) ASB9 in cholinergic neuroprecursors. (D) Western blot showing NLRP2, PSEN2 and 13-Actin. RT-PCR expression of NLRP2 in Neuroprecursors (E) and BFCNs (F). n=3, 3 independent experiments with technical triplicates, for all panels. ***, p<0.001.

We previously reported that NLRP2 mRNA was elevated in PSEN1 mutant iPSC and NPCs, [77] which was also the case for PSEN1 mutant cortical neurons (unpublished observation). Therefore, we wanted to analyze the status of the components of the inflammasome in the context of PSEN2$^{N141I}$ mutation. When we assayed by qPCR the mRNA levels of NLRP2 in NPCs at DIV12, we observed an increase over 100-fold in AD1 and AD2 lines, as compared to control lines (FIG. 6a). This correlated with a notable increase in NLRP2 protein, as observed by SDS-PAGE in whole cell lysates from day 11 PSEN2 mutants (FIG. 6d). Noticeably, however we did not detect bands for NLRP2 by immunoblot in the AD2 line lysates. Further, we were unable to corroborate some other transcriptional events previously seen in PSEN1 mutant iPS neural precursors, such as the elevated ASB9 that encodes an E3 ligase that directs mitochondrial creatine kinase for degradation. Instead, we observed a trend toward decreased levels in PSEN2 mutation carriers by 20-30%.

Assessment of Excitability of iPSC-Derived PSEN2$^{N141I}$ BFCNs

Figures 7A, 7B:
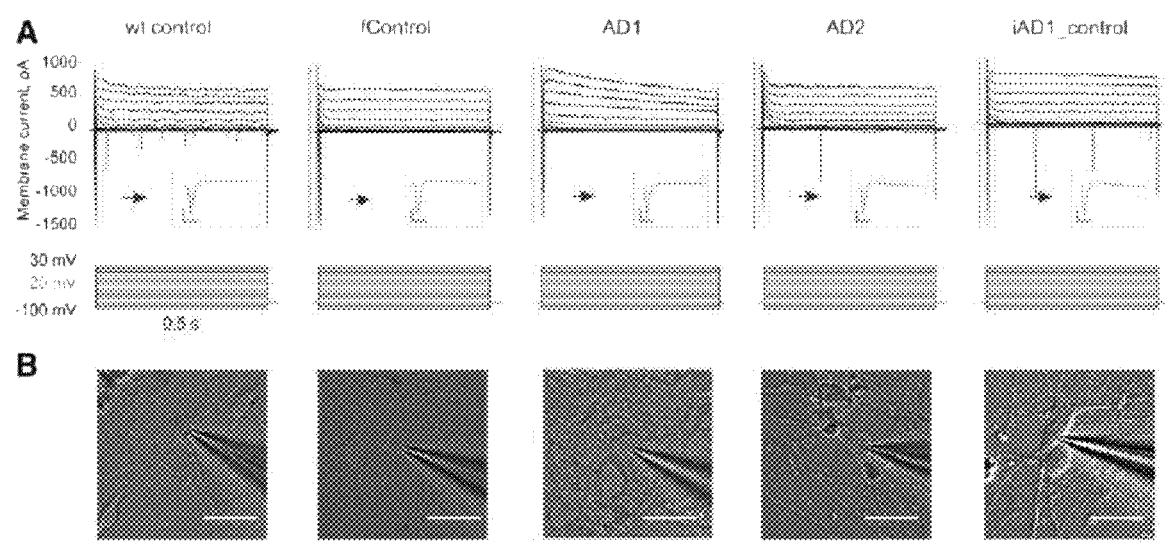
FIGS. 7A-7B. Electrophysiological and morphological features of BFCN. (A) Top row—compound sodium and potassium currents produced by a voltage protocol shown in bottom row. Current trace produced by a voltage step to −20 mV shown in red. Inset shows first 25 ms of a current produced by a voltage step to −20 mV (scale bars 200 pA, 5 ms). (B) Differential interference contrast image of a patched BFCN recorded in (A). Ninety-four neurons (22 wild-type control, 21 familial control, 18 AD1, 28 AD2 and 5 iAD1_control). Scale bar is 30 µm.

Using BFCN differentiation protocol, we were able to generate electrophysiologically active cholinergic neurons in a dish from two PSEN2$^{N141I}$ mutant AD patients, wild-type and familial controls starting from differentiation day 35. We were initially unable to obtain mature action potential waveforms from BFCNs grown in neurobasal media at this stage, but switching to Brainphys™ media significantly improved electrophysiological properties of cultured neurons [3]. These findings are in line with electrophysiological characterization of other iPSC generated neurons used to compare both media [3]. The benefits of the protocol containing Brainphys™ media in two additional cell lines (including the H9 embryonic stem cell line) with comparable endpoint expression of ChAT and VAChT as well as electrophysiological responses were repeated. In order to investigate the electrophysiological properties of BFCN, we recorded from a total of 94 neurons (22 wild-type control, 21 familial control, 18 AD1, 28 AD2 and 5 iAD1_control) using whole cell patch-clamp method. In all experimental groups, recorded neurons displayed voltage-activated currents through sodium and potassium ion channels, ability to generate action potentials and displayed classical neuronal morphologies (FIG. 7). In subset of experiments, recorded neurons were labeled with biocytin through a patch pipette, which allowed for post hoc cell identification and ICH characterization. We found that all biocytin-labelled cells were also immuno-positive for ChAT and VAChT (n=12, FIG. 8a).

Figures 9A, 9B, 9C, 9D:
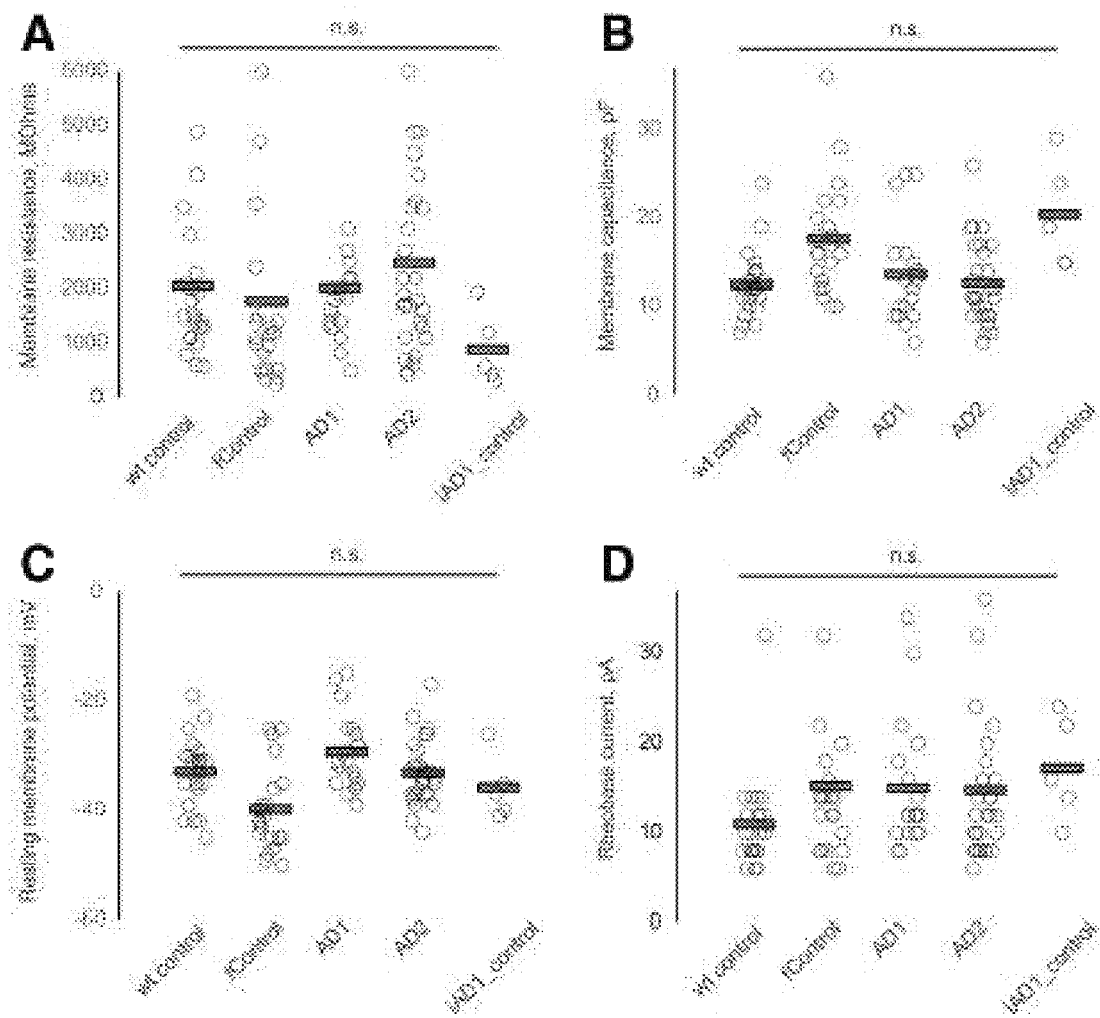
FIGS. 9A-9D. Intrinsic electrophysiological properties of BFCNs. Summary data on all recorded BFCNs from five groups. Ninety-four neurons (22 wild-type control, 21 familial control, 18 AD1, 28 AD2 and 5 iAD1_control). Histograms show individual values from each neuron (circle) and group means (bars) for membrane resistance (A), capacitance (B), resting potential (C) and rheobase current (D). Statistical significance was tested with ANOVA and Tukey's post hoc comparisons.

Significant differences between the groups in terms of neuronal membrane resistance and capacitance were not observed, membrane resting potential and the minimum current required for generation of a single action potential (FIG. 9). However, it was observed that there were significant mutation-related, editing-reversible differences in excitability of BFCNs.

Figures 8A, 8B, 8C:
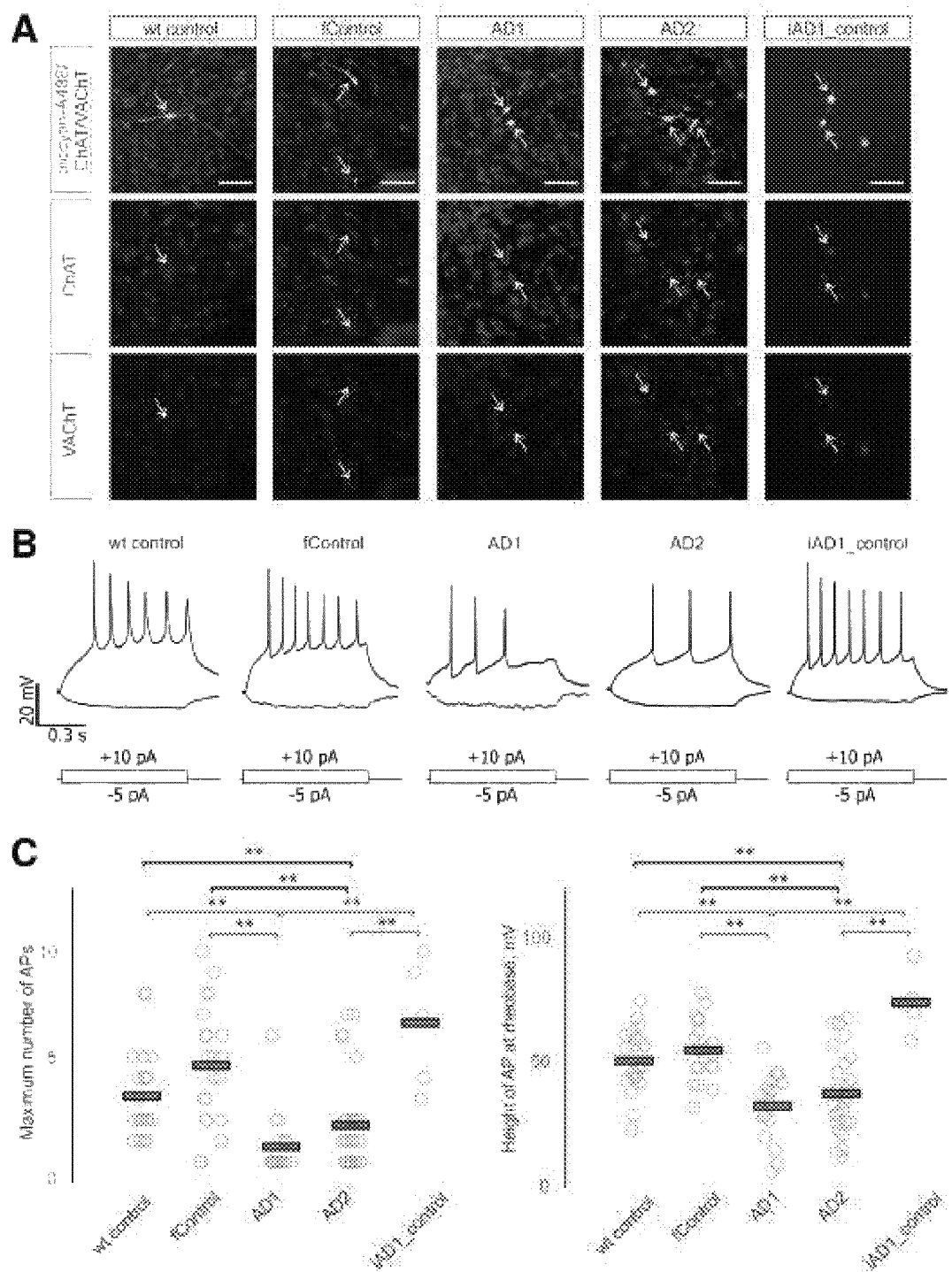
FIGS. 8A-8C. Electrophysiological deficits in BFCNs from AD lines. (A) Co-localization of biocytin-labelled neurons with cholinergic markers ChAT and VAChT. Arrows indicate positions of recorded neurons somas, scale bar is 50 µm. (B) Representative firing patterns of BFCNs produced by a 1 sec negative and positive square current injection are depicted. A grand total of 94 individual neurons were studied electrophysiologically: 22 wild-type control neurons, 21 familial control neurons, 18 AD1 neurons, 28 AD2 neurons, and 5 iAD1_(CRISPR-corrected) neurons. The experiments on the 94 neurons required days to weeks. On each experimental day, representatives from each genotype were included, with at least three samples from each genotype studied each day. (C) Summary data on maximum number of action potentials that neurons are capable of sustaining (left) and height of a single action potential at rheobase (right) across all conditions. Individual data points are shown as circles, group means are shown as bars. **, p<0.01 Tukey HSD test.

Neurons derived from AD1 and AD2 lines (as compared to WT and familial controls) were able to generate fewer maximum number of spikes in response to a square depolarizing current injection (ANOVA test with Tukey's post hoc comparisons, FIG. 8b, c). Height of the first action potential at rheobase current injection was also significantly decreased in AD1 and AD2 BFCNs (FIG. 1c). Importantly, CRISPR/Cas9 correction of the PSEN2 point mutation in the AD1 mutant iPSC line abolished the observed electrophysiological deficit, restoring both the maximal number of spikes and spike height to the levels recorded in wild-type and familial controls (ANOVA test with Tukey's post hoc comparisons, FIG. 8).

Discussion

There are 5 million people currently affected by Alzheimer's disease in the US and, according to the Alzheimer's Association, this number will increase to 16 million by the year 2050. Unfortunately, we only have direct evidence for genetic causation that accounts for 3-5% of these patients. This percentage encompasses the EOFAD variants, caused by inherited fully penetrant autosomal dominant mutations in the amyloid protein precursor (APP), or PSEN1, PSEN2 that constitute the γ-secretase apparatus [87], and changes in their function increases the production of Aβ42 oligomers and/or deposition of amyloid plaques.

After decades studying murine models of AD that do not fully recapitulate the pathophysiology of this disease in the human brain [5, 57, 58], a complementary new concept of AD modeling in vitro has emerged upon the breakthrough by [81] allowing adult human tissue reprogramming into iPSC using defined factors, and their subsequent in vitro differentiation into specific brain cell types.

BFCNs are one of the most vulnerable neuronal populations whose deterioration explains, in part, the cognitive decline in AD patients. Apart from the evidence for BFCN failure and atrophy, other studies have revealed that human embryonic stem cell-derived BFCNs transplanted into AD mouse models can be associated with improvement in the learning behavior of the implanted mouse [94]. These findings highlight the relevance of iPSC- and ESC-derived BFCNs as not only early clinical indicators but also as a potential strategy for subtype-specific cell-based therapy for AD [39]. In order to move this cell-based therapeutic strategy forward, there has been an urgent need for a refined differentiation protocol to generate human ESC- and/or iPSC-derived BFCNs.

Our first goal was to develop an improved protocol for the generation of BFCNs and intermediate neural progenitors (NPCs), followed by the use of these methods when differentiating cell lines from both control subjects and those harboring the PSEN2$^{N141I}$ mutation. Using fibroblasts isolated from 3 sisters, 2 carrying the PSEN2 mutation and displaying cognitive decline, with the third wild-type for the mutation, iPSCs were developed [60]. In order to approach the dissection of the fidelity of linkage of various phenotypes to the pathogenic mutation, we began by optimizing published BFCNs protocols [4, 17, 46, 50, 89] including the purification of an intermediate CD271$^+$ (p75) forebrain progenitor population by Fluorescence Activated Cell Sorting (FACS) to generate 3D ventralized neural embryoid bodies (vNEBs), which can be later dissociated to look at neuronal populations in a monolayer.

After induction of BFCN differentiation in these cell lines, we have analyzed: (1) capacity to generate Tuj1$^+$/BF1$^+$/ChAT$^+$ neurons in vitro; (2) expression of genes/proteins of interest related to neuronal differentiation or inflammation; (3) generation of soluble and oligomeric Aβ40 and 42; (4) electrophysiological (ePhys) properties; and (5) selective vulnerability of BFCNs to one or more innate or microenvironmental factors within or in close approximation to those cells.

Several studies in AD mouse models highlight electrophysiological defects associated to late stages of AD pathology. Synaptic function in the hippocampus was reduced in APP23 mouse models [70]. Similarly, cholinergic neurons from the prefrontal cortex of TgCRND8 mice are unable to sustain cholinergic excitation as compared to control mice [64]. Here we report deficient electrophysiological properties in PSEN2$^{N141I}$ iPSC-derived BFCNs in vitro. Notably, correction of this point mutation re-established neuronal excitability to the level of the control iPSC-derived neurons.

We have optimized an in vitro BFCN differentiation protocol from human iPSC, focusing on generating a homogeneous population of electrophysiologically active ChAT+/VAChT+ neurons in a reproducible and fast way. The innovations introduced to the protocol granted a homogeneous expression of Nkx2.1, a transcriptional marker for MGE subregions, as soon as day 8 and very robust by day 11, compared to day 20 suggested in previously published protocols [38]; in defined serum-free media conditions and without forcing overexpression of factors implicated in cholinergic fate. We were able to record mature action potentials in neurons from day 38 in culture, accompanying co-expression of cholinergic specific markers, which is an earlier time point as compared to other existing protocols using ES or iPSC [4, 17, 46, 50, 89]. Therefore, our protocol has potential application to high-throughput drug screening in homogeneous cholinergic cultures. In addition, the 3D structure of NEBs themselves if left undisassociated organoid form would also allow mechanistic analysis in a more physiological setting.

After applying this optimized protocol to PSEN2$^{N141I}$ mutant iPSC lines, we found an increase in Aβ42/40 ratio in the conditioned media. We did not observe any evident defects in the neuronal differentiation process and expression of BFCN markers. Interestingly, we observed a decrease on BDNF gene expression in PSEN2$^{N141I}$ NPCs, similar to results described in a report [18] wherein BDNF changes were observed in homozygous and heterozygous APP$^{Swe}$/PSEN1$^{M146V}$ mice. The two mutant lines are also carriers of one APOE ε4 allele. The presence of this allelic variant, the most common and well characterized risk factor polymorphism for LOAD [16], may modulate the age of onset and severity of the phenotype [49]. Therefore, these iPSC lines combining both the EOFAD PSEN2 Volga mutation (or CRISPR/Cas9 corrected) and APOE E4 allele constitute a tremendously useful tool to study the pathophysiology of early onset AD in vitro, especially when apoE-secreting iPSC-derived astrocytes are also present.

Searching for adjacent mechanisms or events that may be a cause or a consequence of elevated β-amyloid production, researchers have found overactivated inflammation and electrophysiological defects associated with AD mutations. The concept of these defects being independent from β-amyloid deposition and their demonstration using CRISPR/Cas9 technology to correct EOFAD mutations would open the debate to the need of combined AD treatments not only targeting β-amyloid plaques (Gandy et al., in press), but also to overcome parallel inflammatory processes or excitotoxicity/defective neuronal firing.

NLRPs are components of the inflammasome, which induces the secretion of mature pro-inflammatory cytokine IL-13 in response to pathogens and toxic stimuli [11, 41]. NLRP2 appears dysregulated in astrocytes [45, 51], and NLRP3 in microglia [34] in the context of Alzheimer's disease as well as in other neurological diseases like Parkinson's disease [14, 32]; additionally, NLRP2/3 are altered in pathologies that show comorbidity with AD: obesity, type-2 diabetes. We previously reported an unexpected association of elevated expression of the inflammasome gene NLRP2 in iPSC-derived neurons from banked fibroblasts from subjects harboring $PSEN1^{A246E}$ and $PSEN1^{M146L}$ mutations [77]. This association reminded us of the association of the inflammatory skin disease acne inversa (AI) with mutations in presenilin 1, nicastrin, APH-1 and PEN-2, raising in our minds the question of whether some γ-secretase component mutations might be associated not only with proamyloidogenic actions but also with proinflammatory mechanisms.

Despite our observations $PSEN2^{N141I}$ mutant cells had elevated NLRP2 compared to controls, we were not able to attribute this upregulation to the familial PSEN2 mutation, as gene correction did not significantly reduce NLRP2 levels. Our results suggest that, although inflammasome dysregulation may occur in the brains of EOFAD patients, there may be factors triggering this event apart from any effect of PSENs on inflammasome biology that are reflected in reprogrammed PSEN2 mutant cell lines. Some potential explanations for this PSEN2-independent NLRP2 upregulation include effects of the apoE4 allele present in both PSEN2 subjects (not preset in controls) or epigenetic effects on fibroblasts collected from the EOFAD subjects that are maintained through the reprogramming process.

Electrophysiological defects in neurons have been associated with PSEN1 and PSEN2 mutations. Some of these defects are attributed to altered function of voltage-gated K+ channels, potentially through the cleavage of channel components mediated by the PS/γ-secretase apparatus [44, 72]. Presenilin mutations also disrupt calcium signaling by increasing the levels of calcium stored in the endoplasmic reticulum that result in increased stimulus-induced released into the cytosol, rather than altered influx of calcium. One of the mechanisms behind neuronal calcium dysregulation was described in cortical neurons from $PSEN1^{M146V}$ mice, mediated by inositol triphosphate (IP3) [79]; and, more directly, the formation of dual function protein-ion channels by unprocessed PSEN1 and PSEN2 themselves, modulating the exit of calcium from the endoplasmic reticulum [29, 55, 80, 84]. Given the important role of presenilins on potassium and calcium flux and neuronal excitability, mutations in PSEN1 and PSEN2 may lead to reduced neuronal excitability and neurotoxicity. Mice carrying mutant forms of APP exhibited aberrant action potentials associated to a decrease in sodium currents with no alteration in potassium currents, only after plaque burden was considerable [9]. There is evidence that APP overexpression causes hyperexcitability in mouse cortical neurons [75, 86, 92].

Mucke and Selkoe [52] have highlighted a toxic effect of A3 resulting in synaptic and network dysfunction. In fibroblasts and neural cell lines, A3-mediated accumulation of mitochondrial $Ca^{2+}$ was elevated when mutant forms of PS1 were expressed [31]. Neuronal firing patterns in mouse hippocampal neurons were altered by exposure to A3 [67, 69]. A3 exposure was also associated with altered $K^+$ channel conductance in pyramidal neurons [54]. PSEN1 mutations have been observed to associate with altered $Ca^{2+}$ mitochondrial channels in the cerebellum, apparently causing reduced spike activity in Purkinje cells in the absence of amyloid plaque deposition [74]. Aβ42 may accentuate the defects present in $Ca^{2+}$ homeostasis by modulation of additional voltage-dependent ion channels [8, 25, 76, 88].

Apart from mouse data and immortalized neuronal cell lines, electrophysiological defects in iPSC-derived neurons upon exposure to A3 have been shown: hiPSC-derived cortical pyramidal neurons and GABAergic interneurons have deficient action potentials upon exposure to A3 [56], and neurons differentiated from hiPSC harboring $PS1^{A426E}$ mutation also showed deficient firing patterns [47]. However, there are no previously published data on characterization of electrophysiological properties of PSEN2 mutant iPSC-derived BFCNs.

Hyper- or hypoexcitatory effects and differences in firing frequency vary with the gene mutation and are highly dependent on the neuronal subtype [37, 48]. All these events may contribute to the progressive neurodegeneration present in the pathogenesis of AD, and we specifically document events that may account for the neuronal defects associated to early stages of EOFAD human pathogenesis. Here we report defective electrophysiological properties in iPSC-derived BFCNs that are specifically associated with the PSEN2N141I familial mutation. Interestingly, although some of the previous studies attribute this impairment in neuronal activity to the build-up of plaques in the brain of AD mice, we found a substantial impairment in the induced action potentials in the absence of amyloid plaques, solely in the presence of a discrete excess of Aβ42 oligomers in the culture media, consistent with other reports [18]. Correction of this point mutation re-established the firing patterns to those of the wildtype iPSC-derived neurons.

Modulators of potassium channels in neurons have proven efficacy in memory improvement in AD mouse models [44]. Modulation of $Ca^{2+}$ channels and excitotoxicity may open a new wave of AD drugs. Understanding the mechanism through which PSEN2 mutations affect the electrophysiological activity in different subsets of neuronal populations and unraveling the connection between PSEN2, other genetic modulatory factors and inflammation will potentially lead to, not only alternative symptomatic treatments, but also to novel drugs decreasing the $Ca^{2+}$-mediated vulnerability to ROS and potentially stopping the neuronal loss and progression of the disease, if administered at early stages.

It is clear that mutant presenilins alter neuronal excitability even before the formation of A3 plaques [18, 74]. One plausible hypothesis is that APP and presenilins may exert effects that modulate neuronal excitability through currently unrecognized mechanisms acting separate from their roles in the biogenesis of A3. Accumulation of A3 could synergize with the altered electrophysiological mechanisms in a pathway leading to AD. With the wealth of data supporting neuronal excitotoxicity as a key mechanism implicated in AD, further studies focusing on clarifying the possible role(s) of PSENs and/or Aβ in physiological or pathological events are warranted.

CONCLUSIONS

We have optimized an in vitro protocol to generate human BFCNs from iPSCs from presenilin 2 (PSEN2) mutation carriers and controls. As expected, PSEN2$^{N141I}$ was associated with an increase in the Aβ42/40 in iPSC-derived BFCNs, and this was reversed by CRISPR/Cas9-mediated gene editing. Unexpectedly, iPSC-derived BFCNs or cortical neurons from PSEN2$^{N141I}$ carriers showed diminished basal excitability as quantified by a reduction of both spike frequency and spike amplitude. This electrophysiological phenotype was also abolished following CRISPR/Cas9 correction of the PSEN2$^{N141I}$ mutation. The gene editing data confirm that there was a robust consistency of mutation-related changes that characterized all the expected findings and genotypes from all cells.

Abbreviations

AD: Alzheimer's disease;
ApoE: Apolipoprotein E;
APP: Amyloid protein precursor;
AVG: Average; Aβ: Amyloid beta;
BDNF: Brain derived neurotrophic factor;
BF1: Brain factor 1;
BFCNs: Basal forebrain cholinergic neurons;
ChAT: Acetylcholine transferase;
DAPT: (N-[N-(3,5-difluorophenacetyl)-L-alanyl]-S-phenylglycine t-butyl ester);
DIV: Days in vitro;
DNA: Deoxyribonucleic acid;
DPBS: Dulbecco's phosphate-buffered saline;
DPBST: Dulbecco's phosphate-buffered saline+0.1% Triton X-100;
EGTA: Ethylene-bis(oxyethylenenitrilo)tetraacetic acid;
EOFAD: Early onset familial Alzheimer's disease;
ESC: Embryonic stem cells;
FACS: Fluorescence-activated cell sorting;
GAPDH: Glyceraldehyde-3-phosphate dehydrogenase;
GFP: Green fluorescent protein;
HDR: Homology directed repair;
HFIP: 1,1,1,3,3,3-hexafluoro-2-propanol;
HRP: horseradish peroxidase;
IPSCs: Induced pluripotent stem cells;
LDH: Lactate dehydrogenase;
MAP2: Microtubule-associated protein 2;
MGE: Medial ganglionic eminences;
NEBs: Neuronal Embryoid Bodies;
NGF: Nerve growth factor;
NLRP2: NLR family pyrin domain containing 2;
NPC: Neural progenitor cells;
PFA: Paraformaldehyde;
PSEN: Presenilin;
RNA: Ribonucleic acid;
Rock: Rho-associated, coiled-coil containing protein kinase;
RT: Reverse Transcriptase;
RT-qPCR: Real-time quantitative polymerase chain reaction;
SAG: Smoothened agonist;
SDS-PAGE: Sodium dodecyl sulfate polyacrylamide gel electrophoresis;
SEM: Standard error of the mean;
sgRNA: Single guide RNA;
Shh: Sonic hedgehog;
SNP: Single nucleotide polimorfism;
ssODN: Single stranded oligonucleotides;
TBST: Tris-buffered saline+0.1% Tween;
VACht: Vesicular acetylcholine transporter;
WT: Wild type

REFERENCES (EACH ARE INCORPORATED HEREIN BY REFERENCE)

1. Arendt T, Bigl V, Arendt A, Tennstedt A (1983) Loss of neurons in the nucleus basalis of Meynert in Alzheimer's disease, paralysis agitans and Korsakoff's disease. Acta Neuropathol 61:101-108
2. Armijo E, Gonzalez C, Shahnawaz M, Flores A, Davis B, Soto C (2017) Increased susceptibility to Aβ toxicity in neuronal cultures derived from familial Alzheimer's disease (PSEN1$^{A246E}$) induced pluripotent stem cells. Neurosci Lett 639:74-81. doi:10.1016/j.neulet.2016.12.060
3. Bardy C, van den Hurk M, Eames T, Marchand C, Hernandez R V, Kellogg M, Gorris M, Galet B, Palomares V, Brown J, Bang A G, Mertens J, Bohnke L, Boyer L, Simon S, Gage F H (2015) Neuronal medium that supports basic synaptic functions and activity of human neurons in vitro. Proc Natl Acad Sci USA 112:E2725-E2734. doi:10.1073/pnas.1504393112
4. Bissonnette C J, Lyass L, Bhattacharyya B J, Belmadani A, Miller R J, Kessler J A (2011) The controlled generation of functional basal forebrain cholinergic neurons from human embryonic stem cells. Stem Cells 29:802-811. doi:10. 1002/stem.626
5. Borchelt D R, Ratovitski T, van Lare J, Lee M K, Gonzales V, Jenkins N A, Copeland N G, Price D L, Sisodia S S (1997) Accelerated amyloid deposition in the brains of transgenic mice coexpressing mutant presenilin 1 and amyloid precursor proteins. Neuron 19:939-945. doi:10.1016/S0896-6273(00)80974-5
6. Bowen D M, Smith C B, White P, Davison A N (1976) Neurotransmitter-related enzymes and indices of hypoxia in senile dementia and other abiotrophies. Brain 99:459-496
7. Bragina O, Sergejeva S, Serg M, 2arkovsky T, Maloverjan A, Kogerman P, 2arkovsky A (2010) Smoothened agonist augments proliferation and survival of neural cells. Neurosci Lett 482:81-85. doi:10.1016/j.neulet.2010.06.068
8. Briggs C A, Schneider C, Richardson J C, Stutzmann G E (2013) Beta amyloid peptide plaques fail to alter evoked neuronal calcium signals in APP/PS1 Alzheimer's disease mice. Neurobiol Aging 34:1632-1643. doi:10.1016/j. neurobiolaging.2012.12.013
9. Brown J T, Chin J, Leiser S C, Pangalos M N, Randall A D (2011) Alleged intrinsic neuronal excitability and reduced Na+ currents in a mouse model of Alzheimer's disease. Neurobiol Aging 32:2109.e1-2109.e14. doi: 10.1016/j. neurobiolaging.2011.05.025
10. Brueggen K, Dyrba M, Barkhof F, Hausner L, Filippi M, Nestor P J, Hauenstein K, Klöppel S, Grothe M J, Kasper E, Teipel S J (2015) Basal forebrain and hippocampus as predictors of conversion to Alzheimer's disease in patients with mild cognitive impairment—a multicenter DTI and Volumetry study. J Alzheimers Dis 48:197-204. doi:10.3233/JAD-150063
11. Bruey J M, Bruey-Sedano N, Newman R, Chandler S, Stehlik C, Reed J C (2004) PAN1/NALP2/PYPAF2, an inducible inflammatory mediator that regulates NF-kappaB and caspase-1 activation in macrophages. J Biol Chem 279: 51897-51907. doi:10.1074/jbc.M406741200
12. Chambers S M, Fasano C A, Papapetrou E P, Tomishima M, Sadelain M, Studer L (2009) Highly efficient neural conversion of human E S and iPS cells by dual inhibition of SMAD signaling. Nat Biotechnol 27:275-280. doi: 10.1038/nbt.1529
13. Chu V T, Weber T, Wefers B, Wurst W, Sander S, Rajewsky K, Kuhn R (2015) Increasing the efficiency of homology-directed repair for CRISPR-Cas9-induced precise gene editing in mammalian cells. Nat Biotechnol 33:543-548. doi:10.1038/nbt.3198
14. Codolo G, Plotegher N, Pozzobon T, Brucale M, Tessari I, Bubacco L, de Bernard M (2013) Triggering of inflammasome by aggregated α-synuclein, an inflammatory response in synucleinopathies. PLoS One 8:e55375. doi: 10.1371/journal.pone.0055375
15. Cong L, Ran F A, Cox D, Lin S, Barretto R, Habib N, Hsu P D, Wu X, Jiang W, Marraffini L A, Zhang F (2013) Multiplex genome engineering using CRISPR/Cas systems. Science 339:819-823. doi:10.1126/science.1231143
16. Corder E H, Saunders A M, Strittmatter W J, Schmechel D E, Gaskell P C, Small G W, Roses A D, Haines J L, Pericak-Vance M A (1993) Gene dose of apolipoprotein E type 4 allele and the risk of Alzheimer's disease in late onset families. Science 261:921-923
17. Crompton L A, Byrne M L, Taylor H, Kerrigan T L, Bru-Mercier G, Badger J L, Barbuti P A, Jo J, Tyler S J, Allen S J, Kunath T, Cho K, Caldwell M A (2013) Stepwise, non-adherent differentiation of human pluripotent stem cells to generate basal forebrain cholinergic neurons via hedgehog signaling. Stem Cell Res 11:1206-1221. doi:10.1016/j.scr.2013.08.002
18. Cummings D M, Liu W, Portelius E, Bayram S, Yasvoina M, Ho S-H, Smits H, Ali S S, Steinberg R, Pegasiou C-M, James O T, Matarin M, Richardson J C, Zetterberg H, Blennow K, Hardy J A, Salih D A, Edwards F A (2015) First effects of rising amyloid-3 in transgenic mouse brain: synaptic transmission and gene expression. Brain 138:1992-2004. doi:10.1093/brain/awv127
19. Danjo T, Eiraku M, Muguruma K, Watanabe K, Kawada M, Yanagawa Y, Rubenstein J L R, Sasai Y (2011) Subregional specification of embryonic stem cell-derived ventral Telencephalic tissues by timed and combinatory treatment with extrinsic signals. J Neurosci 31:1919-1933. doi:10.1523/JNEUROSCI.5128-10.2011
20. Davies P, Maloney A J (1976) Selective loss of central cholinergic neurons in Alzheimer's disease. Lancet (London, England). 2:1403
21. Davis K L, Mohs R C, Davis B M, Horvath T B, Greenwald B S, Rosen W G, Levy M I, Johns C A (1983) Oral physostigmine in Alzheimer's disease. Psychopharmacol Bull 19:451-453 22. De Strooper B After Solanezumab: Where Should Alzheimer's Research Go?|ALZFORUM. 2017
23. Echeverria V, Berman D E, Arancio O (2007) Oligomers of beta-amyloid peptide inhibit BDNF-induced arc expression in cultured cortical neurons. Curr Alzheimer Res 4:518-521
24. Epelbaum S, Genthon R, Cavedo E, Habert M O, Lamari F, Gagliardi G, Lista S, Teichmann M, Bakardjian H, Hampel H, Dubois B (2017) Preclinical Alzheimer's disease: a systematic review of the cohorts underlying the concept. Alzheimers Dement. doi:10.1016/j.jalz.2016.12.003
25. Etcheberrigaray R, Ito E, Kim C S, Alkon D L (1994) Soluble beta-amyloid induction of Alzheimer's phenotype for human fibroblast K+ channels. Science 264:276-279
26. Flandin P, Zhao Y, Vogt D, Jeong J, Long J, Potter G, Westphal H, Rubenstein J L R (2011) Lhx6 and Lhx8 coordinately induce neuronal expression of Shh that controls the generation of interneuron progenitors. Neuron 70:939-950. doi:10.1016/j.neuron.201 1.04!020
27. Francis P T, Palmer A M, Snape M, Wilcock G K (1999) The cholinergic hypothesis of Alzheimer's disease: a review of progress. J Neurol Neurosurg Psychiatry 66:137-147. doi:10.1136/JNNP.66.2.137
28. Gamzu E R, Thal L J, Davis K L (1990) Therapeutic trials using tacrine and other cholinesterase inhibitors. Adv Neurol 51:241-245
29. Gandy S, Doeven M K, Poolman B (2006) Alzheimer disease: presenilin springs a leak. Nat Med 12:1121-1123. doi:10.1038/nm1006-1121
30. Goulburn A L, Alden D, Davis R P, Micallef S J, Ng E S, Yu Q C, Lim S M, Soh C-L, Elliott D A, Hatzistavrou T, Bourke J, Watmuff B, Lang R J, Haynes J M, Pouton C W, Giudice A, Trounson A O, Anderson S A, Stanley E G, Elefanty A G (2011a) A targeted NKX2.1 human embryonic stem cell reporter line enables identification of human basal forebrain derivatives. Stem Cells 29:462-473. doi:10.1002/stem.587
31. Guo Q, Fu W, Holtsberg F W, Steiner S M, Mattson M P (1999) Superoxide mediates the cell-death-enhancing action of presenilin-1 mutations. J Neurosci Res 56:457-470. doi:10.1002/(SICI)1097-4547(19990601)56:5<457::AID-JNR2>3.0.CO;2-P
32. Gustot A, Gallea J I, Sarroukh R, Celej M S, Ruysschaert J-M, Raussens V (2015) Amyloid fibrils are the molecular trigger of inflammation in Parkinson's disease. Biochem J 471:323-333. doi:10.1042/BJ20150617
33. Hager K, Baseman A S, Nye J S, Brashear H R, Han J, Sano M, Davis B, Richards H M (2014) Effects of galantamine in a 2-year, randomized, placebo-controlled study in Alzheimer's disease. Neuropsychiatr Dis Treat 10:391-401. doi:10.2147/NDT.S57909
34. Halle A, Hornung V, Petzold G C, Stewart C R, Monks B G, Reinheckel T, Fitzgerald K A, Latz E, Moore K J, Golenbock D T (2008) The NALP3 inflammasome is involved in the innate immune response to amyloid-Nat Immunol 9:857-865. doi:10.1038/ni.1636
35. Heine V M, Griveau A, Chapin C, Ballard P L, Chen J K, Rowitch D H (2011) A small-molecule smoothened agonist prevents Glucocorticoid-induced neonatal Cerebellar injury. Sci Transl Med 3:105ra104. doi:10.1126/scitranslmed.3002731
36. Hixson J E, Vernier D T (1990) Restriction isotyping of human apolipoprotein E by gene amplification and cleavage with HhaI. J Lipid Res 31:545-548. doi:10.0000/PMID2341813
37. Hoxha E, Boda E, Montarolo F, Parolisi R, Tempia F (2012) Excitability and synaptic alterations in the cerebellum of APP/PS1 mice. PLoS One 7:e34726. doi:10.1371/journal.pone.0034726
38. Hu Y, Qu Z, Cao S, Li Q, Ma L, Krencik R, Xu M, Liu Y (2016) Directed differentiation of basal forebrain cholinergic neurons from human pluripotent stem cells. J Neurosci Methods 266:42-49. doi:10.1016/j.jneumeth.2016.03.017
39. Hunsberger J G, Rao M, Kurtzberg J, Bulte J W M, Atala A, LaFerla F M, Greely H T, Sawa A, Gandy S, Schneider L S, Doraiswamy P M (2016) Accelerating stem cell trials for Alzheimer's disease. Lancet Neurol 15:219-230. doi: 10.1016/51474-4422(15)00332-4

40. Jack C R, Wiste H J, Weigand S D, Knopman D S, Lowe V, Vemuri P, Mielke M M, Jones D T, Senjem M L, Gunter J L, Gregg B E, Pankratz V S, Petersen R C (2013) Amyloid-first and neurodegeneration-first profiles characterize incident amyloid PET positivity. Neurology 81:1732-1740. doi:10.1212/01.wnl.0000435556.21319.e4

41. Kinoshita T, Wang Y, Hasegawa M, Imamura R, Suda T (2005) PYPAF3, a PYRIN-containing APAF-1-like protein, is a feedback regulator of caspase-1-dependent interleukin-1beta secretion. J Biol Chem 280:21720-21725. doi:10.1074/jbc.M410057200

42. Kruglikov I, Rudy B (2008) Perisomatic GABA release and thalamocortical integration onto neocortical excitatory cells are regulated by neuromodulators. Neuron 58:911-924. doi:10.1016/j.neuron.2008.04.024

43. Levy-Lahad E, Wasco W, Poorkaj P, Romano D, Oshima J, Pettingell W, Yu C, Jondro P, Schmidt S, Wang K et al (1995) Candidate gene for the chromosome 1 familial Alzheimer's disease locus. Science 269:973-977. doi:10.1126/science.7638622

44. Liu D, Pitta M, Lee J-H, Ray B, Lahiri D K, Furukawa K, Mughal M, Jiang H, Villarreal J, Cutler R G, Greig N H, Mattson M P (2010) The KATP channel activator diazoxide ameliorates amyloid- and tau pathologies and improves memory in the 3xTgAD mouse model of Alzheimer's disease. J Alzheimers Dis 22:443-457. doi:10.3233/JAD-2010-101017

45. Liu L, Chan C (2014) The role of inflammasome in Alzheimer's disease. Ageing Res Rev 15:6-15. doi:10.1016/j.arr.2013.12.007

46. Liu Y, Weick J P, Liu H, Krencik R, Zhang X, Ma L, Zhou G, Ayala M, Zhang S-C (2013) Medial ganglionic eminence-like cells derived from human embryonic stem cells correct learning and memory deficits. Nat Biotechnol 31:440-447. doi:10.1038/nbt.256

47. Mahairaki V, Ryu J, Peters A, Chang Q, Li T, Park T S, Burridge P W, Talbot C C, Asnaghi L, Martin L J, Zambidis E T, Koliatsos V E, Koliatsos V E (2014) Induced pluripotent stem cells from familial Alzheimer's disease patients differentiate into mature neurons with amyloidogenic properties. Stem Cells Dev 23:2996-3010. doi:10.1089/scd.2013.0511

48. Marcantoni A, Raymond E F, Carbone E, Marie H (2014) Firing properties of entorhinal cortex neurons and early alterations in an Alzheimer's disease transgenic model. Pflugers Arch 466:1437-1450. doi:10.1007/s00424-013-1368-z 49. Marchani E E, Bird T D, Steinbart E J, Rosenthal B, Yu C-B, Schclleiibeig G D, Wijsman E M (2010) Evidence for three loci modifying age-at-onset of Alzheimer's disease in early-onset PSEN2 families. Am J Med Genet B Neuropsychiatr Genet 153B:1031-1041. doi:10.1002/ajmg.b.31072

50. Maroof A M, Keros S, Tyson J A, Ying S-W, Ganat Y M, Merkle F T, Liu B, Goulburn A, Stanley E G, Elefanty A G, Widmer H R, Eggan K, Goldstein P A, Anderson S A, Studer L (2013) Directed differentiation and functional maturation of cortical interneurons from human embryonic stem cells. Cell Stem Cell 12:559-572. doi:10.1016/j.stem.2013.04.008

51. Minkiewicz J, de Rivero Vaccari J P, Keane R W (2013) Human astrocytes express a novel NLRP2 inflammasome. Glia 61:1113-1121. doi:10.1002/glia.22499

52. Mucke L, Selkoe D J (2012) Neurotoxicity of amyloid-protein: synaptic and network dysfunction. Cold Spring Harb Perspect Med 2:a006338. doi:10.1101/cshperspect.a006338

53. Müller U, Winter P, Graeber M B (2011) Alois Alzheimer's case, Auguste D., did not carry the N141I mutation in <emph typequot;ital"> PSEN2</emph> characteristic of Alzheimer disease in Volga Germans. Arch Neurol 68:1210. doi:10.1001/archneurol.2011.218

54. Nava-Mesa M O, Jiménez-Diaz L, Yajeya J, Navarro-Lopez J D (2013) Amyloid-induces synaptic dysfunction through G protein-gated inwardly rectifying potassium channels in the fimbria-CA3 hippocampal synapse. Front Cell Neurosci 7:117. doi:10.3389/fncel.2013.00117

55. Nelson O, Supnet C, Tolia A, Horre K, De Strooper B, Bezprozvanny I (2011) Mutagenesis mapping of the Presenilin 1 calcium leak conductance pore. J Biol Chem 286:22339-22347. doi:10.1074/jbc.M111.243063

56. Nieweg K, Andreyeva A, van Stegen B, Tanriover G, Gottmann K (2015) Alzheimer's disease-related amyloid-induces synaptotoxicity in human iPS cell-derived neurons. Cell Death Dis 6:e1 709. doi:10.1038/cddis.2015.72

57. Oddo S, Caccamo A, Shepherd J D, Murphy M P, Golde T E, Kayed R, Metherate R, Mattson M P, Akbari Y, LaFerla F M (2003) Triple-transgenic model of Alzheimer's disease with plaques and tangles: intracellular Abeta and synaptic dysfunction. Neuron 39:409-421

58. Onos K D, Sukoff Rizzo S J, Howell G R, Sasner M (2016) Toward more predictive genetic mouse models of Alzheimer's disease. Brain Res Bull 122:1-11. doi:10.1016/j.brainresbull.2015.12.003

59. Oyama F, Sawamura N, Kobayashi K, Morishima-Kawashima M, Kuramochi T, Ito M, Tomita T, Maruyama R, Saido T C, Iwatsubo T, Capell A, Walter J, Grünberg J, Ueyama Y, Haass C, Ihara Y (1998) Mutant presenilin 2 transgenic mouse: effect on an age-dependent increase of amyloid beta-protein 42 in the brain. J Neurochem 71:313-322

60. Paull D, Sevilla A, Zhou H, Hahn A K, Kim H, Napolitano C, Tsankov A, Shang L, Krumholz K, Jagadeesan P, Woodard C M, Sun B, Vilboux T, Zimmer M, Forero E, Moroziewicz D N, Martinez H, Malicdan M C V, Weiss K A, Vensand L B, Dusenberry C R, Polus H, Sy K T L, Kahler D J, Gahl W A, Solomon S L, Chang S, Meissner A, Eggan K, Noggle S A (2015) Automated, high-throughput derivation, characterization and differentiation of induced pluripotent stem cells. Nat Methods 12:885-892. doi:10.1038/nmeth.3507

61. Perry E K, Gibson P H, Blessed G, Perry R H, Tomlinson B E (1977) Neurotransmitter enzyme abnormalities in senile dementia. Choline acetyltransferase and glutamic acid decarboxylase activities in necropsy brain tissue. J Neurol Sci 34:247-265

62. Pini L, Pievani M, Bocchetta M, Altomare D, Bosco P, Cavedo E, Galluzzi S, Marizzoni M, Frisoni G B (2016) Brain atrophy in Alzheimer's disease and aging. Ageing Res Rev 30:25-48. doi:10.1016/j.arr.2016.01.002

63. Price D L, Tanzi R E, Borchelt D R, Sisodia S S (1998) Alzheimer's disease: genetic studies and transgenic models. Annu Rev Genet 32:461-493. doi:10.1146/annurev.genet.32.1.461

64. Proulx É, Fraser P, McLaurin J, Lambe E K (2015) Impaired cholinergic excitation of prefrontal attention circuitry in the TgCRND8 model of Alzheimer's disease. J Neurosci 35:12779-12791. doi:10.1523/JNEUROSCI.4501-14.2015

65. Pruszak J, Sonntag K C, Aung M H, Sanchez-Pernaute R, Isacson 0 (2007) Markers and methods for cell sorting of human embryonic stem cell-derived neural cell populations. Stem Cells 25(9):2257-2268 Epub 2007 Jun. 21. PubMed PMID: 17588935; PubMed Central PMCID: PMC2238728
66. Ran F A, Hsu P D, Wright J, Agarwala V, Scott D A, Zhang F (2013) Genome engineering using the CRISPR-Cas9 system. Nat Protoc 8:2281-2308. doi:10.1038/nprot.2013.143
67. Ren S-C, Shao H, Ji W-G, Jiang H-H, Xu F, Chen P-Z, Mi Z, Wen B, Zhu G-X, Zhu Z-R (2015) Riluzole prevents soluble $a_{1-42}$ oligomers-induced perturbation of spontaneous discharge in the hippocampal CA1 region of rats. Amyloid 22:36-44. doi:10.3109/13506129.201d 0.990558
68. Richardson C D, Ray G J, DeWitt M A, Curie G L, Corn J E (2016) Enhancing homology-directed genome editing by catalytically active and inactive CRISPR-Cas9 using asymmetric donor DNA. Nat Biotechnol 34:339-344. doi:10.1038/nbt.3481
69. Ripoli C, Cocco S, Li Puma D D, Piacentini R, Mastrodonato A, Scala F, Puzzo D, D'Ascenzo M, Grassi C (2014) Intracellular accumulation of Amyloid-(a) protein plays a major role in a-induced alterations of Glutamatergic synaptic transmission and plasticity. J Neurosci 34:12893-12903. doi:10.1523/JNEUROSCI.1201-14.2014
70. Roder S, Danober L, Pozza M, Lingenhoehl K, Wiederhold K-H, Olpe H-R (2003) Electrophysiological studies on the hippocampus and prefrontal cortex assessing the effects of amyloidosis in amyloid precursor protein 23 transgenic mice. Neuroscience 120:705-720. doi:10.1016/S0306-4522(03)00381-6
71. Rylett R J, Ball M J, Colhoun E H (1983) Evidence for high affinity choline transport in synaptosomes prepared from hippocampus and neocortex of patients with Alzheimer's disease. Brain Res 289:169-175
72. Sachse C C, Kim Y H, Agsten M, Huth T, Alzheimer C, Kovacs D M, Kim D Y (2013) BACE1 and presenilin/-secretase regulate proteolytic processing of KCNE1 and 2, auxiliary subunits of voltage-gated potassium channels. FASEB J 27:2458-2467. doi:10.1096/fj.12-214056
73. Sawamura N, Morishima-Kawashima M, Waki H, Kobayashi K, Kuramochi T, Frosch M P, Ding K, Ito M, Kim T W, Tanzi R E, Oyama F, Tabira T, Ando S, Ihara Y (2000) Mutant-presenilin 2-transgenic mice: a large increase in the levels of a beta 42 is presumably associated with the low-density membrane domain that contains decreased levels of glycerophospholipids and sphingomyelin. J Biol Chem 275:27901-27908. doi:10.1074/jbc.M004308200
74. Sepulveda-Falla D, Barrera-Ocampo A, Hagel C, Korwitz A, Vinueza-Veloz M F, Zhou K, Schonewille M, Zhou H, Velazquez-Perez L, Rodriguez-Labrada R, Villegas A, Ferrer I, Lopera F, Langer T, De Zeeuw C I, Glatzel M (2014) Familial Alzheimer's disease-associated presenilin-1 alters cerebellar activity and calcium homeostasis. J Clin Invest 124:1552-1567. doi:10.1 172/JCI66407
75. Šišková. Z, Justus D, Kaneko H, Friedrichs D, Henneberg N, Beutel T, Pitsch J, Schoch S, Becker A, von der Kammer H, Remy S (2014) Dendritic structural degeneration is functionally linked to cellular Hyperexcitability in a mouse model of Alzheimer's disease. Neuron 84:1023-1033. doi:10.1016/j.neuron. 2014.10.024
76. Smilansky A, Dangoor L, Nakdimon I, Ben-Hail D, Mizrachi D, Shoshan-Barmatz V (2015) The voltage-dependent Anion Channel 1 mediates Amyloidtoxicity and represents a potential target for Alzheimer disease therapy. J Biol Chem 290:30670-30683. doi:10.1074/jbc.M115.69149
77. Sproul A A, Jacob S, Pre D, Kim S H, Nestor M W, Navarro-Sobrino M, Santa-Maria I, Zimmer M, Aubry S, Steele J W, Kahler D J, Dranovsky A, Arancio O, Crary J F, Gandy S, Noggle S A (2014) Characterization and molecular profiling of PSEN1 familial Alzheimer's disease iPSC-derived neural progenitors. PLoS One 9:e84547. doi:10.1371/journal.pone.0084547
78. Stine W B, Dahlgren K N, Krafft G A, LaDu M J (2003) In vitro characterization of conditions for amyloid-beta peptide oligomerization and fibrillogenesis. J Biol Chem 278:11612-11622. doi:10.1074/jbc.M210207200
79. Stutzmann G E, Caccamo A, LaFerla F M, Parker I (2004) Dysregulated IP3 signaling in cortical neurons of knock-in mice expressing an Alzheimer's-linked mutation in Presenilin1 results in exaggerated Ca2+ signals and altered membrane excitability. J Neurosci 24:508-513. doi:10.1523/JNEUROSCI.4386-03.2004
80. Supnet C, Bezprozvanny I (2011) Presenilins function in ER calcium leak and Alzheimer's disease pathogenesis. Cell Calcium 50:303-309. doi:10.1016/j.ceca.2011.05.013
81. Takahashi K, Yamanaka S (2006) Induction of Pluripotent stem cells from mouse embryonic and adult fibroblast cultures by defined factors. Cell 126(4):663-676. doi: 10.1016/j.cell.2006.07.024
82. Thal L J, Fuld P A, Masur D M, Sharpless N S (1983) Oral physostigmine and lecithin improve memory in Alzheimer disease. Ann Neurol 13:491-496. doi:10.1002/ana.410130504
83. Tomita T, Maruyama K, Saido T C, Kume H, Shinozaki K, Tokuhiro S, Capell A, Walter J, Grünberg J, Haass C, Iwatsubo T, Obata K (1997) The presenilin 2 mutation (N141I) linked to familial Alzheimer disease (Volga German families) increases the secretion of amyloid beta protein ending at the 42nd (or 43rd) residue. Proc Natl Acad Sci USA 94:2025-2030
84. Tu H, Nelson O, Bezprozvanny A, Wang Z, Lee S-F, Hao Y-H, Serneels L, De Strooper B, Yu G, Bezprozvanny I (2006) Presenilins form ER Ca2+ leak channels, a function disrupted by familial Alzheimer's disease-linked mutations. Cell 126:981-993. doi:10.1016/j.cell.2006.06.059
85. Tucker E S, Segall S, Gopalakrishna D, Wu Y, Vernon M, Pollcux F, Lamantia A-S (2008) Molecular specification and patterning of progenitor cells in the lateral and medial ganglionic eminences. J Neurosci 28:9504-9518. doi: 10.1523/JNEUROSCI.2341-08.2008
86. Varga E, Juhász G, Bozsó Z, Penke B, Fülüp L, Szegedi V (2014) Abeta(1-42) enhances neuronal excitability in the CA1 via NR2B subunit-containing NMDA receptors. Neural Plast 2014:1-12. doi:10.1155/2014/584314
87. Verdile G, Gandy S E, Martins R N (2007) The role of presenilin and its interacting proteins in the biogenesis of Alzheimer's beta amyloid. Neurochem Res 32:609-623. doi:10.1007/s11064-006-9131-x
88. Wang X, Zhang X-G, Zhou T-T, Li N, Jang C-Y, Xiao Z-C, Ma Q-H, Li S (2016) Elevated neuronal excitability due to modulation of the voltage-gated Sodium Channel Nav1.6 by A 1-42. Front Neurosci 10:94. doi:10.3389/fnins.2016.00094

89. Wicklund L, Leão R N, Strömberg A-M, Mousavi M, Hovatta O, Nordberg A, Marutle A (2010) B-amyloid 1-42 oligomers impair function of human embryonic stem cell-derived forebrain cholinergic neurons. PLoS One 5: e15600. doi:10.1371/journal.pone.0015600
90. Wolfe M S, Selkoe D J, Xia W, Ostaszewski B L, Diehl T S, Kimberly W T (1999) Two transmembrane aspartates in presenilin-1 required for presenilin endoproteolysis and [gamma]-secretase activity. Nature 398:513-517. doi: 10.1038/19077
91. Xu H, Sakiyama-Elbert S E (2015) Directed differentiation of V3 Interneurons from mouse embryonic stem cells. Stem Cells Dev 24: 2723-2732. doi:10.1089/scd.2015.0122
92. Xu W, Fitzgerald S, Nixon R A, Levy E, Wilson D A (2015) Early hyperactivity in lateral entorhinal cortex is associated with elevated levels of A PP metabolites in the Tg2576 mouse model of Alzheimer's disease. Exp Neurol 264:82-91. doi:10.1016/j.expneurol.2014.12.008
93. Yagi T, Ito D, Okada Y, Akamatsu W, Nihei Y, Yoshizaki T, Yamanaka S, Okano H, Suzuki N (2011) Modeling familial Alzheimer's disease with induced pluripotent stem cells. Hum Mol Genet 20:4530-4539. doi:10.1093/hmg/ddr394
94. Yue W, Li Y, Zhang T, Jiang M, Qian Y, Zhang M, Sheng N, Feng S, Tang K, Yu X, Shu Y, Yue C, Jing N (2015) ESC-derived basal forebrain cholinergic neurons ameliorate the cognitive symptoms associated with Alzheimer's disease in mouse models. Stem Cell Rep 5:776-790. doi:10.1016/j.stemcr.2015.09.01

Although the invention has been described with reference to the examples herein, it will be understood that modifications and variations are encompassed within the spirit and scope of the invention. Accordingly, the invention is limited only by the following claims.

What is claimed is:

1. A method of generating basal forebrain cholinergic neurons (BFCNs) comprising:
   culturing pluripotent stem cells (PSCs) in a basal media comprising an inhibitor of transforming growth factor beta (TGF-β) signaling and an activator of sonic hedgehog (Shh) signaling thereby inducing neuroectodermal differentiation, wherein the inhibitor of TGF-β signaling is SB431542 and LDN193189 and the activator of Shh signaling is smoothened agonist (SAG) and purmorphamine, and
   wherein the basal media lacks basic fibroblast growth factor (bFGF), TGF-β, lithium chloride (Li—Cl), GABA and pipecolic acid, thereby generating BFCNs.

2. The method of claim 1, wherein culturing is performed for a duration of about 4 to 9 days.

3. The method of claim 1, wherein the inhibitor is present in the culture media from about day 2 to day 8.

4. The method of claim 1, further comprising selecting for isolating CD271+cells.

5. The method of claim 4, wherein isolating is performed after about 9 to 12 days of culturing.

6. The method of claim 5, further comprising culturing the CD271+cells to generate neuronal embryoid bodies (NEBs).

7. The method of claim 6, wherein the CD271+cells are cultured for about 7 days thereby generating NEBs.

8. The method of claim 7, further comprising:
   a) harvesting the NEBs; and
   b) dissociating cells of the NEBs and re-plating the dissociated cells as a monolayer.

9. The method of claim 8, wherein the re-plated cells are cultured for an additional duration in culture media having growth factors to maintain survival of the cells, and wherein the cells express Tuj1, MAP2, BF1, Nkx2.1 and p75.

10. The method of claim 8, where the cultured cells exhibit mature action potentials.

11. The method of claim 1, further comprising culturing the cells to confluence prior to contacting the cells with the activator or inhibitor.

12. The method of claim 1, wherein the PSCs are human cells.

13. The method of claim 1, wherein the PSCs are induced pluripotent stem cells (iPSCs).

14. The method of claim 13, wherein the iPSCs are derived from a subject diagnosed with, or at risk of having Alzheimer's disease (AD).

15. The method of claim 14, wherein the iPSCs are produced using a BFCN from the subject having a mutation in presenilin 2 (PSEN2).

16. The method of claim 15, wherein the mutation is PSEN2$^{N141I}$.

17. The method of claim 15, wherein the mutation is repaired after generation of the iPSCs.

18. The method of claim 17, wherein the mutation is repaired using a gene editing system selected from the group consisting of CRISPR/Cas system, Cre/Lox system, TALEN system and homologous recombination.

19. The method of claim 17, wherein the cultured cells exhibit a normalization of Aβ42/40 ratio as compared to control.

20. The method of claim 17, wherein the cultured cells exhibit a reduction in electrophysiological deficit as compared to control.

21. The method of claim 20, wherein the reduction in electrophysiological deficit comprises restoration of maximal number of spikes and spike height in response to depolarizing current as compared to control.

22. The method of claim 1, wherein the cultured cells exhibit homogeneous expression of Nkx2.1 by day 8 of culturing.

23. The method of claim 1, wherein the cultured cells exhibit recordable action potentials by day 8 of culturing.

24. The method of claim 1, wherein the cultured cells exhibit mature action potentials by day 38 of culturing.

* * * * *